US011702633B2

(12) United States Patent
Jang et al.

(10) Patent No.: US 11,702,633 B2

(45) **Date of Patent: *Jul. 18, 2023**

(54) COMPOSITION FOR CULTURING REGULATORY T CELLS AND USE THEREOF

(71) Applicant: GI CELL, INC., Gyeonggi-do (KR)

(72) Inventors: Myoung Ho Jang, Seoul (KR); Chun-Pyo Hong, Gyeonggi-do (KR); Chea Ha Kim, Seoul (KR); Hye Ri Kim, Seoul (KR)

(73) Assignee: GI CELL, INC., Gyeonggi-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/743,181

(22) Filed: May 12, 2022

(65) Prior Publication Data

US 2022/0290102 A1 Sep. 15, 2022

Related U.S. Application Data

(63) Continuation of application No. PCT/KR2020/016382, filed on Nov. 19, 2020.

(30) Foreign Application Priority Data

Nov. 20, 2019 (KR) ........................ 10-2019-0149779
Mar. 18, 2020 (KR) ........................ 10-2020-0033229

(51) Int. Cl.
*C12N 5/0783* (2010.01)
*A61K 35/17* (2015.01)

(52) U.S. Cl.
CPC ............ *C12N 5/0636* (2013.01); *A61K 35/17* (2013.01); *C12N 2501/2302* (2013.01); *C12N 2501/51* (2013.01)

(58) Field of Classification Search
None
See application file for complete search history.

(56) References Cited

U.S. PATENT DOCUMENTS

| | | | | |
|---|---|---|---|---|
| 2007/0172947 | A1 | 7/2007 | Shirwan | |
| 2011/0052529 | A1* | 3/2011 | Shirwan ............... | A61K 47/665 424/193.1 |

FOREIGN PATENT DOCUMENTS

| | | | |
|---|---|---|---|
| CN | 101378783 | A | 3/2009 |
| CN | 110392392 | A | 10/2019 |
| JP | 2009521409 | A | 6/2009 |
| KR | 1020180069903 | A | 6/2018 |
| WO | 2017220989 | A1 | 12/2017 |

OTHER PUBLICATIONS

Chan, L., et al., "IL2/B7.1 (CD80) Fusagene Transduction of AML Blasts by a Self-Inactivating Lentiviral Vector Stimulates T Cell Responses a Strategy to Generate Whole Cell Vaccines for AML", Molecular Therapy, 2005, Page (s) DOI: 10.1016/j.ymthe.2004.09.006, vol. 11, No. 1, Publisher: The American Society of Gene Therapy.

Gershon, R.K., et al., "Cell Interactions in the Induction of Tolerance: The Role of Thymic Lymphocytes", Immunology, 1970, pp. 723-737, vol. 18.

Ingram, W., et al., "Human CD80/IL2 lentivirus transduced acute myeloid leukaemia cells enhance cytolytic activity in vitro in spite of an increase in regulatory CD4 T cells in a subset of cultures", Cancer Immunol Immunother, 2009, pp. 1679-1690; DOI 10.1007/S00262-009-0679-6, vol. 58, Publisher: Springer.

Karumuthil-Melethil, S., et al., "TLR2—and Dectin 1-Associated Innate Immune Response Modulates T-Cell Response to Pancreatic-Cell Antigen and Prevents Type 1 Diabetes", Diabetes, 2015, pp. 1341-1357, vol. 64.

Nishikawa, H., et al., "Regulatory T cells in tumor immunity", International Journal of Cancer, 2010, pp. 759-767, vol. 125, Publisher: uicc global cancer control.

Park, J.C., et al., "GI101, a novel triple-targeting bispecific CD80-lgG4-IL2variant fusion protein, elicits synergistic anti-tumour effects in preclinical models", Annals of Oncology, 2019, pp. v475-v532; 10.1093/annonc/mdz253, vol. 30, No. 5.

Sakaguchi, S., et al., "Immunologic Self-Tolerance Maintained by Activated T Cells Expressing IL-2 Receptor—Chains (CD25)", J. Immunol., 1995, pp. 1151-1164, vol. 155, Publisher: The American Association of Immunologists.

Ning, Y., et al., "CD4+ CD25+ CD127 low/—T Cells More Specific Treg Population in Human Peripheral Blood", Inflammation, 2012, DGI:10.1007/S10753-012-9496-8, vol. 35, No. 6.

Office Action issued in counterpart Japanese Patent Application No. 2022-529596 dated Nov. 7, 2022.

English Translation of Office Action issued in counterpartJapanese Patent Application No. 2022-529596 dated Nov. 7, 2022.

English Translation of Office Action Cited in Counterpart Chinese Patent Application No. 202080078640.8 dated Dec. 20, 2022.

English Translation of Search Report in Counterpart Chinese Patent Application No. 22080078640.8 dated Dec. 14, 2022.

Office Action Cited in Counterpart Chinese Patent Application No. 202080078640.8 dated Dec. 20, 2022.

(Continued)

*Primary Examiner* — Amy E Juedes

(74) *Attorney, Agent, or Firm* — Hultquist, PLLC; Steven J. Hultquist

(57) ABSTRACT

The present invention relates to a method for effectively proliferating regulatory T cells, by which, particularly, in the presence of a fusion protein dimer comprising IL-2 protein or a variant thereof and CD80 protein or a fragment thereof, CD4+, CD25+, and CD127− T cells can be effectively proliferated. In particular, when combined with a predetermined cell culture medium, regulatory T cells such as CD4+, CD25+, and CD127− can be effectively and specifically proliferated. In addition, when the method is used, it has been confirmed that the survival rate of regulatory T cells is remarkably increased as compared to a conventionally used culture method using IL-2, and a significant increase in the yield of Foxp3+ regulatory T cells has been confirmed. Thus, such a proliferation method can be used in the field of cell therapeutic agents using regulatory T cells.

6 Claims, 25 Drawing Sheets

Specification includes a Sequence Listing.

(56) References Cited

OTHER PUBLICATIONS

Office Action issued in counterpart Japanese Patent Application No. 2022-529596 dated Mar. 22, 2023.
English Translation of Office Action issued in counterpart Japanese Patent Application No. 2022-529596 dated Mar. 22, 2023.
Finkelstein, A.V., et al., "F59 Biomechanics: Kypc lecture with answers and stereochronic illustration and questions: tutorial", Protein Physics: A course of lectures with color and stereosopic illustrations and tasks: textbook, 2012, p. 23, vol. 4th edition, No. M:KDU-524.
Fiknelstein, A.V., et al., English Translation: "F59 Biomechanics: Kypc lecture with answers and stereochronic illustration and questions: tutorial", Protein Physics: A course of lectures with color and stereoscopic illustrations and tasks: textbook, 2012, p. 23, vol. 4th edition, No. M:KDU-524.
Romano, M., et al., "Treg therapy in transplantation a general overview", King's College London, Division of Transplantation Immunology & Mucosal Biology, 2016, doi: 1111/tri.12909.
Office Action Issued in Russian Patent Application No. 2022113174 dated Apr. 25, 2023.
English Translation of Office Action Issued in Russian Patent Application No. 2022113174 dated Apr. 25, 2023.
Search Report Issued in Russian Patent Application No. 2022113174 dated Apr. 25, 2023.
Liu, W., et al., "CD127 expression inversely correlates with FoxP3 and suppressive function of human CD4+ T reg cells", The Journal of Experimental Medicine, 2006, pp. 1701-1711, vol. 203, No. 7, Publisher: The Rockefeller University Press.

* cited by examiner

Analytical size exclusion chromatography (SEC)

| | RT | Area | % Area | Height |
|---|---|---|---|---|
| 1 | 6.492 | 143663 | 1.66 | 5185 |
| 2 | 7.528 | 8497629 | 98.06 | 250509 |
| 3 | 12.546 | 24077 | 0.28 | 2005 |

| | Peak Name | RT | Area | % Area | Height |
|---|---|---|---|---|---|
| 1 | HMW1 | 15.506 | 28137 | 0.52 | 426 |
| 2 | Monomer | 18.158 | 5363386 | 99.48 | 148945 |

| | RT | Area | % Area | Height |
|---|---|---|---|---|
| 1 | 9.652 | 2996084 | 98.41 | 26478 |
| 2 | 12.535 | 48430 | 1.59 | 2882 |

| | Peak Name | RT | Area | % Area | Height |
|---|---|---|---|---|---|
| 1 | HMW | 13.321 | 33675 | 1.13 | 625 |
| 2 | monomer | 14.775 | 2952831 | 98.87 | 43291 |

CD4 enrichment
Initial
6 Days enriched
with CD4
GI101
GI-101_WT
CD80-Fc+Fc-IL2v2
CD80-Fc+Fc-wt
3.2nM
50nM
CD4+CD25
T cell
Foxp3hi
Treg
CD4
Foxp3

CD4 enrichment Initial
6 Days post-FACS sorting
GI101
GI-101_WT
CD80-Fc+Fc-IL2v2
CD80-Fc+Fc-wt
3.2nM
50nM
Treg
T cell
CD4
Foxp3

SEQUENCE LISTING

```
<160> NUMBER OF SEQ ID NOS: 46

<210> SEQ ID NO 1
<211> LENGTH: 25
```

```
<212> TYPE: PRT
<213> ORGANISM: Artificial Sequence
<220> FEATURE:
<223> OTHER INFORMATION: signal peptide (TPA)

<400> SEQUENCE: 1

Met Asp Ala Met Leu Arg Gly Leu Cys Cys Val Leu Leu Leu Cys Gly
1               5                   10                  15

Ala Val Phe Val Ser Pro Ser His Ala
            20                  25


<210> SEQ ID NO 2
<211> LENGTH: 208
<212> TYPE: PRT
<213> ORGANISM: Artificial Sequence
<220> FEATURE:
<223> OTHER INFORMATION: hB7-1:35-242

<400> SEQUENCE: 2

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 3
<211> LENGTH: 30
<212> TYPE: PRT
<213> ORGANISM: Artificial Sequence
<220> FEATURE:
<223> OTHER INFORMATION: hinge with linker

<400> SEQUENCE: 3

Gly Ser Gly Gly Gly Gly Ser Gly Gly Gly Gly Ser Gly Gly Gly Gly
1               5                   10                  15

Ser Ala Glu Ser Lys Tyr Gly Pro Pro Cys Pro Pro Cys Pro
            20                  25                  30
```

<210> SEQ ID NO 4
<211> LENGTH: 216
<212> TYPE: PRT
<213> ORGANISM: Artificial Sequence
<220> FEATURE:
<223> OTHER INFORMATION: immunoglobulin fc

<400> SEQUENCE: 4

```
Ala Pro Glu Ala Ala Gly Gly Pro Ser Val Phe Leu Phe Pro Pro Lys
1               5                   10                  15

Pro Lys Asp Gln Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Leu His Glu Ala Leu His Asn His Tyr Thr Gln
        195                 200                 205

Lys Ser Leu Ser Leu Ser Leu Gly
    210                 215
```

<210> SEQ ID NO 5
<211> LENGTH: 5
<212> TYPE: PRT
<213> ORGANISM: Artificial Sequence
<220> FEATURE:
<223> OTHER INFORMATION: linker

<400> SEQUENCE: 5

```
Gly Gly Gly Gly Ser
1               5
```

<210> SEQ ID NO 6
<211> LENGTH: 133
<212> TYPE: PRT
<213> ORGANISM: Artificial Sequence
<220> FEATURE:
<223> OTHER INFORMATION: hIL-2M

<400> SEQUENCE: 6

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30
```

```
Asn Pro Lys Leu Thr Ala Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 7
<211> LENGTH: 617
<212> TYPE: PRT
<213> ORGANISM: Artificial Sequence
<220> FEATURE:
<223> OTHER INFORMATION: fusion protein comprising variants of IL-2 and
      fragments of CD80

<400> SEQUENCE: 7

Met Asp Ala Met Leu Arg Gly Leu Cys Cys Val Leu Leu Leu Cys Gly
1               5                   10                  15

Ala Val Phe Val Ser Pro Ser His Ala Val Ile His Val Thr Lys Glu
            20                  25                  30

Val Lys Glu Val Ala Thr Leu Ser Cys Gly His Asn Val Ser Val Glu
        35                  40                  45

Glu Leu Ala Gln Thr Arg Ile Tyr Trp Gln Lys Glu Lys Lys Met Val
    50                  55                  60

Leu Thr Met Met Ser Gly Asp Met Asn Ile Trp Pro Glu Tyr Lys Asn
65                  70                  75                  80

Arg Thr Ile Phe Asp Ile Thr Asn Asn Leu Ser Ile Val Ile Leu Ala
                85                  90                  95

Leu Arg Pro Ser Asp Glu Gly Thr Tyr Glu Cys Val Val Leu Lys Tyr
            100                 105                 110

Glu Lys Asp Ala Phe Lys Arg Glu His Leu Ala Glu Val Thr Leu Ser
        115                 120                 125

Val Lys Ala Asp Phe Pro Thr Pro Ser Ile Ser Asp Phe Glu Ile Pro
    130                 135                 140

Thr Ser Asn Ile Arg Arg Ile Ile Cys Ser Thr Ser Gly Gly Phe Pro
145                 150                 155                 160

Glu Pro His Leu Ser Trp Leu Glu Asn Gly Glu Glu Leu Asn Ala Ile
                165                 170                 175

Asn Thr Thr Val Ser Gln Asp Pro Glu Thr Glu Leu Tyr Ala Val Ser
            180                 185                 190

Ser Lys Leu Asp Phe Asn Met Thr Thr Asn His Ser Phe Met Cys Leu
        195                 200                 205

Ile Lys Tyr Gly His Leu Arg Val Asn Gln Thr Phe Asn Trp Asn Thr
    210                 215                 220

Thr Lys Gln Glu His Phe Pro Asp Asn Gly Ser Gly Gly Gly Gly Ser
225                 230                 235                 240

Gly Gly Gly Gly Ser Gly Gly Gly Gly Ser Ala Glu Ser Lys Tyr Gly
```

```
                245                 250                 255

Pro Pro Cys Pro Pro Cys Pro Ala Pro Glu Ala Ala Gly Gly Pro Ser
            260                 265                 270

Val Phe Leu Phe Pro Pro Lys Pro Lys Asp Gln Leu Met Ile Ser Arg
        275                 280                 285

Thr Pro Glu Val Thr Cys Val Val Val Asp Val Ser Gln Glu Asp Pro
    290                 295                 300

Glu Val Gln Phe Asn Trp Tyr Val Asp Gly Val Glu Val His Asn Ala
305                 310                 315                 320

Lys Thr Lys Pro Arg Glu Glu Gln Phe Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Gly Leu Pro Ser Ser Ile Glu Lys Thr
        355                 360                 365

Ile Ser Lys Ala Lys Gly Gln Pro Arg Glu Pro Gln Val Tyr Thr Leu
    370                 375                 380

Pro Pro Ser Gln Glu Glu Met Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Arg Leu Thr Val Asp Lys Ser
        435                 440                 445

Arg Trp Gln Glu Gly Asn Val Phe Ser Cys Ser Val Leu His Glu Ala
    450                 455                 460

Leu His Asn His Tyr Thr Gln Lys Ser Leu Ser Leu Ser Leu Gly Gly
465                 470                 475                 480

Gly Gly Gly Ser Ala Pro Thr Ser Ser Ser Thr Lys Lys Thr Gln Leu
                485                 490                 495

Gln Leu Glu His Leu Leu Leu Asp Leu Gln Met Ile Leu Asn Gly Ile
            500                 505                 510

Asn Asn Tyr Lys Asn Pro Lys Leu Thr Ala Met Leu Thr Ala Lys Phe
        515                 520                 525

Tyr Met Pro Lys Lys Ala Thr Glu Leu Lys His Leu Gln Cys Leu Glu
    530                 535                 540

Glu Glu Leu Lys Pro Leu Glu Glu Val Leu Asn Leu Ala Gln Ser Lys
545                 550                 555                 560

Asn Phe His Leu Arg Pro Arg Asp Leu Ile Ser Asn Ile Asn Val Ile
                565                 570                 575

Val Leu Glu Leu Lys Gly Ser Glu Thr Thr Phe Met Cys Glu Tyr Ala
            580                 585                 590

Asp Glu Thr Ala Thr Ile Val Glu Phe Leu Asn Arg Trp Ile Thr Phe
        595                 600                 605

Cys Gln Ser Ile Ile Ser Thr Leu Thr
    610                 615
```

<210> SEQ ID NO 8
<211> LENGTH: 1857
<212> TYPE: DNA
<213> ORGANISM: Artificial Sequence
<220> FEATURE:
<223> OTHER INFORMATION: nucleotides coding fusion protein (GI101)

<400> SEQUENCE: 8

```
atggatgcta tgctgagagg cctgtgttgc gtgctgctgc tgtgtggcgc tgtgttcgtg     60
tctccttctc acgctgtgat ccacgtgacc aaagaagtga aagaggtcgc cacactgtcc    120
tgcggccaca acgtttcagt ggaagaactg gcccagacca ggatctactg gcagaaagaa    180
aagaaaatgg tgctgaccat gatgtccggc gacatgaaca tctggcctga gtacaagaac    240
cggaccatct tcgacatcac caacaacctg tccatcgtga ttctggccct gaggccttct    300
gatgagggca cctatgagtg cgtggtgctg aagtacgaga aggacgcctt caagcgcgag    360
cacctggctg aagtgacact gtccgtgaag gccgactttc ccacaccttc catctccgac    420
ttcgagatcc ctacctccaa catccggcgg atcatctgtt ctacctctgg cggctttcct    480
gagcctcacc tgtcttggct ggaaaacggc gaggaactga acgccatcaa caccaccgtg    540
tctcaggacc ccgaaaccga gctgtacgct gtgtcctcca agctggactt caacatgacc    600
accaaccaca gcttcatgtg cctgattaag tacggccacc tgagagtgaa ccagaccttc    660
aactggaaca ccaccaagca agagcacttc cctgacaatg gatctggcgg cggaggttct    720
ggcggaggtg gaagcggagg cggaggatct gctgagtcta agtatggccc tccttgtcct    780
ccatgtcctg ctccagaagc tgctggcgga ccctctgtgt tcctgtttcc tccaaagcct    840
aaggaccagc tcatgatctc tcggacaccc gaagtgacct gcgtggtggt ggatgtgtct    900
caagaggacc ctgaggtgca gttcaattgg tacgtggacg gcgtggaagt gcacaacgcc    960
aagaccaagc ctagagagga acagttcaac tccacctaca gagtggtgtc cgtgctgacc   1020
gtgctgcacc aggattggct gaacggcaaa gagtacaagt gcaaggtgtc caacaagggc   1080
ctgccttcca gcatcgaaaa gaccatctcc aaggctaagg gccagcctag ggaaccccag   1140
gtttacaccc tgcctccaag ccaagaggaa atgaccaaga accaggtgtc cctgacctgc   1200
ctggtcaagg gcttctaccc ttccgacatt gccgtggaat gggagtccaa tggccagcct   1260
gagaacaact acaagaccac acctcctgtg ctggactccg acggctcctt ctttctgtac   1320
tctcgcctga ccgtggacaa gtctagatgg caagagggca acgtgttctc ctgctctgtg   1380
ctgcacgagg ccctgcacaa tcactacacc cagaagtccc tgtctctgtc tcttggaggt   1440
ggtggcggtt ctgcccctac cagctcctct accaagaaaa cccagctcca gttggagcat   1500
ctgctgctgg acctccagat gattctgaac gggatcaaca actataagaa ccccaagctg   1560
accgccatgc tgaccgctaa gttctacatg cccaagaagg ccaccgagct gaagcacctc   1620
cagtgcctgg aagaagaact gaagcccctg gaagaggtgc tgaatctggc ccagtccaag   1680
aacttccacc tgaggccacg ggacctgatc agcaacatca acgtgatcgt gctggaactg   1740
aagggctccg agacaacctt tatgtgcgag tacgccgacg agacagccac catcgtggaa   1800
tttctgaacc ggtggatcac cttctgccag agcatcatct ccacactgac ctgatga      1857
```

<210> SEQ ID NO 9
<211> LENGTH: 592
<212> TYPE: PRT
<213> ORGANISM: Artificial Sequence
<220> FEATURE:
<223> OTHER INFORMATION: fusion protein (GI101)

<400> SEQUENCE: 9

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30
```

```
Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445
```

```
Leu Ser Leu Ser Leu Gly Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590
```

<210> SEQ ID NO 10
<211> LENGTH: 133
<212> TYPE: PRT
<213> ORGANISM: Artificial Sequence
<220> FEATURE:
<223> OTHER INFORMATION: hIL-2

<400> SEQUENCE: 10

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 11
<211> LENGTH: 288
<212> TYPE: PRT
<213> ORGANISM: Artificial Sequence
<220> FEATURE:
<223> OTHER INFORMATION: CD80

<400> SEQUENCE: 11

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30
```

```
Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285


<210> SEQ ID NO 12
<211> LENGTH: 215
<212> TYPE: PRT
<213> ORGANISM: Artificial Sequence
<220> FEATURE:
<223> OTHER INFORMATION: modified Fc

<400> SEQUENCE: 12

Ser His Thr Gln Pro Leu Gly Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser Gln Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110
```

```
Glu Pro Gln Val Tyr Thr Leu Pro Pro Ser Gln Glu Glu Met Thr Lys
        115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Arg Leu Thr Val Asp Lys Ser Arg Trp Gln Glu Gly Asn Val Phe Ser
            180                 185                 190

Cys Ser Val Met His Glu Ala Leu His Asn His Tyr Thr Gln Lys Ser
        195                 200                 205

Leu Ser Leu Ser Leu Gly Lys
    210                 215


<210> SEQ ID NO 13
<211> LENGTH: 306
<212> TYPE: PRT
<213> ORGANISM: Artificial Sequence
<220> FEATURE:
<223> OTHER INFORMATION: mCD80

<400> SEQUENCE: 13

Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
65                  70                  75                  80

Ile Ala Gly Lys Leu Lys Val Trp Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
    210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255
```

```
Ala Val Ile Thr Val Val Val Ile Val Val Ile Ile Lys Cys Phe Cys
            260                 265                 270

Lys His Arg Ser Cys Phe Arg Arg Asn Glu Ala Ser Arg Glu Thr Asn
        275                 280                 285

Asn Ser Leu Thr Phe Gly Pro Glu Glu Ala Leu Ala Glu Gln Thr Val
    290                 295                 300

Phe Leu
305
```

```
<210> SEQ ID NO 14
<211> LENGTH: 1848
<212> TYPE: DNA
<213> ORGANISM: Artificial Sequence
<220> FEATURE:
<223> OTHER INFORMATION: nucleotides coding fusion protein (mGI101)

<400> SEQUENCE: 14

atggatgcta tgctgagagg cctgtgttgc gtgctgctgc tgtgtggcgc tgtgttcgtg     60

tctccttctc acgctgtgga cgagcagctc tccaagtccg tgaaggataa ggtcctgctg    120

ccttgccggt acaactctcc tcacgaggac gagtctgagg accggatcta ctggcagaaa    180

cacgacaagg tggtgctgtc cgtgatcgcc ggaaagctga aagtgtggcc tgagtacaag    240

aacaggaccc tgtacgacaa caccacctac agcctgatca tcctgggcct cgtgctgagc    300

gatagaggca cctattcttg cgtggtgcag aagaaagagc ggggcaccta cgaagtgaag    360

cacctggctc tggtcaagct gtccatcaag gccgacttca gcacccctaa catcaccgag    420

tctggcaacc cttccgccga caccaagaga atcacctgtt tcgcctctgg cggcttccct    480

aagcctcggt tctcttggct ggaaaacggc agagagctgc ccggcatcaa taccaccatt    540

tctcaggacc cagagtccga gctgtacacc atctccagcc agctcgactt taacaccacc    600

agaaaccaca ccatcaagtg cctgattaag tacggcgacg cccacgtgtc cgaggacttt    660

acttgggaga aacctcctga ggaccctcct gactctggat ctggcggcgg aggttctggc    720

ggaggtggaa gcggaggcgg aggatctgct gagtctaagt atggccctcc ttgtcctcca    780

tgtcctgctc cagaagctgc tggcggaccc tctgtgttcc tgtttcctcc aaagcctaag    840

gaccagctca tgatctctcg gacccctgaa gtgacctgcg tggtggtgga tgtgtctcaa    900

gaggaccctg aggtgcagtt caattggtac gtggacggcg tggaagtgca caacgccaag    960

accaagccta gagaggaaca gttcaactcc acctatagag tggtgtccgt gctgaccgtg   1020

ctgcaccagg attggctgaa cggcaaagag tacaagtgca aggtgtccaa caagggcctg   1080

ccttccagca tcgaaaagac catcagcaag gctaagggcc agcctaggga accccaggtt   1140

tacaccctgc ctccaagcca agaggaaatg accaagaacc aggtgtccct gacctgcctg   1200

gtcaagggct tctacccttc cgacattgcc gtggaatggg agtccaatgg ccagcctgag   1260

aacaactaca agaccacacc tcctgtgctg gactccgacg gctccttctt tctgtactct   1320

cgcctgaccg tggacaagtc taggtggcaa gagggcaacg tgttctcctg ctctgtgctg   1380

cacgaggctc tgcacaacca ctacacccag aagtccctgt ctctgtctct tggaggtggt   1440

ggcggttctg cccctacctc cagctctacc aagaaaaccc agctccagtt ggagcatctg   1500

ctgctggacc tccagatgat cctgaatggc atcaacaatt acaagaaccc caagctgacc   1560

gccatgctga ccgctaagtt ctacatgccc aagaaggcca ccgagctgaa gcacttgcag   1620

tgcctggaag aggaactgaa gcccctggaa gaagtgctga atctggccca gtccaagaac   1680
```

```
ttccacctga ggcctaggga cctgatctcc aacatcaacg tgatcgtgct ggaactgaaa   1740

ggctccgaga caaccttcat gtgcgagtac gccgacgaga cagccaccat cgtggaattt   1800

ctgaaccggt ggatcacctt ctgccagagc atcatctcca cactgacc                1848


<210> SEQ ID NO 15
<211> LENGTH: 616
<212> TYPE: PRT
<213> ORGANISM: Artificial Sequence
<220> FEATURE:
<223> OTHER INFORMATION: fusion protein (mGI101)

<400> SEQUENCE: 15

Met Asp Ala Met Leu Arg Gly Leu Cys Cys Val Leu Leu Leu Cys Gly
1               5                   10                  15

Ala Val Phe Val Ser Pro Ser His Ala Val Asp Glu Gln Leu Ser Lys
            20                  25                  30

Ser Val Lys Asp Lys Val Leu Leu Pro Cys Arg Tyr Asn Ser Pro His
        35                  40                  45

Glu Asp Glu Ser Glu Asp Arg Ile Tyr Trp Gln Lys His Asp Lys Val
    50                  55                  60

Val Leu Ser Val Ile Ala Gly Lys Leu Lys Val Trp Pro Glu Tyr Lys
65                  70                  75                  80

Asn Arg Thr Leu Tyr Asp Asn Thr Thr Tyr Ser Leu Ile Ile Leu Gly
                85                  90                  95

Leu Val Leu Ser Asp Arg Gly Thr Tyr Ser Cys Val Val Gln Lys Lys
            100                 105                 110

Glu Arg Gly Thr Tyr Glu Val Lys His Leu Ala Leu Val Lys Leu Ser
        115                 120                 125

Ile Lys Ala Asp Phe Ser Thr Pro Asn Ile Thr Glu Ser Gly Asn Pro
    130                 135                 140

Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
                165                 170                 175

Asn Thr Thr Ile Ser Gln Asp Pro Glu Ser Glu Leu Tyr Thr Ile Ser
            180                 185                 190

Ser Gln Leu Asp Phe Asn Thr Thr Arg Asn His Thr Ile Lys Cys Leu
        195                 200                 205

Ile Lys Tyr Gly Asp Ala His Val Ser Glu Asp Phe Thr Trp Glu Lys
    210                 215                 220

Pro Pro Glu Asp Pro Pro Asp Ser Gly Ser Gly Gly Gly Gly Ser Gly
225                 230                 235                 240

Gly Gly Gly Ser Gly Gly Gly Gly Ser Ala Glu Ser Lys Tyr Gly Pro
                245                 250                 255

Pro Cys Pro Pro Cys Pro Ala Pro Glu Ala Ala Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335
```

```
Val Leu Thr Val Leu His Gln Asp Trp Leu Asn Gly Lys Glu Tyr Lys
            340                 345                 350

Cys Lys Val Ser Asn Lys Gly Leu Pro Ser Ser Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
        435                 440                 445

Trp Gln Glu Gly Asn Val Phe Ser Cys Ser Val Leu His Glu Ala Leu
    450                 455                 460

His Asn His Tyr Thr Gln Lys Ser Leu Ser Leu Ser Leu Gly Gly Gly
465                 470                 475                 480

Gly Gly Ser Ala Pro Thr Ser Ser Ser Thr Lys Lys Thr Gln Leu Gln
                485                 490                 495

Leu Glu His Leu Leu Leu Asp Leu Gln Met Ile Leu Asn Gly Ile Asn
            500                 505                 510

Asn Tyr Lys Asn Pro Lys Leu Thr Ala Met Leu Thr Ala Lys Phe Tyr
        515                 520                 525

Met Pro Lys Lys Ala Thr Glu Leu Lys His Leu Gln Cys Leu Glu Glu
    530                 535                 540

Glu Leu Lys Pro Leu Glu Glu Val Leu Asn Leu Ala Gln Ser Lys Asn
545                 550                 555                 560

Phe His Leu Arg Pro Arg Asp Leu Ile Ser Asn Ile Asn Val Ile Val
                565                 570                 575

Leu Glu Leu Lys Gly Ser Glu Thr Thr Phe Met Cys Glu Tyr Ala Asp
            580                 585                 590

Glu Thr Ala Thr Ile Val Glu Phe Leu Asn Arg Trp Ile Thr Phe Cys
        595                 600                 605

Gln Ser Ile Ile Ser Thr Leu Thr
    610                 615


<210> SEQ ID NO 16
<211> LENGTH: 1437
<212> TYPE: DNA
<213> ORGANISM: Artificial Sequence
<220> FEATURE:
<223> OTHER INFORMATION: nucleotides coding fusion protein (GI101C1)

<400> SEQUENCE: 16

atggatgcta tgctgagagg cctgtgttgc gtgctgctgc tgtgtggcgc tgtgttcgtg     60

tctccttctc acgctgtgat ccacgtgacc aaagaagtga aagaggtcgc cacactgtcc    120

tgcggccaca acgtttcagt ggaagaactg gcccagacca ggatctactg gcagaaagaa    180

aagaaaatgg tgctgaccat gatgtccggc gacatgaaca tctggcctga gtacaagaac    240

cggaccatct tcgacatcac caacaacctg tccatcgtga ttctggccct gaggccttct    300

gatgagggca cctatgagtg cgtggtgctg aagtacgaga aggacgcctt caagcgcgag    360

cacctggctg aagtgacact gtccgtgaag gccgactttc ccacaccttc catctccgac    420

ttcgagatcc ctacctccaa catccggcgg atcatctgtt ctacctctgg cggctttcct    480
```

```
gagcctcacc tgtcttggct ggaaaacggc gaggaactga acgccatcaa caccaccgtg    540

tctcaggacc ccgaaaccga gctgtacgct gtgtcctcca agctggactt caacatgacc    600

accaaccaca gcttcatgtg cctgattaag tacggccacc tgagagtgaa ccagaccttc    660

aactggaaca ccaccaagca agagcacttc cctgacaatg gatctggcgg cggaggttct    720

ggcggaggtg gaagcggagg cggaggatct gctgagtcta agtatggccc tccttgtcct    780

ccatgtcctg ctccagaagc tgctggcgga ccctctgtgt tcctgtttcc tccaaagcct    840

aaggaccagc tcatgatctc tcggacaccc gaagtgacct gcgtggtggt ggatgtgtct    900

caagaggacc ctgaggtgca gttcaattgg tacgtggacg gcgtggaagt gcacaacgcc    960

aagaccaagc ctagagagga acagttcaac tccacctaca gagtggtgtc cgtgctgacc   1020

gtgctgcacc aggattggct gaacggcaaa gagtacaagt gcaaggtgtc caacaagggc   1080

ctgccttcca gcatcgaaaa gaccatctcc aaggctaagg gccagcctag ggaaccccag   1140

gtttacaccc tgcctccaag ccaagaggaa atgaccaaga accaggtgtc cctgacctgc   1200

ctggtcaagg gcttctaccc ttccgacatt gccgtggaat gggagtccaa tggccagcct   1260

gagaacaact acaagaccac acctcctgtg ctggactccg acggctcctt ctttctgtac   1320

tctcgcctga ccgtggacaa gtctaggtgg caagagggca acgtgttctc ctgctctgtg   1380

ctgcacgagg ccctgcacaa tcactacacc cagaagtccc tgtctctgtc cctgggc      1437
```

<210> SEQ ID NO 17
<211> LENGTH: 454
<212> TYPE: PRT
<213> ORGANISM: Artificial Sequence
<220> FEATURE:
<223> OTHER INFORMATION: fusion protein (GI101C1)

<400> SEQUENCE: 17

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190
```

```
Gln Thr Phe Asn Trp Asn Thr Thr Lys Gln Glu His Phe Pro Asp Asn
        195                 200                 205

Gly Ser Gly Gly Gly Gly Ser Gly Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly
    450
```

<210> SEQ ID NO 18
<211> LENGTH: 1176
<212> TYPE: DNA
<213> ORGANISM: Artificial Sequence
<220> FEATURE:
<223> OTHER INFORMATION: nucleotides coding fusion protein (GI101C2)

<400> SEQUENCE: 18

```
atggatgcta tgctgagagg cctgtgttgc gtgctgctgc tgtgtggcgc tgtgttcgtg      60

tctccatctc acgccgctga gtctaagtac ggccctcctt gtcctccatg tcctgctcca     120

gaagctgctg gcggaccctc tgtgttcctg tttcctccaa agcctaagga ccagctcatg     180

atctctcgga cccctgaagt gacctgcgtg gtggtggatg tgtctcaaga ggaccctgag     240

gtgcagttca attggtacgt ggacggcgtg gaagtgcaca acgccaagac caagcctaga     300

gaggaacagt tcaactccac ctacagagtg gtgtccgtgc tgaccgtgct gcaccaggat     360

tggctgaacg gcaaagagta caagtgcaag gtgtccaaca agggcctgcc ttccagcatc     420

gaaaagacca tctccaaggc taagggccag cctagggaac cccaggttta caccctgcct     480

ccaagccaag aggaaatgac caagaaccag gtgtccctga cctgcctggt caagggcttc     540
```

```
tacccttccg acattgccgt ggaatgggag tccaatggcc agcctgagaa caactacaag    600

accacacctc ctgtgctgga ctccgacggc tccttctttc tgtactctcg cctgaccgtg    660

gacaagtcta ggtggcaaga gggcaacgtg ttctcctgct ctgtgctgca cgaggccctg    720

cacaatcact acacccagaa gtccctgtct ctgtctcttg gcggaggcgg aggatctgct    780

cctacctcca gctccaccaa gaaaacccag ctccagttgg agcatctgct gctggacctc    840

cagatgatcc tgaatggcat caacaattac aagaacccca agctgaccgc catgctgacc    900

gctaagttct acatgcccaa gaaggccacc gagctgaagc acctccagtg cctggaagag    960

gaactgaagc ccctggaaga agtgctgaat ctggcccagt ccaagaactt ccacctgagg   1020

cctagggacc tgatctccaa catcaacgtg atcgtgctgg aactgaaagg ctccgagaca   1080

accttcatgt gcgagtacgc cgacgagaca gccaccatcg tggaatttct gaaccggtgg   1140

atcaccttct gccagtccat catctccaca ctgacc                             1176
```

<210> SEQ ID NO 19
<211> LENGTH: 367
<212> TYPE: PRT
<213> ORGANISM: Artificial Sequence
<220> FEATURE:
<223> OTHER INFORMATION: fusion protein (GI101C2)

<400> SEQUENCE: 19

```
Ala Glu Ser Lys Tyr Gly Pro Pro Cys Pro Pro Cys Pro Ala Pro Glu
1               5                   10                  15

Ala Ala Gly Gly Pro Ser Val Phe Leu Phe Pro Pro Lys Pro Lys Asp
            20                  25                  30

Gln Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Leu His Glu Ala Leu His Asn His Tyr Thr Gln Lys Ser Leu
    210                 215                 220

Ser Leu Ser Leu Gly Gly Gly Gly Gly Ser Ala Pro Thr Ser Ser Ser
225                 230                 235                 240

Thr Lys Lys Thr Gln Leu Gln Leu Glu His Leu Leu Leu Asp Leu Gln
                245                 250                 255
```

```
Met Ile Leu Asn Gly Ile Asn Asn Tyr Lys Asn Pro Lys Leu Thr Ala
            260                 265                 270

Met Leu Thr Ala Lys Phe Tyr Met Pro Lys Lys Ala Thr Glu Leu Lys
        275                 280                 285

His Leu Gln Cys Leu Glu Glu Glu Leu Lys Pro Leu Glu Glu Val Leu
    290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
            340                 345                 350

Asn Arg Trp Ile Thr Phe Cys Gln Ser Ile Ile Ser Thr Leu Thr
        355                 360                 365
```

<210> SEQ ID NO 20
<211> LENGTH: 1434
<212> TYPE: DNA
<213> ORGANISM: Artificial Sequence
<220> FEATURE:
<223> OTHER INFORMATION: nucleotides coding fusion protein (mGI101C1)

<400> SEQUENCE: 20

```
atggatgcta tgctgagagg cctgtgttgc gtgctgctgc tgtgtggcgc tgtgttcgtg      60

tctccttctc acgctgtgga cgagcagctc tccaagtccg tgaaggataa ggtcctgctg     120

ccttgccggt acaactctcc tcacgaggac gagtctgagg accggatcta ctggcagaaa     180

cacgacaagg tggtgctgtc cgtgatcgcc ggaaagctga aagtgtggcc tgagtacaag     240

aacaggaccc tgtacgacaa caccacctac agcctgatca tcctgggcct cgtgctgagc     300

gatagaggca cctattcttg cgtggtgcag aagaaagagc ggggcaccta cgaagtgaag     360

cacctggctc tggtcaagct gtccatcaag gccgacttca gcacccctaa catcaccgag     420

tctggcaacc cttccgccga caccaagaga atcacctgtt tcgcctctgg cggcttccct     480

aagcctcggt tctcttggct ggaaaacggc agagagctgc ccggcatcaa taccaccatt     540

tctcaggacc cagagtccga gctgtacacc atctccagcc agctcgactt taacaccacc     600

agaaaccaca ccatcaagtg cctgattaag tacggcgacg cccacgtgtc cgaggacttt     660

acttgggaga aacctcctga ggaccctcct gactctggat ctggcggcgg aggttctggc     720

ggaggtggaa gcggaggcgg aggatctgct gagtctaagt atggccctcc ttgtcctcca     780

tgtcctgctc cagaagctgc tggcggaccc tctgtgttcc tgtttcctcc aaagcctaag     840

gaccagctca tgatctctcg gacccctgaa gtgacctgcg tggtggtgga tgtgtctcaa     900

gaggaccctg aggtgcagtt caattggtac gtggacggcg tggaagtgca caacgccaag     960

accaagccta gagaggaaca gttcaactcc acctatagag tggtgtccgt gctgaccgtg    1020

ctgcaccagg attggctgaa cggcaaagag tacaagtgca aggtgtccaa caagggcctg    1080

ccttccagca tcgaaaagac catcagcaag gctaagggcc agcctaggga accccaggtt    1140

tacaccctgc ctccaagcca agaggaaatg accaagaacc aggtgtccct gacctgcctg    1200

gtcaagggct tctacccttc cgacattgcc gtggaatggg agtccaatgg ccagcctgag    1260

aacaactaca agaccacacc tcctgtgctg gactccgacg gctccttctt tctgtactct    1320

cgcctgaccg tggacaagtc taggtggcaa gagggcaacg tgttctcctg ctctgtgctg    1380

cacgaggctc tgcacaacca ctacacccag aagtccctgt ctctgtccct gggc          1434
```

<210> SEQ ID NO 21
<211> LENGTH: 478
<212> TYPE: PRT
<213> ORGANISM: Artificial Sequence
<220> FEATURE:
<223> OTHER INFORMATION: fusion protein (mGI101C1)

<400> SEQUENCE: 21

```
Met Asp Ala Met Leu Arg Gly Leu Cys Cys Val Leu Leu Leu Cys Gly
1               5                   10                  15

Ala Val Phe Val Ser Pro Ser His Ala Val Asp Glu Gln Leu Ser Lys
            20                  25                  30

Ser Val Lys Asp Lys Val Leu Leu Pro Cys Arg Tyr Asn Ser Pro His
        35                  40                  45

Glu Asp Glu Ser Glu Asp Arg Ile Tyr Trp Gln Lys His Asp Lys Val
    50                  55                  60

Val Leu Ser Val Ile Ala Gly Lys Leu Lys Val Trp Pro Glu Tyr Lys
65                  70                  75                  80

Asn Arg Thr Leu Tyr Asp Asn Thr Thr Tyr Ser Leu Ile Ile Leu Gly
                85                  90                  95

Leu Val Leu Ser Asp Arg Gly Thr Tyr Ser Cys Val Val Gln Lys Lys
            100                 105                 110

Glu Arg Gly Thr Tyr Glu Val Lys His Leu Ala Leu Val Lys Leu Ser
        115                 120                 125

Ile Lys Ala Asp Phe Ser Thr Pro Asn Ile Thr Glu Ser Gly Asn Pro
    130                 135                 140

Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
                165                 170                 175

Asn Thr Thr Ile Ser Gln Asp Pro Glu Ser Glu Leu Tyr Thr Ile Ser
            180                 185                 190

Ser Gln Leu Asp Phe Asn Thr Thr Arg Asn His Thr Ile Lys Cys Leu
        195                 200                 205

Ile Lys Tyr Gly Asp Ala His Val Ser Glu Asp Phe Thr Trp Glu Lys
    210                 215                 220

Pro Pro Glu Asp Pro Pro Asp Ser Gly Ser Gly Gly Gly Gly Ser Gly
225                 230                 235                 240

Gly Gly Gly Ser Gly Gly Gly Gly Ser Ala Glu Ser Lys Tyr Gly Pro
                245                 250                 255

Pro Cys Pro Pro Cys Pro Ala Pro Glu Ala Ala Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Gly Leu Pro Ser Ser Ile Glu Lys Thr Ile
        355                 360                 365
```

Ser Lys Ala Lys Gly Gln Pro Arg Glu Pro Gln Val Tyr Thr Leu Pro
370 375 380

Pro Ser Gln Glu Glu Met Thr Lys Asn Gln Val Ser Leu Thr Cys Leu
385 390 395 400

Val Lys Gly Phe Tyr Pro Ser Asp Ile Ala Val Glu Trp Glu Ser Asn
405 410 415

Gly Gln Pro Glu Asn Asn Tyr Lys Thr Thr Pro Pro Val Leu Asp Ser
420 425 430

Asp Gly Ser Phe Phe Leu Tyr Ser Arg Leu Thr Val Asp Lys Ser Arg
435 440 445

Trp Gln Glu Gly Asn Val Phe Ser Cys Ser Val Leu His Glu Ala Leu
450 455 460

His Asn His Tyr Thr Gln Lys Ser Leu Ser Leu Ser Leu Gly
465 470 475

<210> SEQ ID NO 22
<211> LENGTH: 133
<212> TYPE: PRT
<213> ORGANISM: Artificial Sequence
<220> FEATURE:
<223> OTHER INFORMATION: variants of IL-2 (3M, M45)

<400> SEQUENCE: 22

Ala Pro Thr Ser Ser Ser Thr Lys Lys Thr Gln Leu Gln Leu Glu His
1 5 10 15

Leu Leu Leu Asp Leu Gln Met Ile Leu Asn Gly Ile Asn Asn Tyr Lys
20 25 30

Asn Pro Lys Leu Thr Ala Met Leu Thr Ala Lys Phe Ala Met Pro Lys
35 40 45

Lys Ala Thr Glu Leu Lys His Leu Gln Cys Leu Glu Glu Glu Leu Lys
50 55 60

Pro Leu Glu Glu Val Leu Asn Leu Ala Gln Ser Lys Asn Phe His Leu
65 70 75 80

Arg Pro Arg Asp Leu Ile Ser Asn Ile Asn Val Ile Val Leu Glu Leu
85 90 95

Lys Gly Ser Glu Thr Thr Phe Met Cys Glu Tyr Ala Asp Glu Thr Ala
100 105 110

Thr Ile Val Glu Phe Leu Asn Arg Trp Ile Thr Phe Cys Gln Ser Ile
115 120 125

Ile Ser Thr Leu Thr
130

<210> SEQ ID NO 23
<211> LENGTH: 133
<212> TYPE: PRT
<213> ORGANISM: Artificial Sequence
<220> FEATURE:
<223> OTHER INFORMATION: variants of IL-2 (3M, M61)

<400> SEQUENCE: 23

Ala Pro Thr Ser Ser Ser Thr Lys Lys Thr Gln Leu Gln Leu Glu His
1 5 10 15

Leu Leu Leu Asp Leu Gln Met Ile Leu Asn Gly Ile Asn Asn Tyr Lys
20 25 30

Asn Pro Lys Leu Thr Ala Met Leu Thr Ala Lys Phe Tyr Met Pro Lys
35 40 45

Lys Ala Thr Glu Leu Lys His Leu Gln Cys Leu Glu Arg Glu Leu Lys

```
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 24
<211> LENGTH: 133
<212> TYPE: PRT
<213> ORGANISM: Artificial Sequence
<220> FEATURE:
<223> OTHER INFORMATION: variants of IL-2 (3M, M72)

<400> SEQUENCE: 24

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 25
<211> LENGTH: 1851
<212> TYPE: DNA
<213> ORGANISM: Artificial Sequence
<220> FEATURE:
<223> OTHER INFORMATION: nucleotides coding fusion protein (GI102-M45)

<400> SEQUENCE: 25

atggatgcta tgctgagagg cctgtgttgc gtgctgctgc tgtgtggcgc tgtgttcgtg     60

tctccttctc acgctgtgat ccacgtgacc aaagaagtga aagaggtcgc cacactgtcc    120

tgcggccaca acgtttcagt ggaagaactg gcccagacca ggatctactg gcagaaagaa    180

aagaaaatgg tgctgaccat gatgtccggc gacatgaaca tctggcctga gtacaagaac    240

cggaccatct tcgacatcac caacaacctg tccatcgtga ttctggccct gaggccttct    300

gatgagggca cctatgagtg cgtggtgctg aagtacgaga aggacgcctt caagcgcgag    360

cacctggctg aagtgacact gtccgtgaag gccgactttc ccacaccttc catctccgac    420

ttcgagatcc ctacctccaa catccggcgg atcatctgtt ctacctctgg cggctttcct    480
```

```
gagcctcacc tgtcttggct ggaaaacggc gaggaactga acgccatcaa caccaccgtg    540

tctcaggacc ccgaaaccga gctgtacgct gtgtcctcca agctggactt caacatgacc    600

accaaccaca gcttcatgtg cctgattaag tacggccacc tgagagtgaa ccagaccttc    660

aactggaaca ccaccaagca agagcacttc cctgacaatg gatctggcgg cggaggttct    720

ggcggaggtg gaagcggagg cggaggatct gctgagtcta agtatggccc tccttgtcct    780

ccatgtcctg ctccagaagc tgctggcgga ccctctgtgt tcctgtttcc tccaaagcct    840

aaggaccagc tcatgatctc tcggacaccc gaagtgacct gcgtggtggt ggatgtgtct    900

caagaggacc ctgaggtgca gttcaattgg tacgtggacg gcgtggaagt gcacaacgcc    960

aagaccaagc ctagagagga acagttcaac tccacctaca gagtggtgtc cgtgctgacc   1020

gtgctgcacc aggattggct gaacggcaaa gagtacaagt gcaaggtgtc caacaagggc   1080

ctgccttcca gcatcgaaaa gaccatctcc aaggctaagg gccagcctag ggaaccccag   1140

gtttacaccc tgcctccaag ccaagaggaa atgaccaaga accaggtgtc cctgacctgc   1200

ctggtcaagg gcttctaccc ttccgacatt gccgtggaat gggagtccaa tggccagcct   1260

gagaacaact acaagaccac acctcctgtg ctggactccg acggctcctt ctttctgtac   1320

tctcgcctga ccgtggacaa gtctagatgg caagagggca acgtgttctc ctgctctgtg   1380

ctgcacgagg ccctgcacaa tcactacacc cagaagtccc tgtctctgtc tcttggaggt   1440

ggtggcggtt ctgcccctac cagctcctct accaagaaaa cccagctcca gttggagcat   1500

ctgctgctgg acctccagat gattctgaac gggatcaaca actataagaa ccccaagctg   1560

accgccatgc tgaccgctaa gttcgccatg cccaagaagg ccaccgagct gaagcacctc   1620

cagtgcctgg aagaagaact gaagcccctg gaagaggtgc tgaatctggc ccagtccaag   1680

aacttccacc tgaggccacg ggacctgatc agcaacatca acgtgatcgt gctggaactg   1740

aagggctccg agacaacctt tatgtgcgag tacgccgacg agacagccac catcgtggaa   1800

tttctgaacc ggtggatcac cttctgccag agcatcatct ccacactgac c             1851
```

<210> SEQ ID NO 26
<211> LENGTH: 592
<212> TYPE: PRT
<213> ORGANISM: Artificial Sequence
<220> FEATURE:
<223> OTHER INFORMATION: fusion protein (GI102-M45)

<400> SEQUENCE: 26

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
```

```
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Ala Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
    530                 535                 540
```

```
Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590


<210> SEQ ID NO 27
<211> LENGTH: 1851
<212> TYPE: DNA
<213> ORGANISM: Artificial Sequence
<220> FEATURE:
<223> OTHER INFORMATION: nucleotides coding fusion protein (GI102-M61)

<400> SEQUENCE: 27

atggatgcta tgctgagagg cctgtgttgc gtgctgctgc tgtgtggcgc tgtgttcgtg     60

tctccttctc acgctgtgat ccacgtgacc aaagaagtga aagaggtcgc cacactgtcc    120

tgcggccaca acgtttcagt ggaagaactg gcccagacca ggatctactg gcagaaagaa    180

aagaaaatgg tgctgaccat gatgtccggc gacatgaaca tctggcctga gtacaagaac    240

cggaccatct tcgacatcac caacaacctg tccatcgtga ttctggccct gaggccttct    300

gatgagggca cctatgagtg cgtggtgctg aagtacgaga aggacgcctt caagcgcgag    360

cacctggctg aagtgacact gtccgtgaag gccgactttc ccacaccttc catctccgac    420

ttcgagatcc ctacctccaa catccggcgg atcatctgtt ctacctctgg cggctttcct    480

gagcctcacc tgtcttggct ggaaaacggc gaggaactga acgccatcaa caccaccgtg    540

tctcaggacc ccgaaaccga gctgtacgct gtgtcctcca agctggactt caacatgacc    600

accaaccaca gcttcatgtg cctgattaag tacggccacc tgagagtgaa ccagaccttc    660

aactggaaca ccaccaagca agagcacttc cctgacaatg gatctggcgg cggaggttct    720

ggcggaggtg gaagcggagg cggaggatct gctgagtcta agtatggccc tccttgtcct    780

ccatgtcctg ctccagaagc tgctggcgga ccctctgtgt tcctgtttcc tccaaagcct    840

aaggaccagc tcatgatctc tcggacaccc gaagtgacct gcgtggtggt ggatgtgtct    900

caagaggacc ctgaggtgca gttcaattgg tacgtggacg gcgtggaagt gcacaacgcc    960

aagaccaagc ctagagagga acagttcaac tccacctaca gagtggtgtc cgtgctgacc   1020

gtgctgcacc aggattggct gaacggcaaa gagtacaagt gcaaggtgtc caacaagggc   1080

ctgccttcca gcatcgaaaa gaccatctcc aaggctaagg gccagcctag ggaaccccag   1140

gtttacaccc tgcctccaag ccaagaggaa atgaccaaga accaggtgtc cctgacctgc   1200

ctggtcaagg gcttctaccc ttccgacatt gccgtggaat gggagtccaa tggccagcct   1260

gagaacaact acaagaccac acctcctgtg ctggactccg acggctcctt ctttctgtac   1320

tctcgcctga ccgtggacaa gtctagatgg caagagggca acgtgttctc ctgctctgtg   1380

ctgcacgagg ccctgcacaa tcactacacc cagaagtccc tgtctctgtc tcttggaggt   1440

ggtggcggtt ctgcccctac cagctcctct accaagaaaa cccagctcca gttggagcat   1500

ctgctgctgg acctccagat gattctgaac gggatcaaca actataagaa ccccaagctg   1560

accgccatgc tgaccgctaa gttctacatg cccaagaagg ccaccgagct gaagcacctc   1620

cagtgcctgg aaagggaact gaagcccctg gaagaggtgc tgaatctggc ccagtccaag   1680

aacttccacc tgaggccacg ggacctgatc agcaacatca acgtgatcgt gctggaactg   1740

aagggctccg agacaacctt tatgtgcgag tacgccgacg agacagccac catcgtggaa   1800
```

tttctgaacc ggtggatcac cttctgccag agcatcatct ccacactgac c 1851

<210> SEQ ID NO 28
<211> LENGTH: 592
<212> TYPE: PRT
<213> ORGANISM: Artificial Sequence
<220> FEATURE:
<223> OTHER INFORMATION: fusion protein (GI102-M61)

<400> SEQUENCE: 28

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Leu Ala Leu Arg Pro Ser Asp Glu Gly Thr Tyr
65 70 75 80

Glu Cys Val Val Leu Lys Tyr Glu Lys Asp Ala Phe Lys Arg Glu His
85 90 95

Leu Ala Glu Val Thr Leu Ser Val Lys Ala Asp Phe Pro Thr Pro Ser
100 105 110

Ile Ser Asp Phe Glu Ile Pro Thr Ser Asn Ile Arg Arg Ile Ile Cys
115 120 125

Ser Thr Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

Gly Ser Gly Gly Gly Gly Ser Gly Gly Gly Gly Ser Gly Gly Gly Gly
210 215 220

Ser Ala Glu Ser Lys Tyr Gly Pro Pro Cys Pro Pro Cys Pro Ala Pro
225 230 235 240

Glu Ala Ala Gly Gly Pro Ser Val Phe Leu Phe Pro Pro Lys Pro Lys
245 250 255

Asp Gln Leu Met Ile Ser Arg Thr Pro Glu Val Thr Cys Val Val Val
260 265 270

Asp Val Ser Gln Glu Asp Pro Glu Val Gln Phe Asn Trp Tyr Val Asp
275 280 285

Gly Val Glu Val His Asn Ala Lys Thr Lys Pro Arg Glu Glu Gln Phe
290 295 300

Asn Ser Thr Tyr Arg Val Val Ser Val Leu Thr Val Leu His Gln Asp
305 310 315 320

Trp Leu Asn Gly Lys Glu Tyr Lys Cys Lys Val Ser Asn Lys Gly Leu
325 330 335

Pro Ser Ser Ile Glu Lys Thr Ile Ser Lys Ala Lys Gly Gln Pro Arg
340 345 350

```
Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Tyr Met Pro Lys Lys Ala Thr Glu Leu
            500                 505                 510

Lys His Leu Gln Cys Leu Glu Arg Glu Leu Lys Pro Leu Glu Glu Val
        515                 520                 525

Leu Asn Leu Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590


<210> SEQ ID NO 29
<211> LENGTH: 1857
<212> TYPE: DNA
<213> ORGANISM: Artificial Sequence
<220> FEATURE:
<223> OTHER INFORMATION: nucleotides coding fusion protein (GI102-M72)

<400> SEQUENCE: 29

atggatgcta tgctgagagg cctgtgttgc gtgctgctgc tgtgtggcgc tgtgttcgtg      60

tctccttctc acgctgtgat ccacgtgacc aaagaagtga aagaggtcgc cacactgtcc     120

tgcggccaca acgtttcagt ggaagaactg gcccagacca ggatctactg gcagaaagaa     180

aagaaaatgg tgctgaccat gatgtccggc gacatgaaca tctggcctga gtacaagaac     240

cggaccatct tcgacatcac caacaacctg tccatcgtga ttctggccct gaggccttct     300

gatgagggca cctatgagtg cgtggtgctg aagtacgaga aggacgcctt caagcgcgag     360

cacctggctg aagtgacact gtccgtgaag gccgactttc ccacaccttc catctccgac     420

ttcgagatcc ctacctccaa catccggcgg atcatctgtt ctacctctgg cggctttcct     480

gagcctcacc tgtcttggct ggaaaacggc gaggaactga acgccatcaa caccaccgtg     540

tctcaggacc ccgaaaccga gctgtacgct gtgtcctcca agctggactt caacatgacc     600

accaaccaca gcttcatgtg cctgattaag tacggccacc tgagagtgaa ccagaccttc     660

aactggaaca ccaccaagca agagcacttc cctgacaatg gatctggcgg cggaggttct     720
```

-continued

```
ggcggaggtg gaagcggagg cggaggatct gctgagtcta agtatggccc tccttgtcct    780

ccatgtcctg ctccagaagc tgctggcgga ccctctgtgt tcctgtttcc tccaaagcct    840

aaggaccagc tcatgatctc tcggacaccc gaagtgacct gcgtggtggt ggatgtgtct    900

caagaggacc ctgaggtgca gttcaattgg tacgtggacg gcgtggaagt gcacaacgcc    960

aagaccaagc ctagagagga acagttcaac tccacctaca gagtggtgtc cgtgctgacc   1020

gtgctgcacc aggattggct gaacggcaaa gagtacaagt gcaaggtgtc caacaagggc   1080

ctgccttcca gcatcgaaaa gaccatctcc aaggctaagg gccagcctag ggaaccccag   1140

gtttacaccc tgcctccaag ccaagaggaa atgaccaaga accaggtgtc cctgacctgc   1200

ctggtcaagg gcttctaccc ttccgacatt gccgtggaat gggagtccaa tggccagcct   1260

gagaacaact acaagaccac acctcctgtg ctggactccg acggctcctt ctttctgtac   1320

tctcgcctga ccgtggacaa gtctagatgg caagagggca acgtgttctc ctgctctgtg   1380

ctgcacgagg ccctgcacaa tcactacacc cagaagtccc tgtctctgtc tcttggaggt   1440

ggtggcggtt ctgcccctac cagctcctct accaagaaaa cccagctcca gttggagcat   1500

ctgctgctgg acctccagat gattctgaac gggatcaaca actataagaa ccccaagctg   1560

accgccatgc tgaccgctaa gttctacatg cccaagaagg ccaccgagct gaagcacctc   1620

cagtgcctgg aagaagaact gaagcccctg gaagaggtgc tgaatggggc ccagtccaag   1680

aacttccacc tgaggccacg ggacctgatc agcaacatca acgtgatcgt gctggaactg   1740

aagggctccg agacaacctt tatgtgcgag tacgccgacg agacagccac catcgtggaa   1800

tttctgaacc ggtggatcac cttctgccag agcatcatct ccacactgac ctgatga      1857
```

```
<210> SEQ ID NO 30
<211> LENGTH: 592
<212> TYPE: PRT
<213> ORGANISM: Artificial Sequence
<220> FEATURE:
<223> OTHER INFORMATION: fusion protein (GI102-M72)

<400> SEQUENCE: 30

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
```

```
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Gly Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590
```

<210> SEQ ID NO 31
<211> LENGTH: 1851
<212> TYPE: DNA
<213> ORGANISM: Artificial Sequence
<220> FEATURE:
<223> OTHER INFORMATION: nucleotides coding fusion protein (GI101w)

<400> SEQUENCE: 31

```
atggatgcta tgctgagagg cctgtgttgc gtgctgctgc tgtgtggcgc tgtgttcgtg     60
tctccttctc acgctgtgat ccacgtgacc aaagaagtga aagaggtcgc cacactgtcc    120
tgcggccaca acgtttcagt ggaagaactg gcccagacca ggatctactg gcagaaagaa    180
aagaaaatgg tgctgaccat gatgtccggc gacatgaaca tctggcctga gtacaagaac    240
cggaccatct tcgacatcac caacaacctg tccatcgtga ttctggccct gaggccttct    300
gatgagggca cctatgagtg cgtggtgctg aagtacgaga aggacgcctt caagcgcgag    360
cacctggctg aagtgacact gtccgtgaag gccgactttc ccacaccttc catctccgac    420
ttcgagatcc ctacctccaa catccggcgg atcatctgtt ctacctctgg cggctttcct    480
gagcctcacc tgtcttggct ggaaaacggc gaggaactga acgccatcaa caccaccgtg    540
tctcaggacc ccgaaaccga gctgtacgct gtgtcctcca agctggactt caacatgacc    600
accaaccaca gcttcatgtg cctgattaag tacggccacc tgagagtgaa ccagaccttc    660
aactggaaca ccaccaagca agagcacttc cctgacaatg gatctggcgg cggaggttct    720
ggcggaggtg gaagcggagg cggaggatct gctgagtcta agtatggccc tccttgtcct    780
ccatgtcctg ctccagaagc tgctggcgga ccctctgtgt tcctgtttcc tccaaagcct    840
aaggaccagc tcatgatctc tcggacaccc gaagtgacct gcgtggtggt ggatgtgtct    900
caagaggacc ctgaggtgca gttcaattgg tacgtggacg gcgtggaagt gcacaacgcc    960
aagaccaagc ctagagagga acagttcaac tccacctaca gagtggtgtc cgtgctgacc   1020
gtgctgcacc aggattggct gaacggcaaa gagtacaagt gcaaggtgtc caacaagggc   1080
ctgccttcca gcatcgaaaa gaccatctcc aaggctaagg gccagcctag ggaaccccag   1140
gtttacaccc tgcctccaag ccaagaggaa atgaccaaga accaggtgtc cctgacctgc   1200
ctggtcaagg gcttctaccc ttccgacatt gccgtggaat gggagtccaa tggccagcct   1260
gagaacaact acaagaccac acctcctgtg ctggactccg acggctcctt ctttctgtac   1320
tctcgcctga ccgtggacaa gtctagatgg caagagggca acgtgttctc ctgctctgtg   1380
ctgcacgagg ccctgcacaa tcactacacc cagaagtccc tgtctctgtc tcttggaggt   1440
ggtggcggtt ctgcccctac cagctcctct accaagaaaa cccagctcca gttggagcat   1500
ctgctgctgg acctccagat gattctgaac gggatcaaca actataagaa ccccaagctg   1560
acccgcatgc tgacctttaa gttctacatg cccaagaagg ccaccgagct gaagcacctc   1620
cagtgcctgg aagaagaact gaagcccctg gaagaggtgc tgaatctggc ccagtccaag   1680
aacttccacc tgaggccacg ggacctgatc agcaacatca acgtgatcgt gctggaactg   1740
aagggctccg agacaacctt tatgtgcgag tacgccgacg agacagccac catcgtggaa   1800
tttctgaacc ggtggatcac cttctgccag agcatcatct ccacactgac c            1851
```

<210> SEQ ID NO 32
<211> LENGTH: 592
<212> TYPE: PRT
<213> ORGANISM: Artificial Sequence
<220> FEATURE:

<223> OTHER INFORMATION: fusion protein (GI101w)

<400> SEQUENCE: 32

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400
```

```
Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Phe Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590
```

<210> SEQ ID NO 33
<211> LENGTH: 1848
<212> TYPE: DNA
<213> ORGANISM: Artificial Sequence
<220> FEATURE:
<223> OTHER INFORMATION: nucleotides coding fusion protein (mGI102-M61)

<400> SEQUENCE: 33

```
atggatgcta tgctgagagg cctgtgttgc gtgctgctgc tgtgtggcgc tgtgttcgtg     60

tctccttctc acgctgtgga cgagcagctc tccaagtccg tgaaggataa ggtcctgctg    120

ccttgccggt acaactctcc tcacgaggac gagtctgagg accggatcta ctggcagaaa    180

cacgacaagg tggtgctgtc cgtgatcgcc ggaaagctga aagtgtggcc tgagtacaag    240

aacaggaccc tgtacgacaa caccacctac agcctgatca tcctgggcct cgtgctgagc    300

gatagaggca cctattcttg cgtggtgcag aagaaagagc ggggcaccta cgaagtgaag    360

cacctggctc tggtcaagct gtccatcaag gccgacttca gcacccctaa catcaccgag    420

tctggcaacc cttccgccga caccaagaga atcacctgtt tcgcctctgg cggcttccct    480

aagcctcggt tctcttggct ggaaaacggc agagagctgc ccggcatcaa taccaccatt    540

tctcaggacc cagagtccga gctgtacacc atctccagcc agctcgactt taacaccacc    600

agaaaccaca ccatcaagtg cctgattaag tacggcgacg cccacgtgtc cgaggacttt    660

acttgggaga aacctcctga ggaccctcct gactctggat ctggcggcgg aggttctggc    720

ggaggtggaa gcggaggcgg aggatctgct gagtctaagt atggccctcc ttgtcctcca    780

tgtcctgctc cagaagctgc tggcggaccc tctgtgttcc tgtttcctcc aaagcctaag    840

gaccagctca tgatctctcg gacccctgaa gtgacctgcg tggtggtgga tgtgtctcaa    900

gaggaccctg aggtgcagtt caattggtac gtggacggcg tggaagtgca caacgccaag    960

accaagccta gagaggaaca gttcaactcc acctatagag tggtgtccgt gctgaccgtg   1020
```

ctgcaccagg attggctgaa cggcaaagag tacaagtgca aggtgtccaa caagggcctg 1080
ccttccagca tcgaaaagac catcagcaag gctaagggcc agcctaggga accccaggtt 1140
tacaccctgc ctccaagcca agaggaaatg accaagaacc aggtgtccct gacctgcctg 1200
gtcaagggct tctacccttc cgacattgcc gtggaatggg agtccaatgg ccagcctgag 1260
aacaactaca agaccacacc tcctgtgctg gactccgacg gctccttctt tctgtactct 1320
cgcctgaccg tggacaagtc taggtggcaa gagggcaacg tgttctcctg ctctgtgctg 1380
cacgaggctc tgcacaacca ctacacccag aagtccctgt ctctgtctct tggaggtggt 1440
ggcggttctg cccctacctc cagctctacc aagaaaaccc agctccagtt ggagcatctg 1500
ctgctggacc tccagatgat cctgaatggc atcaacaatt acaagaaccc caagctgacc 1560
gccatgctga ccgctaagtt ctacatgccc aagaaggcca ccgagctgaa gcacttgcag 1620
tgcctggaaa gggaactgaa gcccctggaa gaagtgctga atctggccca gtccaagaac 1680
ttccacctga ggcctaggga cctgatctcc aacatcaacg tgatcgtgct ggaactgaaa 1740
ggctccgaga caaccttcat gtgcgagtac gccgacgaga cagccaccat cgtggaattt 1800
ctgaaccggt ggatcacctt ctgccagagc atcatctcca cactgacc 1848

<210> SEQ ID NO 34
<211> LENGTH: 616
<212> TYPE: PRT
<213> ORGANISM: Artificial Sequence
<220> FEATURE:
<223> OTHER INFORMATION: fusion protein (mGI102-M61)

<400> SEQUENCE: 34

Met Asp Ala Met Leu Arg Gly Leu Cys Cys Val Leu Leu Leu Cys Gly
1 5 10 15

Ala Val Phe Val Ser Pro Ser His Ala Val Asp Glu Gln Leu Ser Lys
20 25 30

Ser Val Lys Asp Lys Val Leu Leu Pro Cys Arg Tyr Asn Ser Pro His
35 40 45

Glu Asp Glu Ser Glu Asp Arg Ile Tyr Trp Gln Lys His Asp Lys Val
50 55 60

Val Leu Ser Val Ile Ala Gly Lys Leu Lys Val Trp Pro Glu Tyr Lys
65 70 75 80

Asn Arg Thr Leu Tyr Asp Asn Thr Thr Tyr Ser Leu Ile Ile Leu Gly
85 90 95

Leu Val Leu Ser Asp Arg Gly Thr Tyr Ser Cys Val Val Gln Lys Lys
100 105 110

Glu Arg Gly Thr Tyr Glu Val Lys His Leu Ala Leu Val Lys Leu Ser
115 120 125

Ile Lys Ala Asp Phe Ser Thr Pro Asn Ile Thr Glu Ser Gly Asn Pro
130 135 140

Ser Ala Asp Thr Lys Arg Ile Thr Cys Phe Ala Ser Gly Gly Phe Pro
145 150 155 160

Lys Pro Arg Phe Ser Trp Leu Glu Asn Gly Arg Glu Leu Pro Gly Ile
165 170 175

Asn Thr Thr Ile Ser Gln Asp Pro Glu Ser Glu Leu Tyr Thr Ile Ser
180 185 190

Ser Gln Leu Asp Phe Asn Thr Thr Arg Asn His Thr Ile Lys Cys Leu
195 200 205

Ile Lys Tyr Gly Asp Ala His Val Ser Glu Asp Phe Thr Trp Glu Lys

```
    210                 215                 220

Pro Pro Glu Asp Pro Pro Asp Ser Gly Ser Gly Gly Gly Gly Ser Gly
225                 230                 235                 240

Gly Gly Gly Ser Gly Gly Gly Gly Ser Ala Glu Ser Lys Tyr Gly Pro
                245                 250                 255

Pro Cys Pro Pro Cys Pro Ala Pro Glu Ala Ala Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Gly Leu Pro Ser Ser Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
        435                 440                 445

Trp Gln Glu Gly Asn Val Phe Ser Cys Ser Val Leu His Glu Ala Leu
    450                 455                 460

His Asn His Tyr Thr Gln Lys Ser Leu Ser Leu Ser Leu Gly Gly Gly
465                 470                 475                 480

Gly Gly Ser Ala Pro Thr Ser Ser Ser Thr Lys Lys Thr Gln Leu Gln
                485                 490                 495

Leu Glu His Leu Leu Leu Asp Leu Gln Met Ile Leu Asn Gly Ile Asn
            500                 505                 510

Asn Tyr Lys Asn Pro Lys Leu Thr Ala Met Leu Thr Ala Lys Phe Tyr
        515                 520                 525

Met Pro Lys Lys Ala Thr Glu Leu Lys His Leu Gln Cys Leu Glu Arg
    530                 535                 540

Glu Leu Lys Pro Leu Glu Glu Val Leu Asn Leu Ala Gln Ser Lys Asn
545                 550                 555                 560

Phe His Leu Arg Pro Arg Asp Leu Ile Ser Asn Ile Asn Val Ile Val
                565                 570                 575

Leu Glu Leu Lys Gly Ser Glu Thr Thr Phe Met Cys Glu Tyr Ala Asp
            580                 585                 590

Glu Thr Ala Thr Ile Val Glu Phe Leu Asn Arg Trp Ile Thr Phe Cys
        595                 600                 605

Gln Ser Ile Ile Ser Thr Leu Thr
    610                 615
```

<210> SEQ ID NO 35

<211> LENGTH: 153
<212> TYPE: PRT
<213> ORGANISM: Artificial Sequence
<220> FEATURE:
<223> OTHER INFORMATION: wild type hIL-2

<400> SEQUENCE: 35

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 36
<211> LENGTH: 158
<212> TYPE: PRT
<213> ORGANISM: Artificial Sequence
<220> FEATURE:
<223> OTHER INFORMATION: IL-2 with signal sequence

<400> SEQUENCE: 36

```
Met Asp Ala Met Leu Arg Gly Leu Cys Cys Val Leu Leu Leu Cys Gly
1               5                   10                  15

Ala Val Phe Val Ser Pro Ser His Ala Ala Pro Thr Ser Ser Ser Thr
            20                  25                  30

Lys Lys Thr Gln Leu Gln Leu Glu His Leu Leu Leu Asp Leu Gln Met
        35                  40                  45

Ile Leu Asn Gly Ile Asn Asn Tyr Lys Asn Pro Lys Leu Thr Arg Met
    50                  55                  60

Leu Thr Phe Lys Phe Tyr Met Pro Lys Lys Ala Thr Glu Leu Lys His
65                  70                  75                  80

Leu Gln Cys Leu Glu Glu Glu Leu Lys Pro Leu Glu Glu Val Leu Asn
                85                  90                  95

Leu Ala Gln Ser Lys Asn Phe His Leu Arg Pro Arg Asp Leu Ile Ser
            100                 105                 110

Asn Ile Asn Val Ile Val Leu Glu Leu Lys Gly Ser Glu Thr Thr Phe
        115                 120                 125

Met Cys Glu Tyr Ala Asp Glu Thr Ala Thr Ile Val Glu Phe Leu Asn
    130                 135                 140

Arg Trp Ile Thr Phe Cys Gln Ser Ile Ile Ser Thr Leu Thr
145                 150                 155
```

<210> SEQ ID NO 37
<211> LENGTH: 474
<212> TYPE: DNA
<213> ORGANISM: Artificial Sequence
<220> FEATURE:
<223> OTHER INFORMATION: nucleotide sequence coding IL-2 with signal sequence

<400> SEQUENCE: 37

```
atggatgcta tgctgagagg cctgtgttgc gtgctgctgc tgtgtggcgc tgtgttcgtg     60

tctccttctc acgctgcccc taccagctcc tctaccaaga aaacccagct ccagttggag    120

catctgctgc tggacctcca gatgattctg aacgggatca acaactataa gaaccccaag    180

ctgacccgca tgctgacctt taagttctac atgcccaaga aggccaccga gctgaagcac    240

ctccagtgcc tggaagaaga actgaagccc ctggaagagg tgctgaatct ggcccagtcc    300

aagaacttcc acctgaggcc acgggacctg atcagcaaca tcaacgtgat cgtgctggaa    360

ctgaagggct ccgagacaac ctttatgtgc gagtacgccg acgagacagc caccatcgtg    420

gaatttctga accggtggat caccttctgc cagagcatca tctccacact gacc          474
```

<210> SEQ ID NO 38
<211> LENGTH: 13
<212> TYPE: PRT
<213> ORGANISM: Artificial Sequence
<220> FEATURE:
<223> OTHER INFORMATION: hinge

<400> SEQUENCE: 38

```
Ala Glu Ser Lys Tyr Gly Pro Pro Cys Pro Pro Cys Pro
1               5                   10
```

<210> SEQ ID NO 39
<211> LENGTH: 1461
<212> TYPE: DNA
<213> ORGANISM: Artificial Sequence
<220> FEATURE:
<223> OTHER INFORMATION: nucleotides coding CD80-Fc protein

<400> SEQUENCE: 39

```
ggatccgcca ccatggatgc tatgctgaga ggcctgtgtt gcgtgctgct gctgtgtggc     60

gctgtgttcg tgtctccttc tcacgctgtg atccacgtga ccaaagaagt gaaagaggtc    120

gccacactgt cctgcggcca caacgtttca gtggaagaac tggcccagac caggatctac    180

tggcagaaag aaaagaaaat ggtgctgacc atgatgtccg gcgacatgaa catctggcct    240

gagtacaaga accggaccat cttcgacatc accaacaacc tgtccatcgt gattctggcc    300

ctgaggcctt ctgatgaggg cacctatgag tgcgtggtgc tgaagtacga gaaggacgcc    360

ttcaagcgcg agcacctggc tgaagtgaca ctgtccgtga aggccgactt tcccacacct    420

tccatctccg acttcgagat ccctacctcc aacatccggc ggatcatctg ttctacctct    480

ggcggctttc ctgagcctca cctgtcttgg ctggaaaacg gcgaggaact gaacgccatc    540

aacaccaccg tgtctcagga ccccgaaacc gagctgtacg ctgtgtcctc caagctggac    600

ttcaacatga ccaccaacca cagcttcatg tgcctgatta agtacggcca cctgagagtg    660

aaccagacct tcaactggaa caccaccaag caagagcact tccctgacaa tggatctggc    720

ggcggaggtt ctggcggagg tggaagcgga ggcggaggat ctgctgagtc taagtatggc    780

cctccttgtc ctccatgtcc tgctccagaa gctgctggcg gaccctctgt gttcctgttt    840

cctccaaagc ctaaggacca gctcatgatc tctcggacac ccgaagtgac ctgcgtggtg    900
```

```
gtggatgtgt ctcaagagga ccctgaggtg cagttcaatt ggtacgtgga cggcgtggaa    960

gtgcacaacg ccaagaccaa gcctagagag gaacagttca actccaccta cagagtggtg   1020

tccgtgctga ccgtgctgca ccaggattgg ctgaacggca aagagtacaa gtgcaaggtg   1080

tccaacaagg gcctgccttc cagcatcgaa aagaccatct ccaaggctaa gggccagcct   1140

agggaacccc aggtttacac cctgcctcca agccaagagg aaatgaccaa gaaccaggtg   1200

tccctgacct gcctggtcaa gggcttctac ccttccgaca ttgccgtgga atgggagtcc   1260

aatggccagc ctgagaacaa ctacaagacc acacctcctg tgctggactc cgacggctcc   1320

ttctttctgt actctcgcct gaccgtggac aagtctaggt ggcaagaggg caacgtgttc   1380

tcctgctctg tgctgcacga ggccctgcac aatcactaca cccagaagtc cctgtctctg   1440

tccctgggct gatgactcga g                                              1461


<210> SEQ ID NO 40
<211> LENGTH: 479
<212> TYPE: PRT
<213> ORGANISM: Artificial Sequence
<220> FEATURE:
<223> OTHER INFORMATION: CD80-Fc protein

<400> SEQUENCE: 40

Met Asp Ala Met Leu Arg Gly Leu Cys Cys Val Leu Leu Leu Cys Gly
1               5                   10                  15

Ala Val Phe Val Ser Pro Ser His Ala Val Ile His Val Thr Lys Glu
            20                  25                  30

Val Lys Glu Val Ala Thr Leu Ser Cys Gly His Asn Val Ser Val Glu
        35                  40                  45

Glu Leu Ala Gln Thr Arg Ile Tyr Trp Gln Lys Glu Lys Lys Met Val
    50                  55                  60

Leu Thr Met Met Ser Gly Asp Met Asn Ile Trp Pro Glu Tyr Lys Asn
65                  70                  75                  80

Arg Thr Ile Phe Asp Ile Thr Asn Asn Leu Ser Ile Val Ile Leu Ala
                85                  90                  95

Leu Arg Pro Ser Asp Glu Gly Thr Tyr Glu Cys Val Val Leu Lys Tyr
            100                 105                 110

Glu Lys Asp Ala Phe Lys Arg Glu His Leu Ala Glu Val Thr Leu Ser
        115                 120                 125

Val Lys Ala Asp Phe Pro Thr Pro Ser Ile Ser Asp Phe Glu Ile Pro
    130                 135                 140

Thr Ser Asn Ile Arg Arg Ile Ile Cys Ser Thr Ser Gly Gly Phe Pro
145                 150                 155                 160

Glu Pro His Leu Ser Trp Leu Glu Asn Gly Glu Glu Leu Asn Ala Ile
                165                 170                 175

Asn Thr Thr Val Ser Gln Asp Pro Glu Thr Glu Leu Tyr Ala Val Ser
            180                 185                 190

Ser Lys Leu Asp Phe Asn Met Thr Thr Asn His Ser Phe Met Cys Leu
        195                 200                 205

Ile Lys Tyr Gly His Leu Arg Val Asn Gln Thr Phe Asn Trp Asn Thr
    210                 215                 220

Thr Lys Gln Glu His Phe Pro Asp Asn Gly Ser Gly Gly Gly Gly Ser
225                 230                 235                 240

Gly Gly Gly Gly Ser Gly Gly Gly Gly Ser Ala Glu Ser Lys Tyr Gly
                245                 250                 255

Pro Pro Cys Pro Pro Cys Pro Ala Pro Glu Ala Ala Gly Gly Pro Ser
```

```
            260                 265                 270

Val Phe Leu Phe Pro Pro Lys Pro Lys Asp Gln Leu Met Ile Ser Arg
        275                 280                 285

Thr Pro Glu Val Thr Cys Val Val Val Asp Val Ser Gln Glu Asp Pro
    290                 295                 300

Glu Val Gln Phe Asn Trp Tyr Val Asp Gly Val Glu Val His Asn Ala
305                 310                 315                 320

Lys Thr Lys Pro Arg Glu Glu Gln Phe Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Gly Leu Pro Ser Ser Ile Glu Lys Thr
        355                 360                 365

Ile Ser Lys Ala Lys Gly Gln Pro Arg Glu Pro Gln Val Tyr Thr Leu
    370                 375                 380

Pro Pro Ser Gln Glu Glu Met Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Arg Leu Thr Val Asp Lys Ser
        435                 440                 445

Arg Trp Gln Glu Gly Asn Val Phe Ser Cys Ser Val Leu His Glu Ala
    450                 455                 460

Leu His Asn His Tyr Thr Gln Lys Ser Leu Ser Leu Ser Leu Gly
465                 470                 475
```

<210> SEQ ID NO 41
<211> LENGTH: 1851
<212> TYPE: DNA
<213> ORGANISM: Artificial Sequence
<220> FEATURE:
<223> OTHER INFORMATION: nucleotides coding fusion protein (hCD80-Fc-IL2wt)

<400> SEQUENCE: 41

```
atggatgcta tgctgagagg cctgtgttgc gtgctgctgc tgtgtggcgc tgtgttcgtg     60

tctccttctc acgctgtgat ccacgtgacc aaagaagtga aagaggtcgc cacactgtcc    120

tgcggccaca acgtttcagt ggaagaactg gcccagacca ggatctactg gcagaaagaa    180

aagaaaatgg tgctgaccat gatgtccggc gacatgaaca tctggcctga gtacaagaac    240

cggaccatct tcgacatcac caacaacctg tccatcgtga ttctggccct gaggccttct    300

gatgagggca cctatgagtg cgtggtgctg aagtacgaga aggacgcctt caagcgcgag    360

cacctggctg aagtgacact gtccgtgaag gccgactttc ccacaccttc catctccgac    420

ttcgagatcc ctacctccaa catccggcgg atcatctgtt ctacctctgg cggctttcct    480

gagcctcacc tgtcttggct ggaaaacggc gaggaactga acgccatcaa caccaccgtg    540

tctcaggacc ccgaaaccga gctgtacgct gtgtcctcca agctggactt caacatgacc    600

accaaccaca gcttcatgtg cctgattaag tacggccacc tgagagtgaa ccagaccttc    660

aactggaaca ccaccaagca agagcacttc cctgacaatg gatctggcgg cggaggttct    720

ggcggaggtg gaagcggagg cggaggatct gctgagtcta agtatggccc tccttgtcct    780

ccatgtcctg ctccagaagc tgctggcgga ccctctgtgt tcctgtttcc tccaaagcct    840
```

```
aaggaccagc tcatgatctc tcggacaccc gaagtgacct gcgtggtggt ggatgtgtct    900

caagaggacc ctgaggtgca gttcaattgg tacgtggacg gcgtggaagt gcacaacgcc    960

aagaccaagc ctagagagga acagttcaac tccacctaca gagtggtgtc cgtgctgacc   1020

gtgctgcacc aggattggct gaacggcaaa gagtacaagt gcaaggtgtc caacaagggc   1080

ctgccttcca gcatcgaaaa gaccatctcc aaggctaagg gccagcctag ggaaccccag   1140

gtttacaccc tgcctccaag ccaagaggaa atgaccaaga accaggtgtc cctgacctgc   1200

ctggtcaagg gcttctaccc ttccgacatt gccgtggaat gggagtccaa tggccagcct   1260

gagaacaact acaagaccac acctcctgtg ctggactccg acggctcctt ctttctgtac   1320

tctcgcctga ccgtggacaa gtctagatgg caagagggca acgtgttctc ctgctctgtg   1380

ctgcacgagg ccctgcacaa tcactacacc cagaagtccc tgtctctgtc tcttggaggt   1440

ggtggcggtt ctgcccctac cagctcctct accaagaaaa cccagctcca gttggagcat   1500

ctgctgctgg acctccagat gattctgaac gggatcaaca actataagaa ccccaagctg   1560

acccgcatgc tgacctttaa gttctacatg cccaagaagg ccaccgagct gaagcacctc   1620

cagtgcctgg aagaagaact gaagcccctg gaagaggtgc tgaatctggc ccagtccaag   1680

aacttccacc tgaggccacg ggacctgatc agcaacatca acgtgatcgt gctggaactg   1740

aagggctccg agacaacctt tatgtgcgag tacgccgacg agacagccac catcgtggaa   1800

tttctgaacc ggtggatcac cttctgccag agcatcatct ccacactgac c            1851
```

```
<210> SEQ ID NO 42
<211> LENGTH: 367
<212> TYPE: PRT
<213> ORGANISM: Artificial Sequence
<220> FEATURE:
<223> OTHER INFORMATION: Fc-IL2wt

<400> SEQUENCE: 42

Ala Glu Ser Lys Tyr Gly Pro Pro Cys Pro Pro Cys Pro Ala Pro Glu
1               5                   10                  15

Ala Ala Gly Gly Pro Ser Val Phe Leu Phe Pro Pro Lys Pro Lys Asp
            20                  25                  30

Gln Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
```

```
            180                 185                 190

Leu Thr Val Asp Lys Ser Arg Trp Gln Glu Gly Asn Val Phe Ser Cys
        195                 200                 205

Ser Val Leu His Glu Ala Leu His Asn His Tyr Thr Gln Lys Ser Leu
    210                 215                 220

Ser Leu Ser Leu Gly Gly Gly Gly Gly Ser Ala Pro Thr Ser Ser Ser
225                 230                 235                 240

Thr Lys Lys Thr Gln Leu Gln Leu Glu His Leu Leu Leu Asp Leu Gln
                245                 250                 255

Met Ile Leu Asn Gly Ile Asn Asn Tyr Lys Asn Pro Lys Leu Thr Arg
            260                 265                 270

Met Leu Thr Phe Lys Phe Tyr Met Pro Lys Lys Ala Thr Glu Leu Lys
        275                 280                 285

His Leu Gln Cys Leu Glu Glu Glu Leu Lys Pro Leu Glu Glu Val Leu
    290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
            340                 345                 350

Asn Arg Trp Ile Thr Phe Cys Gln Ser Ile Ile Ser Thr Leu Thr
        355                 360                 365
```

<210> SEQ ID NO 43
<211> LENGTH: 1176
<212> TYPE: DNA
<213> ORGANISM: Artificial Sequence
<220> FEATURE:
<223> OTHER INFORMATION: Fc-IL2wt

<400> SEQUENCE: 43

```
atggatgcta tgctgagagg cctgtgttgc gtgctgctgc tgtgtggcgc tgtgttcgtg     60

tctccttctc acgctgctga gtctaagtat ggccctcctt gtcctccatg tcctgctcca    120

gaagctgctg gcggaccctc tgtgttcctg tttcctccaa agcctaagga ccagctcatg    180

atctctcgga cacccgaagt gacctgcgtg gtggtggatg tgtctcaaga ggaccctgag    240

gtgcagttca attggtacgt ggacggcgtg gaagtgcaca acgccaagac caagcctaga    300

gaggaacagt tcaactccac ctacagagtg gtgtccgtgc tgaccgtgct gcaccaggat    360

tggctgaacg gcaaagagta caagtgcaag gtgtccaaca agggcctgcc ttccagcatc    420

gaaaagacca tctccaaggc taagggccag cctagggaac cccaggttta caccctgcct    480

ccaagccaag aggaaatgac caagaaccag gtgtccctga cctgcctggt caagggcttc    540

taccccttccg acattgccgt ggaatgggag tccaatggcc agcctgagaa caactacaag    600

accacacctc ctgtgctgga ctccgacggc tccttcttc tgtactctcg cctgaccgtg    660

gacaagtcta gatggcaaga gggcaacgtg ttctcctgct ctgtgctgca cgaggccctg    720

cacaatcact acacccagaa gtccctgtct ctgtctcttg gaggtggtgg cggttctgcc    780

cctaccagct cctctaccaa gaaaacccag ctccagttgg agcatctgct gctggacctc    840

cagatgattc tgaacgggat caacaactat aagaacccca agctgacccg catgctgacc    900

tttaagttct acatgcccaa gaaggccacc gagctgaagc acctccagtg cctggaagaa    960

gaactgaagc ccctggaaga ggtgctgaat ctggcccagt ccaagaactt ccacctgagg   1020
```

```
ccacgggacc tgatcagcaa catcaacgtg atcgtgctgg aactgaaggg ctccgagaca   1080

acctttatgt gcgagtacgc cgacgagaca gccaccatcg tggaatttct gaaccggtgg   1140

atcaccttct gccagagcat catctccaca ctgacc                              1176


<210> SEQ ID NO 44
<211> LENGTH: 392
<212> TYPE: PRT
<213> ORGANISM: Artificial Sequence
<220> FEATURE:
<223> OTHER INFORMATION: Fc-IL2v2

<400> SEQUENCE: 44

Met Asp Ala Met Leu Arg Gly Leu Cys Cys Val Leu Leu Leu Cys Gly
1               5                   10                  15

Ala Val Phe Val Ser Pro Ser His Ala Ala Glu Ser Lys Tyr Gly Pro
            20                  25                  30

Pro Cys Pro Pro Cys Pro Ala Pro Glu Ala Ala Gly Gly Pro Ser Val
        35                  40                  45

Phe Leu Phe Pro Pro Lys Pro Lys Asp Gln Leu Met Ile Ser Arg Thr
    50                  55                  60

Pro Glu Val Thr Cys Val Val Val Asp Val Ser Gln Glu Asp Pro Glu
65                  70                  75                  80

Val Gln Phe Asn Trp Tyr Val Asp Gly Val Glu Val His Asn Ala Lys
                85                  90                  95

Thr Lys Pro Arg Glu Glu Gln Phe Asn Ser Thr Tyr Arg Val Val Ser
            100                 105                 110

Val Leu Thr Val Leu His Gln Asp Trp Leu Asn Gly Lys Glu Tyr Lys
        115                 120                 125

Cys Lys Val Ser Asn Lys Gly Leu Pro Ser Ser Ile Glu Lys Thr Ile
    130                 135                 140

Ser Lys Ala Lys Gly Gln Pro Arg Glu Pro Gln Val Tyr Thr Leu Pro
145                 150                 155                 160

Pro Ser Gln Glu Glu Met Thr Lys Asn Gln Val Ser Leu Thr Cys Leu
                165                 170                 175

Val Lys Gly Phe Tyr Pro Ser Asp Ile Ala Val Glu Trp Glu Ser Asn
            180                 185                 190

Gly Gln Pro Glu Asn Asn Tyr Lys Thr Thr Pro Pro Val Leu Asp Ser
        195                 200                 205

Asp Gly Ser Phe Phe Leu Tyr Ser Arg Leu Thr Val Asp Lys Ser Arg
    210                 215                 220

Trp Gln Glu Gly Asn Val Phe Ser Cys Ser Val Leu His Glu Ala Leu
225                 230                 235                 240

His Asn His Tyr Thr Gln Lys Ser Leu Ser Leu Ser Leu Gly Gly Gly
                245                 250                 255

Gly Gly Ser Ala Pro Thr Ser Ser Ser Thr Lys Lys Thr Gln Leu Gln
            260                 265                 270

Leu Glu His Leu Leu Leu Asp Leu Gln Met Ile Leu Asn Gly Ile Asn
        275                 280                 285

Asn Tyr Lys Asn Pro Lys Leu Thr Ala Met Leu Thr Ala Lys Phe Tyr
    290                 295                 300

Met Pro Lys Lys Ala Thr Glu Leu Lys His Leu Gln Cys Leu Glu Glu
305                 310                 315                 320

Glu Leu Lys Pro Leu Glu Glu Val Leu Asn Leu Ala Gln Ser Lys Asn
                325                 330                 335
```

```
Phe His Leu Arg Pro Arg Asp Leu Ile Ser Asn Ile Asn Val Ile Val
            340                 345                 350

Leu Glu Leu Lys Gly Ser Glu Thr Thr Phe Met Cys Glu Tyr Ala Asp
        355                 360                 365

Glu Thr Ala Thr Ile Val Glu Phe Leu Asn Arg Trp Ile Thr Phe Cys
    370                 375                 380

Gln Ser Ile Ile Ser Thr Leu Thr
385                 390


<210> SEQ ID NO 45
<211> LENGTH: 1200
<212> TYPE: DNA
<213> ORGANISM: Artificial Sequence
<220> FEATURE:
<223> OTHER INFORMATION: nucleotides coding Fc-IL2v2

<400> SEQUENCE: 45

ggatccgcca ccatggatgc tatgctgaga ggcctgtgtt gcgtgctgct gctgtgtggc      60

gctgtgttcg tgtctccatc tcacgccgct gagtctaagt acggccctcc ttgtcctcca     120

tgtcctgctc cagaagctgc tggcggaccc tctgtgttcc tgtttcctcc aaagcctaag     180

gaccagctca tgatctctcg gacccctgaa gtgacctgcg tggtggtgga tgtgtctcaa     240

gaggaccctg aggtgcagtt caattggtac gtggacggcg tggaagtgca caacgccaag     300

accaagccta gagaggaaca gttcaactcc acctacagag tggtgtccgt gctgaccgtg     360

ctgcaccagg attggctgaa cggcaaagag tacaagtgca aggtgtccaa caagggcctg     420

ccttccagca tcgaaaagac catctccaag gctaagggcc agcctaggga accccaggtt     480

tacaccctgc ctccaagcca agaggaaatg accaagaacc aggtgtccct gacctgcctg     540

gtcaagggct tctacccttc cgacattgcc gtggaatggg agtccaatgg ccagcctgag     600

aacaactaca agaccacacc tcctgtgctg gactccgacg gctccttctt tctgtactct     660

cgcctgaccg tggacaagtc taggtggcaa gagggcaacg tgttctcctg ctctgtgctg     720

cacgaggccc tgcacaatca ctacacccag aagtccctgt ctctgtctct tggcggaggc     780

ggaggatctg ctcctacctc cagctccacc aagaaaaccc agctccagtt ggagcatctg     840

ctgctggacc tccagatgat cctgaatggc atcaacaatt acaagaaccc caagctgacc     900

gccatgctga ccgctaagtt ctacatgccc aagaaggcca ccgagctgaa gcacctccag     960

tgcctggaag aggaactgaa gcccctggaa gaagtgctga atctggccca gtccaagaac    1020

ttccacctga ggcctaggga cctgatctcc aacatcaacg tgatcgtgct ggaactgaaa    1080

ggctccgaga caaccttcat gtgcgagtac gccgacgaga cagccaccat cgtggaattt    1140

ctgaaccggt ggatcacctt ctgccagtcc atcatctcca cactgacctg atgactcgag    1200


<210> SEQ ID NO 46
<211> LENGTH: 592
<212> TYPE: PRT
<213> ORGANISM: Artificial Sequence
<220> FEATURE:
<223> OTHER INFORMATION: CD80-Fc-IL2wt

<400> SEQUENCE: 46

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
```

-continued

```
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Gly Ser Ala Pro Thr Ser Ser
    450                 455                 460
```

-continued

```
Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Phe Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590
```

COMPOSITION FOR CULTURING REGULATORY T CELLS AND USE THEREOF

CROSS-REFERENCE TO RELATED APPLICATIONS

This is a Continuation under 35 USC § 120 and 35 USC § 365(c) of International Patent Application No. PCT/KR2020/016382 filed Nov. 19, 2020, and claims priority under 35 USC § 119 of Korean Patent Application No. 10-2019-0149779 filed Nov. 20, 2019 and Korean Patent Application No. 10-2020-0033229 filed Mar. 18, 2020. The disclosures of all such applications are hereby incorporated herein by reference in their respective entireties, for all purposes.

JOINT RESEARCH AGREEMENT

The claimed invention hereof was made as a result of activities undertaken within the scope of a joint research agreement between GI CELL, INC. and GI INNOVATION, INC. that was in effect prior to the date the invention was made.

REFERENCE TO SEQUENCE LISTING SUBMITTED VIA EFS

This application includes an electronically submitted sequence listing in .txt format. The .txt file contains a sequence listing entitled "625 SeqListing ST25.txt" created on May 8, 2022 and is 123,239 bytes in size. The sequence listing contained in this .txt file is part of the specification and is hereby incorporated by reference herein in its entirety.

TECHNICAL FIELD

The present invention relates to a composition for culturing T cells and a method for culturing regulatory T cells using the same.

BACKGROUND ART

T cells plays a central role in cell-mediated immunity. T cells are distinguished from other lymphocytes including B cells, by receptors on the surface of T cells, such as T cell receptors (TCR). In addition, T cells include various types of T cells such as helper T cells (TH cells), cytotoxic T cells (TC cells or CTL), memory T cells (TM cells) including central memory T cells (TCM cells) and effector memory T cells (TEM cells), natural killer T cells (NKT cells), gamma delta T cells (γδT cells), and regulatory T cell (Treg cells).

Among them, regulatory T cell (Treg) are T cells that act to suppress the immune response of other cells. For example, Treg cells act to suppress T cell-mediated immunity during an immune response and to suppress self-reactive T cells that escaped negative selection in the thymus. Treg cells may be largely classified into natural regulatory T cells (nTreg) and induced regulatory T cells (iTreg). Natural regulatory T cells known as CD4+CD25+ FoxP3+ regulatory T cells develop in the thymus. Induced regulatory T cells share a number of attributes with naturally occurring Treg cells, but the characteristic of conversion from CD4+CD25−FoxP3− T cells into CD4+CD25+FoxP3+ regulatory T cells is known as a representative difference.

As such, studies on the importance of regulatory T cells in relation to a disease caused by abnormalities in various autoimmune systems have actively been conducted. Since the concept of suppressor T cells was introduced and proposed first by Gershon (R K Gershon and K Kondo, Immunology, 1970, 18: 723-37) in the early 1970s, research has been conducted in many fields of immunology to elucidate the biological properties and functions of regulatory T cells. In particular, since it was suggested in 1995 by Sakaguchi that CD25 may function as an important phenotypic marker for naturally occurring CD4+ regulatory T cells (S Sakaguchi et, al., J Immunol, 1995, 155: 1151-1164), research has been conducted, focusing on the role and importance of regulatory T cells in inducing peripheral tolerance to self-antigens.

Regulatory T cells are known to able to secrete IL-10, TGF-β, IL-35, or the like known as immunosuppressive cytokines (H Nishikawa et, al., Int. J. Cancer, 2010, 127: 759-767). Research that proves regulatory T cells which secretes immunosuppressive cytokines may secrete IL-10, or the like to induce antigen-specific T cells which cause an autoimmune disease into immune tolerant antigen presenting cells, thereby inducing immunological tolerance have been conducted (S. Karumuthil-Melethil et, al., Diabetes, 2015, 64:1341-1357).

As such, uses of regulatory T cells to treat an autoimmune disease are widely known, but specific methods that may amplify natural killer cells to use them effectively are still insufficient.

DETAILED DESCRIPTION OF THE INVENTION

Technical Problem

Accordingly, the present inventors studied a method for effectively culturing regulatory T cells, and as a result, found out that a novel fusion protein dimer containing an IL-2 protein and a CD80 protein in one molecule may effectively proliferate regulatory T cells, and have completed the present invention.

Solution to Problem

To achieve the above purpose, in accordance with an exemplary embodiment, a composition or medium for culturing regulatory T cells comprises, as an active ingredient, a fusion protein dimer containing an IL-2 protein or a variant thereof and a CD80 protein or a fragment thereof.

In accordance with another exemplary embodiment, a method for culturing regulatory T cells using a fusion protein dimer containing an IL-2 protein or a variant thereof and a CD80 protein or a fragment thereof is provided.

In accordance with yet another exemplary embodiment, a pharmaceutical composition comprises, as an active ingredient, regulatory T cells cultured in a medium comprising a fusion protein dimer containing an IL-2 protein or a variant thereof and a CD80 protein or a fragment thereof.

Effect of the Invention

The culture composition according to the present invention may not only effectively proliferate T cells, but in particular, effectively proliferate regulatory T cells. In particular, it was confirmed that the viability of regulatory T cells was significantly increased as compared with a culture method using conventionally used IL-2. It was also confirmed that the amount of Foxp3+ expression was increased in the obtained regulatory T cells. Therefore, this proliferation method may be used in the field of cell therapy using regulatory T cells.

BRIEF DESCRIPTION OF DRAWINGS

Exemplary embodiments can be understood in more detail from the following description taken in conjunction with the accompanying drawings, in which.

BEST MODE FOR CARRYING OUT THE INVENTION

Figure 1A:
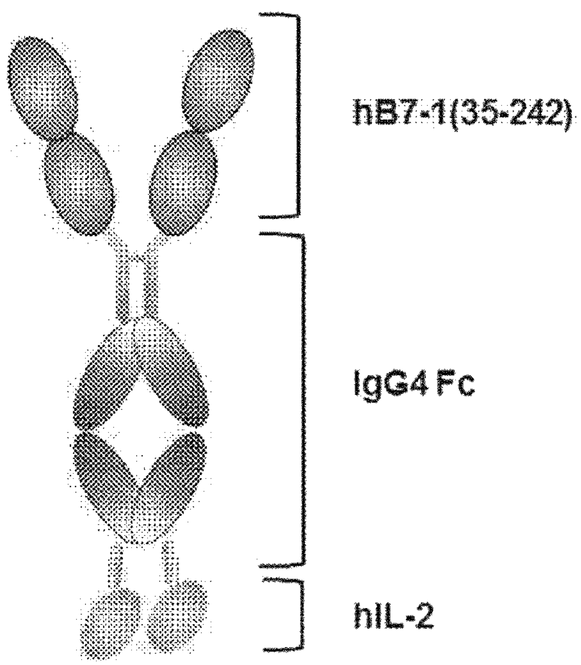
FIG. 1A is a schematic diagram of a fusion protein dimer used in the present invention.

Composition and Medium for Proliferating Regulatory T Cells

An aspect of the present invention provides a composition for proliferating regulatory T cells comprising, as an active ingredient, a fusion protein dimer containing an IL-2 protein or a variant thereof and a CD80 protein or a fragment thereof. In addition, a regulatory T cell culture medium comprising the fusion protein dimer as an active ingredient is provided.

The regulatory T cell proliferation medium may be a medium in which the fusion protein dimer containing an IL-2 protein or a variant thereof and a CD80 protein or a fragment thereof is added to a T cell culture medium. In this case, the T cell culture medium may comprise any one selected from the group consisting of amino acids, sugars, inorganic salts, and vitamins. Preferably, the T cell culture medium may comprise any amino acid, any sugar, any inorganic salt, and any vitamin. In addition, the medium may further comprise fetal bovine serum (FBS), hydroxyethyl piperazine ethane sulfonic acid (HEPES), proteins, carbohydrates, mercaptoethanol, and growth factors. Also, the regulatory T cell culture medium may further comprise retinoic acid. In an embodiment, the regulatory T cell proliferation medium may comprise basic components described in the following Table 3 or Table 4.

As used herein, the term "cell culture medium" means a medium used for culturing cells, specifically regulatory T cells, and more specifically means a medium for culturing CD4+CD25+CD127− cells. This contains components required by cells for cell growth and survival in vitro, or comprises components that help cell growth and survival. Specifically, the components may be vitamins, essential or non-essential amino acids, and trace elements. The medium may be a medium used for culturing cells, preferably eukaryotic cells, more preferably regulatory T cells, and much more preferably CD4+CD25+CD127− T cells or CD4+CD25+Foxp3+ T cells.

The cell culture medium according to the present invention comprises any amino acid component, any vitamin component, any inorganic salt component, any other component, and purified water, wherein:

a) the amino acid component is at least one amino acid selected from the group consisting of glycine, L-alanine, L-valine, L-leucine, L-isoleucine, L-threonine, L-serine, L-cysteine, L-methionine, L-aspartic acid, L-asparagine, L-glutamic acid, L-glutamine, L-lysine, L-arginine, L-histidine, L-phenylalanine, L-tyrosine, L-tryptophan, L-proline, β-alanine, γ-aminobutyric acid, ornithine, citrulline, homoserine, triiodothyronine, thyroxine and dioxy phenylalanine, or a combination thereof, and preferably at least one amino acid selected from the group consisting of glycine, L-alanine, L-arginine, L-cysteine, L-glutamine, L-histidine, L-lysine, L-methionine, L-proline, L-serine, L-threonine and L-valine, or a combination thereof;

b) the vitamin component is at least one vitamin selected from the group consisting of biotin, calcium D-pantothenate, folic acid, niacinamide, pyridoxine hydrochloride, riboflavin, thiamine hydrochloride, vitamin B12, choline chloride, i-inositol and ascorbic acid, or a combination thereof, and preferably at least one vitamin selected from the group consisting of i-inositol, thiamine hydrochloride, niacinamide and pyridoxine hydrochloride, or a combination thereof;

c) the inorganic salt component is at least one inorganic salt selected from the group consisting of calcium chloride ($CaCl_2$))(anhydrous), copper sulfate pentahydrate ($CuSO_4$-$5H_2O$), iron (II) sulfate heptahydrate ($FeSO_4$-$7H_2O$), magnesium chloride (anhydrous), magnesium sulfate ($MgSO_4$) (anhydrous), potassium chloride (KCl), sodium chloride (NaCl), disodium hydrogen phosphate ($Na_2HPO_4$), sodium dihydrogen phosphate monohydrate ($NaH_2PO_4$—$H_2O$), zinc sulfate heptahydrate ($ZnSO_4$-$7H_2O$), iron (III) nitrate nonahydrate ($Fe(NO_3)_3.9H_2O$) and sodium hydrogen carbonate ($NaHCO_3$), or a combination thereof, and preferably at least one inorganic salt selected from the group consisting of sodium chloride (NaCl), sodium hydrogen carbonate ($NaHCO_3$), potassium chloride (KCl), calcium chloride ($CaCl_2$))(anhydrous) and sodium dihydrogen phosphate monohydrate ($NaH_2PO_4$-$H_2O$), or a combination thereof;

d) the other component is at least one other component selected from the group consisting of D-glucose (dextrose), sodium pyruvate, hypoxanthine Na, thymidine, linoleic acid, lipoic acid, adenosine, cytidine, guanosine, uridine, 2'-deoxyadenosine, 2'-deoxycytidine HCl and 2'-deoxyguanosine, or a combination thereof, and it may preferably be sodium pyruvate; and e) the purified water is used to dissolve the amino acids, vitamins, inorganic salts, and other components, and may be obtained by one or more processes of distillation, or purified through a filter.

In addition, the cell culture medium according to the present invention may further comprise growth factors or cytokines. The growth factor may be IGF, bFGF, TGF, HGF, EGF, VEGF, PDGF, or the like alone or at least two thereof, but is not limited thereto. The cytokine may be IL-1, IL-4, IL-6, IFN-γ, IL-10, IL-17, or the like alone or at least two thereof, but is not limited thereto.

As used herein, the term "T cell" refers to one of lymphocytes responsible for antigen-specific adaptive immunity. T cells are classified into naive T cells that have not yet met an antigen, and mature T cells and memory T cells that have met an antigen. At this time, the mature effector T cells comprise helper T cells, cytotoxic T cells, and natural killer T cells.

As used herein, the term "helper T cell or Th cell" refers to a cell that promotes humoral immunity by regulating differentiation and activation of other white blood cells. It is also called a CD4+ T cell because it has a CD4 protein on the cell surface. Helper T cells may be further classified into Th1, Th2, Th17, and Tregs according to their detailed functions. Th1 cells secrete interferon-gamma (IFN-γ) and tumor necrosis factor beta (TNF-β), thereby inducing endosomes and lysosomes to fuse to form endolysosomes within macrophages. Meanwhile, Th2 cells secrete several types of interleukin (IL), allowing B cells to differentiate into plasma cells. Th17 cells secrete interleukin-17 (IL-17) to recruit neutrophils.

As used herein, the term "regulatory T cell (Treg)" comprises natural regulatory T cells (nTreg) or induced regulatory T cells (iTreg). The regulatory T cells herein comprise CD4+CD25+ T cells, CD4+CD25+CD127low/− T cells, or CD4+CD25+Foxp3+ T cells. The regulatory T cells maintain immune homeostasis and block an autoimmune response, and the like by inhibiting an immune response.

As used herein, the term "cytotoxic T cell" refers to a cell that kills virus-infected cells or tumor cells, or the like by secreting cytotoxic substances such as granzyme or perforin. It is also called a CD8 T cell because it has a CD8 protein on the cell surface. In contrast to helper T cells, it eliminates virus and cancer cells by mediating cellular immunity.

As used herein, the term "natural killer T cell" refers to one of effector T cells that is distributed in a small proportion as compared with helper T cells and cytotoxic cells. Natural killer T cells have the same T cell receptors (TCR) on the cell surface as T cells, but also have natural killer cell-specific molecules such as NK1.1. Natural killer T cells secrete gamma interferon, interleukin-4, or the like to regulate an immune response.

As used herein, the term "memory T cell" refers to a T cell that has potential ability to function as an effector T cell as it has recognized an antigen and survived long-time following differentiation and selection processes, and later when the antigen re-invades, is quickly activated. Naive T cells differentiate into activated cells by recognizing an antigen, or effector T cells differentiate into long-lived memory T cells by influence of interleukin-7 and interleukin-15.

In this case, a fusion protein dimer containing an IL-2 protein or a variant thereof and a CD80 protein or a fragment thereof may be comprised in a culture medium in an amount of 1 nM to 2,000 nM. In addition, the dimer may be comprised in an amount of 1 nM to 1,000 nM or 1 nM to 500 nM. Further, the dimer may be comprised in an amount of 2 nM to 300 nM, 5 nM to 100 nM, 10 nM to 80 nM, 20 nM to 70 nM, or 40 nM to 50 nM. Specifically, the fusion protein dimer may be comprised in a medium in an amount of 1 nM, 3.2 nM, 10 nM, or 50 nM.

A Fusion Protein Dimer Containing an IL-2 Protein or a Variant Thereof and a CD80 Protein or a Fragment Thereof As used herein, the term "IL-2" or "interleukin-2", unless otherwise stated, refers to any wild-type IL-2 obtained from any vertebrate source, comprising mammals, for example, primates (such as humans) and rodents (such as mice and rats). IL-2 may be obtained from animal cells, and also comprises one obtained from recombinant cells capable of producing IL-2. In addition, IL-2 may be wild-type IL-2 or a variant thereof.

In the present specification, IL-2 or a variant thereof may be collectively expressed by the term "IL-2 protein" or "IL-2 polypeptide." IL-2, an IL-2 protein, an IL-2 polypeptide, and an IL-2 variant specifically bind to, for example, an IL-2 receptor. This specific binding may be identified by methods known to those skilled in the art.

An embodiment of IL-2 may have the amino acid sequence of SEQ ID NO: 35 or SEQ ID NO: 36. Here, IL-2 may also be in a mature form. Specifically, the mature IL-2 may not contain a signal sequence, and may have the amino acid sequence of SEQ ID NO: 10. Here, IL-2 may be used under a concept encompassing a fragment of wild-type IL-2 in which a portion of N-terminus or C-terminus of the wild-type IL-2 is truncated.

In addition, the fragment of IL-2 may be in a form in which 1, 2, 3, 4, 5, 6, 7, 8, 9, 10, 11, 12, 13, 14, 15, 16, 17, 18, 19, 20, 21, 22, 23, 24, or 25 continuous amino acids are truncated from N-terminus of a protein having the amino acid sequence of SEQ ID NO: 35 or SEQ ID NO: 36. In addition, the fragment of IL-2 may be in a form in which 1, 2, 3, 4, 5, 6, 7, 8, 9, 10, 11, 12, 13, 14, 15, 16, 17, 18, 19, 20, 21, 22, 23, 24, or 25 continuous amino acids are truncated from C-terminus of a protein having the amino acid sequence of SEQ ID NO: 35 or SEQ ID NO: 36.

As used herein, the term "IL-2 variant" refers to a form in which a portion of amino acids in the full-length IL-2 or the above-described fragment of IL-2 is substituted. That is, an IL-2 variant may have an amino acid sequence different from wild-type IL-2 or a fragment thereof. However, an IL-2 variant may have activity equivalent or similar to the wild-type IL-2. Here, "IL-2 activity" may, for example, refer to specific binding to an IL-2 receptor, which specific binding can be measured by methods known to those skilled in the art.

Specifically, an IL-2 variant may be obtained by substitution of a portion of amino acids in the wild-type IL-2. An embodiment of the IL-2 variant obtained by amino acid substitution may be obtained by substitution of at least one of the $38^{th}$, $42^{nd}$, $45^{th}$, $61^{st}$, and $72^{nd}$ amino acids in the amino acid sequence of SEQ ID NO: 10.

Specifically, the IL-2 variant may be obtained by substitution of at least one of the $38^{th}$, $42^{nd}$, $45^{th}$, $61^{st}$, or $72^{nd}$ amino acid in the amino acid sequence of SEQ ID NO: 10 with another amino acid. In addition, when IL-2 is in a form in which a portion of N-terminus in the amino acid sequence of SEQ ID NO: 35 is truncated, the amino acid at a position complementarily corresponding to that in the amino acid sequence of SEQ ID NO: 10 may be substituted with another amino acid. For example, when IL-2 has the amino acid sequence of SEQ ID NO: 35, its IL-2 variant may be obtained by substitution of at least one of $58^{th}$, $62^{nd}$, $65^{th}$, $81^{st}$, or $92^{nd}$ amino acid in the amino acid sequence of SEQ ID NO: 35 with another amino acid. These amino acid residues correspond to the $38^{th}$, $42^{nd}$, $45^{th}$, $61^{st}$, and $72^{nd}$ amino acid residues in the amino acid sequence of SEQ ID NO: 10, respectively. According to an embodiment, one, two, three, four, five, six, seven, eight, nine, or ten amino acids may be substituted as long as such IL-2 variant maintains IL-2 activity. According to another embodiment, one to five amino acids may be substituted.

In an embodiment, an IL-2 variant may be in a form in which two amino acids are substituted. Specifically, the IL-2 variant may be obtained by substitution of the $38^{th}$ and $42^{nd}$ amino acids in the amino acid sequence of SEQ ID NO: 10. In addition, in an embodiment, the IL-2 variant may be obtained by substitution of the $38^{th}$ and $45^{th}$ amino acids in the amino acid sequence of SEQ ID NO: 10. In addition, in an embodiment, the IL-2 variant may be obtained by substitution of the $38^{th}$ and $61^{st}$ amino acids in the amino acid sequence of SEQ ID NO: 10. In addition, in an embodiment, the IL-2 variant may be obtained by substitution of the $38^{th}$ and $72^{nd}$ amino acids in the amino acid sequence of SEQ ID NO: 10. In addition, in an embodiment, the IL-2 variant may be obtained by substitution of the $42^{nd}$ and $45^{th}$ amino acids in the amino acid sequence of SEQ ID NO: 10. In addition, in an embodiment, the IL-2 variant may be obtained by substitution of the $42^{nd}$ and $61^{st}$ amino acids in the amino acid sequence of SEQ ID NO: 10. In addition, in an embodiment, the IL-2 variant may be obtained by substitution of the $42^{nd}$ and $72^{nd}$ amino acids in the amino acid sequence of SEQ ID NO: 10. In addition, in an embodiment, the IL-2 variant may be obtained by substitution of the $45^{th}$ and $61^{st}$ amino acids in the amino acid sequence of SEQ ID NO: 10. In addition, in an embodiment, the IL-2 variant may be obtained by substitution of the $45^{th}$ and $72^{nd}$ amino acids in the amino acid sequence of SEQ ID NO: 10. In addition, in an embodiment, the IL-2 variant may be obtained by substitution of the $61^{st}$ and $72^{nd}$ amino acids in the amino acid sequence of SEQ ID NO: 10.

Furthermore, an IL-2 variant may be in a form in which three amino acids are substituted. Specifically, the IL-2 variant may be obtained by substitution of the $38^{th}$, $42^{nd}$, and $45^{th}$ amino acids in the amino acid sequence of SEQ ID NO: 10. In addition, in an embodiment, the IL-2 variant may be obtained by substitution of the $38^{th}$, $42^{nd}$, and $61^{st}$ amino acids in the amino acid sequence of SEQ ID NO: 10. In addition, in an embodiment, the IL-2 variant may be obtained by substitution of the $38^{th}$, $42^{nd}$, and $72^{nd}$ amino acids in the amino acid sequence of SEQ ID NO: 10. In addition, in an embodiment, the IL-2 variant may be obtained by substitution of the $38^{th}$, $45^{th}$, and $61^{st}$ amino acids in the amino acid sequence of SEQ ID NO: 10. In addition, in an embodiment, the IL-2 variant may be obtained by substitution of the $38^{th}$, $45^{th}$, and $72^{nd}$ amino acids in the amino acid sequence of SEQ ID NO: 10. In addition, in an embodiment, the IL-2 variant may be obtained by substitution of the $38^{th}$, $61^{st}$, and $72^{nd}$ amino acids in the amino acid sequence of SEQ ID NO: 10. In addition, in an embodiment, the IL-2 variant may be obtained by substitution of the $42^{nd}$, $45^{th}$, and $61^{st}$ amino acids in the amino acid sequence of SEQ ID NO: 10. In addition, in an embodiment, the IL-2 variant may be obtained by substitution of the $42^{nd}$, $45^{th}$, and $72^{nd}$ amino acids in the amino acid sequence of SEQ ID NO: 10. In addition, in an embodiment, the IL-2 variant may be obtained by substitution of the $45^{th}$, $61^{st}$, and $72^{nd}$ amino acids in the amino acid sequence of SEQ ID NO: 10.

In addition, an IL-2 variant may be in a form in which four amino acids are substituted. Specifically, the IL-2 variant may be obtained by substitution of the $38^{th}$, $42^{nd}$, $45^{th}$, and $61^{st}$ amino acids in the amino acid sequence of SEQ ID NO: 10. In addition, in an embodiment, the IL-2 variant may be obtained by substitution of the $38^{th}$, $42^{nd}$, $45^{th}$, and $72^{nd}$ amino acids in the amino acid sequence of SEQ ID NO: 10. In addition, in an embodiment, the IL-2 variant may be obtained by substitution of the $38^{th}$, $45^{th}$, $61^{st}$, and $72^{nd}$ amino acids in the amino acid sequence of SEQ ID NO: 10. In addition, in an embodiment, the IL-2 variant may be obtained by substitution of the $38^{th}$, $42^{nd}$, $61^{st}$, and $72^{nd}$ amino acids in the amino acid sequence of SEQ ID NO: 10. In addition, in an embodiment, the IL-2 variant may be obtained by substitution of $42^{nd}$, $45^{th}$, $61^{st}$, and $72^{nd}$ amino acids in the amino acid sequence of SEQ ID NO: 10.

Furthermore, an IL-2 variant may be in a form in which five amino acids are substituted. Specifically, the IL-2 variant may be obtained by substitution of each of the $38^{th}$, $42^{nd}$, $45^{th}$, $61^{st}$, and $72^{nd}$ amino acids in the amino acid sequence of SEQ ID NO: 10 with another amino acid.

Here, the "another amino acid" introduced by the substitution may be any one selected from the group consisting of alanine, arginine, asparagine, aspartic acid, cysteine, glutamic acid, glutamine, histidine, isoleucine, leucine, lysine, methionine, phenylalanine, proline, serine, threonine, tryptophan, tyrosine, and valine. However, regarding amino acid substitution for the IL-2 variant, in the amino acid sequence of SEQ ID NO: 10, the $38^{th}$ amino acid cannot be substituted with arginine, the $42^{nd}$ amino acid cannot be substituted with phenylalanine, the $45^{th}$ amino acid cannot be substituted with tyrosine, the $61^{st}$ amino acid cannot be substituted with glutamic acid, and the $72^{nd}$ amino acid cannot be substituted with leucine.

Regarding amino acid substitution for an IL-2 variant, in the amino acid sequence of SEQ ID NO: 10, the $38^{th}$ amino acid, arginine, may be substituted with an amino acid other than arginine. Preferably, regarding amino acid substitution for an IL-2 variant, in the amino acid sequence of SEQ ID NO: 10, the $38^{th}$ amino acid, arginine, may be substituted with alanine (R38A).

Regarding amino acid substitution for an IL-2 variant, in the amino acid sequence of SEQ ID NO: 10, the $42^{nd}$ amino acid, phenylalanine, may be substituted with an amino acid other than phenylalanine. Preferably, regarding amino acid substitution for an IL-2 variant, in the amino acid sequence of SEQ ID NO: 10, the $42^{nd}$ amino acid, phenylalanine, may be substituted with alanine (F42A).

Regarding amino acid substitution for an IL-2 variant, in the amino acid sequence of SEQ ID NO: 10, the $45^{th}$ amino acid, tyrosine, may be substituted with an amino acid other than tyrosine. Preferably, regarding amino acid substitution for an IL-2 variant, in the amino acid sequence of SEQ ID NO: 10, the $45^{th}$ amino acid, tyrosine, may be substituted with alanine (Y45A).

Regarding amino acid substitution for an IL-2 variant, in the amino acid sequence of SEQ ID NO: 10, the $61^{st}$ amino acid, glutamic acid, may be substituted with an amino acid other than glutamic acid. Preferably, regarding amino acid substitution for an IL-2 variant, in the amino acid sequence of SEQ ID NO: 10, the $61^{st}$ amino acid, glutamic acid, may be substituted with arginine (E61R).

Regarding amino acid substitution for an IL-2 variant, in the amino acid sequence of SEQ ID NO: 10, the $72^{nd}$ amino acid, leucine, may be substituted with an amino acid other than leucine. Preferably, regarding amino acid substitution for an IL-2 variant, in the amino acid sequence of SEQ ID NO: 10, the $72^{nd}$ amino acid, leucine, may be substituted with glycine (L72G).

Specifically, an IL-2 variant may be obtained by at least one substitution selected from the group consisting of R38A, F42A, Y45A, E61R, and L72G, in the amino acid sequence of SEQ ID NO: 10.

Specifically, an IL-2 variant may be obtained by amino acid substitutions at two, three, four, or five positions among the positions selected from the group consisting of R38A, F42A, Y45A, E61R, and L72G.

In addition, an IL-2 variant may be in a form in which two amino acids are substituted. Specifically, an IL-2 variant may be obtained by the substitutions, R38A and F42A. In addition, in an embodiment, an IL-2 variant may be obtained by the substitutions, R38A and Y45A. In addition, in an embodiment, an IL-2 variant may be obtained by the substitutions, R38A and E61R. In addition, in an embodiment, an IL-2 variant may be obtained by the substitutions, R38A and L72G. In addition, in an embodiment, an IL-2 variant may be obtained by the substitutions, F42A and Y45A. In addition, in an embodiment, an IL-2 variant may be obtained by the substitutions, F42A and E61R. In addition, in an embodiment, an IL-2 variant may be obtained by the substitutions, F42A and L72G. In addition, in an embodiment, an IL-2 variant may be obtained by the substitutions, E61R and L72G.

Furthermore, an IL-2 variant may be in a form in which three amino acids are substituted. Specifically, an IL-2 variant may be obtained by the substitutions, R38A, F42A, and Y45A. In addition, in an embodiment, an IL-2 variant may be obtained by the substitutions, R38A, F42A, and E61R. In addition, in an embodiment, an IL-2 variant may be obtained by the substitutions, R38A, F42A, and L72G. In addition, in an embodiment, an IL-2 variant may be obtained by the substitutions, R38A, Y45A, and E61R. In addition, in an embodiment, an IL-2 variant may be obtained by the substitutions, R38A, Y45A, and L72G. In addition, in an embodiment, an IL-2 variant may be obtained by the substitutions, F42A, Y45A, and E61R. In addition, in an embodiment, an IL-2 variant may be obtained by the substitutions, F42A, Y45A, and L72G. In addition, in an embodiment, an IL-2 variant may be obtained by the substitutions, F42A, E61R, and L72G. In addition, in an embodiment, an IL-2 variant may be obtained by the substitutions, Y45A, E61R, and L72G.

In addition, an IL-2 variant may be in a form in which four amino acids are substituted. Specifically, an IL-2 variant may be obtained by the substitutions, R38A, F42A, Y45A, and E61R. In addition, in an embodiment, an IL-2 variant may be obtained by the substitutions, R38A, F42A, Y45A, and L72G. In addition, in an embodiment, an IL-2 variant may be obtained by the substitutions, R38A, F42A, E61R, and L72G. In addition, in an embodiment, an IL-2 variant may be obtained by the substitutions, R38A, Y45A, E61R, and L72G. In addition, in an embodiment, an IL-2 variant may be obtained by the substitutions, F42A, Y45A, E61R, and L72G.

Furthermore, an IL-2 variant may be obtained by the substitutions, R38A, F42A, Y45A, E61R, and L72G.

Preferably, an embodiment of the IL-2 variant may contain which are any one selected from the following substitution combinations (a) to (d) in the amino acid sequence of SEQ ID NO: 10:

(a) R38A/F42A (b) R38A/F42A/Y45A (c) R38A/F42A/E61R (d) R38A/F42A/L72G

Here, when IL-2 has the amino acid sequence of SEQ ID NO: 35, an amino acid substitution may be present at a position complementarily corresponding to that in the amino acid sequence of SEQ ID NO: 10. In addition, even when IL-2 is a fragment of the amino acid sequence of SEQ ID NO: 35, an amino acid substitution may be present at a position complementarily corresponding to that in the amino acid sequence of SEQ ID NO: 10.

Specifically, an IL-2 variant may have the amino acid sequence of SEQ ID NO: 6, 22, 23, or 24.

In addition, an IL-2 variant may be characterized by having low in vivo toxicity. Here, the low in vivo toxicity may be a side effect caused by binding of IL-2 to the IL-2 receptor alpha chain (IL-2Ra). Various IL-2 variants have been developed to ameliorate the side effect caused by binding of IL-2 to IL-2Ra, and such IL-2 variants may be those disclosed in U.S. Pat. No. 5,229,109 and Korean Patent No. 1667096. In particular, IL-2 variants described in the present application have low binding affinity for the IL-2 receptor alpha chain (IL-2Ra) and thus have lower in vivo toxicity than the wild-type IL-2.

As used herein, the term "CD80", also called "B7-1", is a membrane protein present in dendritic cells, activated B cells, and monocytes. CD80 provides co-stimulatory signals essential for activation and survival of T cells. CD80 is known as a ligand for the two different proteins, CD28 and CTLA-4, present on the surface of T cells. CD80 consists of 288 amino acids, and may specifically have the amino acid sequence of SEQ ID NO: 11. In addition, as used herein, the term "CD80 protein" refers to the full-length CD80 or a CD80 fragment.

As used herein, the term "CD80 fragment" refers to a truncated form of CD80. In addition, the CD80 fragment may be an extracellular domain of CD80. An embodiment of the CD80 fragment may be obtained by elimination of the $1^{st}$ to $34^{th}$ amino acids from N-terminus which are a signal sequence of CD80. Specifically, an embodiment of the CD80 fragment may be a protein consisting of the $35^{th}$ to $288^{th}$ amino acids in SEQ ID NO: 11. In addition, an embodiment of the CD80 fragment may be a protein consisting of the $35^{th}$ to $242^{nd}$ amino acids in SEQ ID NO: 11. In addition, an embodiment of the CD80 fragment may be a protein consisting of the $35^{th}$ to $232^{nd}$ amino acids in SEQ ID NO: 11. In addition, an embodiment of the CD80 fragment may be a protein consisting of the $35^{th}$ to $139^{th}$ amino acids in SEQ ID NO: 11. In addition, an embodiment of the CD80 fragment may be a protein consisting of the $142^{nd}$ to $242^{nd}$ amino acids in SEQ ID NO: 11. In an embodiment, a CD80 fragment may have the amino acid sequence of SEQ ID NO: 2.

In addition, the IL-2 protein and the CD80 protein may be attached to each other via a linker or a carrier. Specifically, the IL-2 or a variant thereof and the CD80 (B7-1) or a fragment thereof may be attached to each other via a linker or a carrier. In the present description, the linker and the carrier may be used interchangeably.

The linker links two proteins. An embodiment of the linker may comprise 1 to 50 amino acids, albumin or a fragment thereof, an Fc domain of an immunoglobulin, or the like. Here, the Fc domain of immunoglobulin refers to a protein that contains heavy chain constant region 2 (CH2) and heavy chain constant region 3 (CH3) of an immunoglobulin, and does not contain heavy and light chain variable regions and light chain constant region 1 (CH1) of an immunoglobulin. The immunoglobulin may be IgG, IgA, IgE, IgD, or IgM, and may preferably be IgG4. Here, Fc domain of wild-type immunoglobulin G4 may have the amino acid sequence of SEQ ID NO: 4.

In addition, the Fc domain of an immunoglobulin may be an Fc domain variant as well as wild-type Fc domain. In addition, as used herein, the term "Fc domain variant" may refer to a form which is different from the wild-type Fc domain in terms of glycosylation pattern, has a high glycosylation as compared with the wild-type Fc domain, or has a low glycosylation as compared with the wild-type Fc domain, or a deglycosylated form. In addition, an aglycosylated Fc domain is comprised therein. The Fc domain or a variant thereof may be adapted to have an adjusted number of sialic acids, fucosylations, or glycosylations, through culture conditions or genetic manipulation of a host.

In addition, glycosylation of the Fc domain of an immunoglobulin may be modified by conventional methods such as chemical methods, enzymatic methods, and genetic engineering methods using microorganisms. In addition, the Fc domain variant may be in a mixed form of respective Fc regions of immunoglobulins, IgG, IgA, IgE, IgD, and IgM. In addition, the Fc domain variant may be in a form in which some amino acids of the Fc domain are substituted with other amino acids. An embodiment of the Fc domain variant may have the amino acid sequence of SEQ ID NO: 12.

The fusion protein may have a structure in which, using an Fc domain as a linker (or carrier), a CD80 protein and an IL-2 protein, or an IL-2 protein and a CD80 protein are linked to N-terminus and C-terminus of the linker or carrier, respectively (FIG. 1A). Linkage between N-terminus or C-terminus of the Fc domain and CD-80 or IL-2 may optionally be achieved by a linker peptide.

Specifically, a fusion protein may consist of the following structural formula (I) or (II):

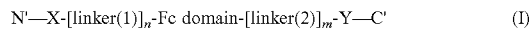

N'—X-[linker(1)]$_n$-Fc domain-[linker(2)]$_m$-Y—C' (I)

N'—Y-[linker(1)]$_n$-Fc domain-[linker(2)]$_m$-X—C' (II)

Here, in the structural formulas (I) and (II),
N' is the N-terminus of the fusion protein,
C' is the C-terminus of the fusion protein,
X is a CD80 protein,
Y is an IL-2 protein,
the linkers (1) and (2) are peptide linkers, and
n and m are each independently 0 or 1.

Preferably, the fusion protein may consist of the structural formula (I). The IL-2 protein is as described above. In addition, the CD80 protein is as described above. According to an embodiment, the IL-2 protein may be an IL-2 variant with one to five amino acid substitutions as compared with the wild-type IL-2. The CD80 protein may be a fragment obtained by truncation of up to about 34 continuous amino acid residues from the N-terminus or C-terminus of the wild-type CD80. Alternatively, the CD protein may be an extracellular immunoglobulin-like domain having the activity of binding to the T cell surface receptors CTLA-4 and CD28.

Specifically, the fusion protein may have the amino acid sequence of SEQ ID NO: 9, 26, 28, or 30. According to another embodiment, the fusion protein comprises a polypeptide having a sequence identity of 85%, 86%, 87%, 88%, 89%, 90%, 91%, 92%, 93%, 94%, 95%, 96%, 97%, 98%, 99%, or 100% to the amino acid sequence of SEQ ID NO: 9, 26, 28, or 30. Here, the identity is, for example, percent homology, and may be determined through homology comparison software such as BlastN software of the National Center of Biotechnology Information (NCBI).

The peptide linker (1) may be comprised between the CD80 protein and the Fc domain. The peptide linker (1) may consist of 5 to 80 continuous amino acids, 20 to 60 continuous amino acids, 25 to 50 continuous amino acids, or 30 to 40 continuous amino acids. In an embodiment, the peptide linker (1) may consist of 30 amino acids. In addition, the peptide linker (1) may contain at least one cysteine. Specifically, the peptide linker (1) may contain one, two, or three cysteines. In addition, the peptide linker (1) may be derived from the hinge of an immunoglobulin. In an embodiment, the peptide linker (1) may be a peptide linker consisting of the amino acid sequence of SEQ ID NO: 3.

The peptide linker (2) may consist of 1 to 50 continuous amino acids, 3 to 30 continuous amino acids, or 5 to 15 continuous amino acids. In an embodiment, the peptide linker (2) may be (G45). (where n is an integer of 1 to 10). Here, in $(G45)_n$, n may be 1, 2, 3, 4, 5, 6, 7, 8, 9, or 10. In an embodiment, the peptide linker (2) may be a peptide linker consisting of the amino acid sequence of SEQ ID NO: 5.

In another aspect of the present invention, there is provided a dimer obtained by binding of two fusion proteins, each of which comprises an IL-2 protein and a CD80 protein. The fusion protein comprising IL-2 or a variant thereof and CD80 or a fragment thereof is as described above.

Here, the binding between the fusion proteins constituting the dimer may be achieved by, but is not limited to, a disulfide bond formed by cysteines present in the linker. The fusion proteins constituting the dimer may be the same or different fusion proteins from each other. Preferably, the dimer may be a homodimer. An embodiment of the fusion protein constituting the dimer may be a protein having the amino acid sequence of SEQ ID NO: 9.

Regulatory T Cell Culture Method

Another aspect of the present invention provides a method for culturing regulatory T cells, comprising culturing CD4+CD25+CD127− T cells in a medium comprising a fusion protein dimer containing an IL-2 protein or a variant thereof and a CD80 protein or a fragment thereof.

At this time, the CD4+CD25+CD127− T cells may be obtained from blood cells. At this time, CD4+CD25+CD127− T cells may be isolated from peripheral blood mononuclear cells (PBMC). Alternatively, the CD4+CD25+CD127− T cells may be obtained by specifically proliferating CD4+CD25+CD127− T cells from blood cells. Alternatively, the CD4+CD25+CD127− T cells may be obtained from CD4+ cells after removing PBMCs from CD4− T cells. In addition, CD4+ T cells may be isolated using anti-CD4 antibodies, and in an embodiment, these were isolated using beads to which anti-CD4 antibodies are bound. In addition, CD25+T cells may be isolated by using anti-CD25+ antibodies. In particular, regulatory T cell may be isolated by isolating CD4+, CD25+ and CD127− T cells.

The medium may be a conventionally used medium. Preferably, it may be a medium optimized for CD4+CD25+CD127− T cells. In a specific embodiment, it may be a medium in which FBS, HEPES, L-glutamine, and 2-mercaptoethanol are added to a RPMI1640 medium or a TexMACS medium as disclosed in Tables 3 and 4. In addition, the medium may further comprise retinoic acid. In addition, the medium may further comprise penicillin and/or streptomycin.

At this time, the regulatory CD4+ T cells may be cultured in the medium for 1 to 30 days or 2 to 20 days. In addition, these may be cultured for 3 to 10 days, or 4 to 6 days.

Meanwhile, the CD4+CD25+CD127− T cells may be obtained through a step of culturing CD4+ T cells; or a step of culturing CD25+ T cells.

At this time, the CD4+ T cells and CD25+ T cells may be obtained from blood cells, respectively. At this time, CD4+ T cells and CD25+ T cells may be isolated from peripheral blood mononuclear cells (PBMC) or may be obtained from blood cells by specifically proliferating CD4+ T cells or CD25+ T cells, respectively. Alternatively, CD4+ T cells or CD25+ T cells may be obtained after removing CD4-T cells or CD25− T from PBMCs. In addition, CD4+ T cells may be isolated using anti-CD4 antibodies, and in an embodiment, these were isolated using beads to which anti-CD4 antibodies are bound. In addition, CD25+ T cells may be isolated by using anti-CD25+ antibodies. In particular, regulatory T cell may be isolated by isolating CD4+, CD25+ and CD127− T cells from CD4+ T cells or CD25+ T cells.

Obtained Regulatory T Cells and Use Thereof

Another aspect of the present invention provides regulatory T cells obtained by the culture method.

Yet another aspect of the present invention provides a composition for treating a regulatory T cell-mediated disease, comprising regulatory T cells obtained by the above-described method as an active ingredient.

At this time, the regulatory T cells obtained by the culture method may have an increased amount of Foxp3+ expression. As used herein, the term "Foxp3" is a protein also called as scurfin. The protein is a protein involved in the regulatory mechanism pathway of regulatory T cells and known as a marker for regulatory T cells. Preferably, regulatory T cells obtained above may be CD4+CD25+CD127-Foxp3+ T cells.

As used herein, the term "regulatory T cell-mediated disease" refers to a disease induced by abnormality or deficiency of regulatory T cells, and may be specifically characterized as an inflammatory disease or an autoimmune disease.

A specific embodiment of the present invention may be characterized in that the inflammatory disease is at least one selected from the group consisting of lupus, Sjogren's syndrome, rheumatoid arthritis, fibromyositis, scleroderma, ankylosing spondylitis, Behcet's disease, Aphthous stomatitis, Gillian-Barre syndrome, alopecia areata, polymyositis, Crohn's disease, colitis, polyarteritis nodosa, recurrent polychondritis, and autoimmune thrombocytopenia. In addition, a specific embodiment of the present invention may be characterized in that the autoimmune disease is at least one selected from the group consisting of rheumatoid arthritis, systemic sclerosis, insulin-dependent juvenile diabetes caused by pancreatic cell antibodies, alopecia areata, psoriasis, pemphigus, asthma, aphtha stomatitis, chronic thyroiditis, some acquired aplastic anemia, primary cirrhosis, ulcerative colitis, Behcet's disease, Crohn's disease, silicosis, asbestosis, IgA nephropathy, poststreptococcal glomerulonephritis, Sjogren's syndrome, Gillian-Barre syndrome, polymyositis, multiple myositis, multiple sclerosis, autoimmune hemolytic anemia, autoimmune encephalomyelitis, myasthenia gravis, Graves' hyperthyroidism, polyarteritis nodosa, ankylosing spondylitis, fibromyalgia, temporal arteritis, Wilson's disease, Fanconi's syndrome, multiple myeloma, and systemic lupus erythematosus.

The composition of the present invention may comprise a pharmaceutically acceptable carrier and/or an additive, or the like. For example, it may comprise sterile water, normal saline, a conventional buffer (e.g., phosphoric acid, citric acid, and other organic acid), a stabilizer, a salt, an antioxidant, a surfactant, a suspending agent, an isotonic agent or a preservative. Further, it may, but not be limited thereto, comprise an organic substance such as a biopolymer and an inorganic substance such as hydroxyapatite, specifically, a collagen matrix, a polylactic acid polymer or its copolymer, a polyethylene glycol polymer or its copolymer, a chemical derivative thereof, and a mixture thereof. Examples of the stabilizer may comprise dextran 40, methylcellulose, gelatin, sodium sulfite, sodium metasulfate, or the like. Examples of the antioxidant may comprise a chelating agent such as erythorbic acid, dibutylhydroxytoluene, butylhydroxyanisole, α-tocopherol, tocopheryl acetate, L-ascorbic acid and its salt, L-ascorbic acid palmitate, L-ascorbic acid stearate, sodium hydrogen sulfite, sodium sulfite, gallic acid triamyl, gallic acid propyl or ethylenediaminetetraacetic acid sodium (EDTA), sodium pyrophosphate, sodium metaphosphate, and the like. Examples of the suspending agent may comprise methylcellulose, polysorbate 80, hydroxyethylcellulose, gum arabic, tragacanth gum, sodium carboxymethyl cellulose, polyoxyethylene sorbitan monolaurate, and the like. Examples of the isotonic agent may comprise D-mannitol and sorbitol. Examples of the preservative may comprise methyl paraoxy benzoate, ethyl paraoxy benzoate, sorbic acid, phenol, cresol, chloro-cresol, or the like.

Treatment Method Using the Obtained Regulatory T Cells

Another aspect of the present invention provides a method for treating a regulatory T cell-mediated disease comprising administering the regulatory T cells to an individual having a regulatory T cell-mediated disease. At this time, regulatory T cells and a regulatory T cell-mediated disease are as described above.

Yet another aspect of the present invention provides use of the regulatory T cells to treat a regulatory T cell-mediated disease.

MODE FOR CARRYING OUT THE INVENTION

Hereinafter, the present invention will be described in more detail by way of the following examples. However, the following examples are only for illustrating the present invention, and the scope of the present invention is not limited thereto.

Preparatory Example 1. Preparation of a hCD80-Fc-IL-2 Variant (2M): GI-101

In order to produce a fusion protein containing a human CD80 fragment, a Fc domain, and an IL-2 variant, a polynucleotide comprising a nucleotide sequence (SEQ ID NO: 8) encoding a fusion protein containing a signal peptide (SEQ ID NO: 1), a CD80 fragment (SEQ ID NO: 2), a linker-bound Ig hinge (SEQ ID NO: 3), a Fc domain (SEQ ID NO: 4), a linker (SEQ ID NO: 5), and an IL-2 variant (2M) in which two amino acids are substituted (R38A, F42A) (SEQ ID NO: 6) in this order from N-terminus was synthesized through Invitrogen GeneArt Gene Synthesis service of ThermoFisher Scientific Inc., and cloned into a pcDNA3_4 vector. In addition, the vector was introduced into CHO cells (EXPI-CHO™) to express a fusion protein of SEQ ID NO: 9. After introducing the vector, the culture solution was cultured in an environment of 37° C., 125 RPM, and 8% $CO_2$ for 7 days, and then collected to purify a fusion protein. The purified fusion protein dimer was named as “GI-101.”

Purification was performed using chromatography comprising MabSelect SuRe protein A resin. The fusion protein was bound under the condition of 25 mM Tris, 25 mM NaCl, and pH 7.4. Then, it was eluted with 100 mM NaCl and 100 mM acetic acid at pH 3. After putting 20% of 1M Tris-HCl at pH 9 into a collection tube, the fusion protein was collected. The collected fusion protein was dialyzed into PBS buffer for 16 hours to change.

Figure 1B:
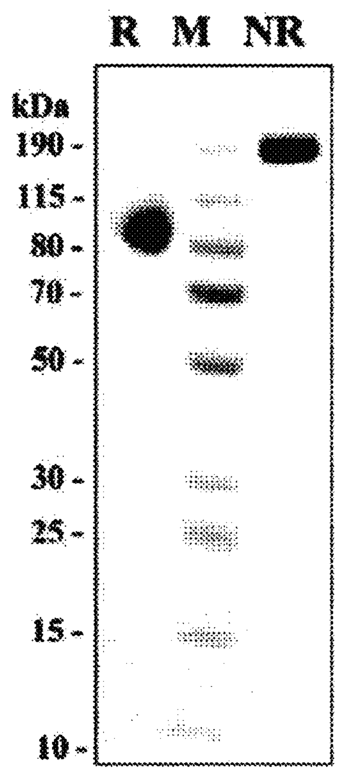
FIG. 1B shows an image of SDS-PAGE confirming the obtained fusion protein dimer (GI-101)
Figure 1C:
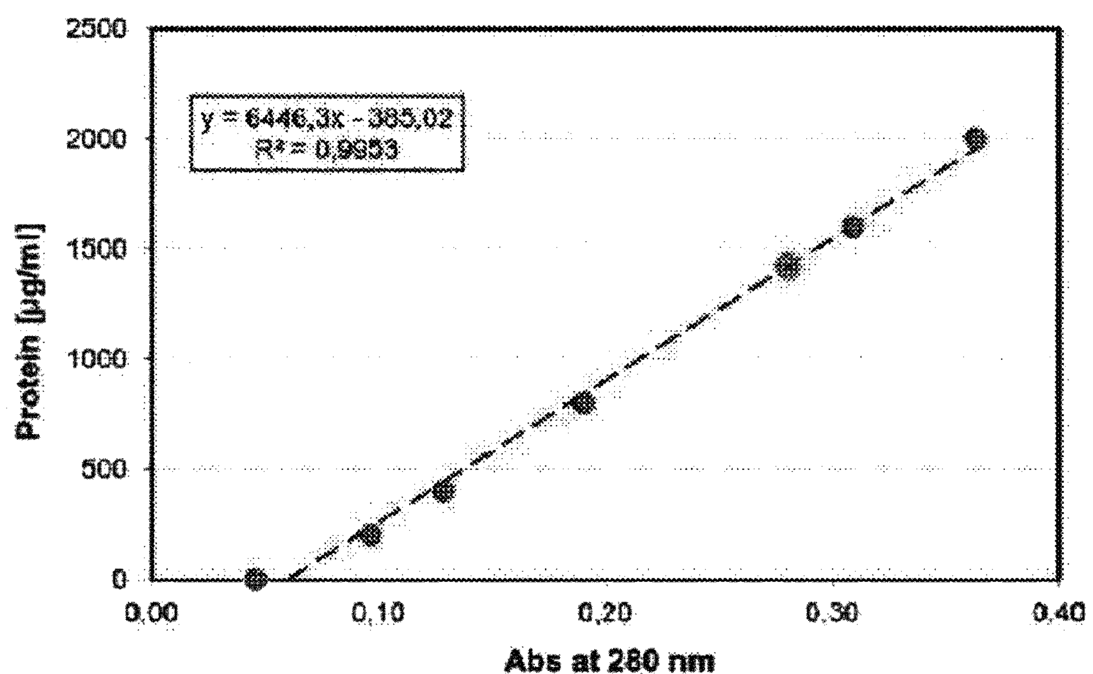
FIG. 1C shows a content of the fusion protein dimer (GI-101) according to the absorbance.
Figure 1D:
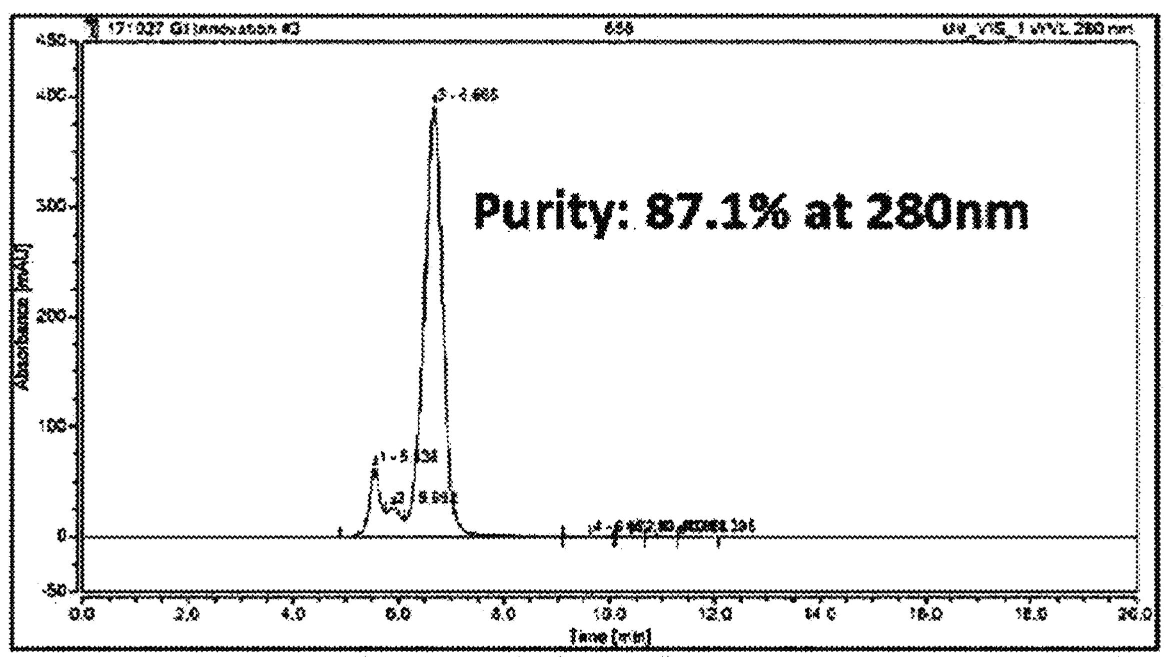
FIG. 1D shows size exclusion chromatography (SEC) analysis of the obtained fusion protein dimer (GI-101)

Then, absorbance at a wavelength of 280 nm over time was measured by using size exclusion chromatography with TSKgel G3000SWXL column (TOSOH Bioscience) to obtain a high concentration of fusion protein. At this time, the isolated and purified fusion protein was subjected to SDS-PAGE under the reducing (R) or non-reducing (NR) conditions, and stained with coomassie blue to confirm its purity (FIG. 1B). It was confirmed that the fusion protein was comprised at a concentration of 2.78 mg/ml as detected using NanoDrop (FIG. 1C). Also, the result analyzed using size exclusion chromatography is as shown in FIG. 1D.

Preparatory Example 2. Preparation of a Fc-IL-2 Variant (2M) Dimer: Fc-IL-2v2

In order to produce a fusion protein containing a Fc domain and an IL-2 variant, a polynucleotide comprising a nucleotide sequence (SEQ ID NO: 45) encoding a fusion protein containing a signal peptide (SEQ ID NO: 1), an Ig hinge (SEQ ID NO: 38), a Fc domain (SEQ ID NO: 4), a linker (SEQ ID NO: 5), and an IL-2 variant (2M) in which two amino acids are substituted (R38A, F42A) (SEQ ID NO: 6) in this order from N-terminus was synthesized through Invitrogen GeneArt Gene Synthesis service of ThermoFisher Scientific Inc., and cloned into a pcDNA3_4 vector. In addition, the vector was introduced into CHO cells (EXPI-CHO™) to express a fusion protein of SEQ ID NO: 44. After introducing the vector, the culture solution was cultured in an environment of 37° C., 125 RPM, and 8% $CO_2$ for 7 days, and then collected to purify a fusion protein dimer. The purified fusion protein dimer was named as “Fc-IL2v2.”

Figure 3A:
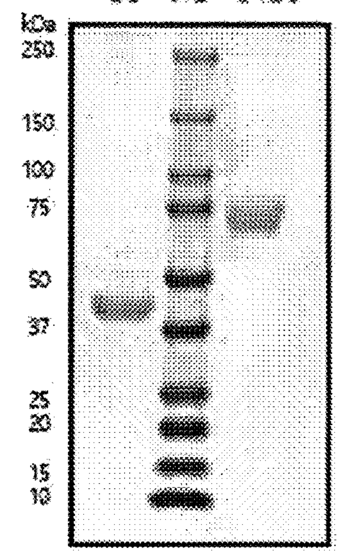
FIG. 3A shows an image of SDS-PAGE confirming the obtained Fc-IL2v2 fusion protein dimer.
Figure 3B:
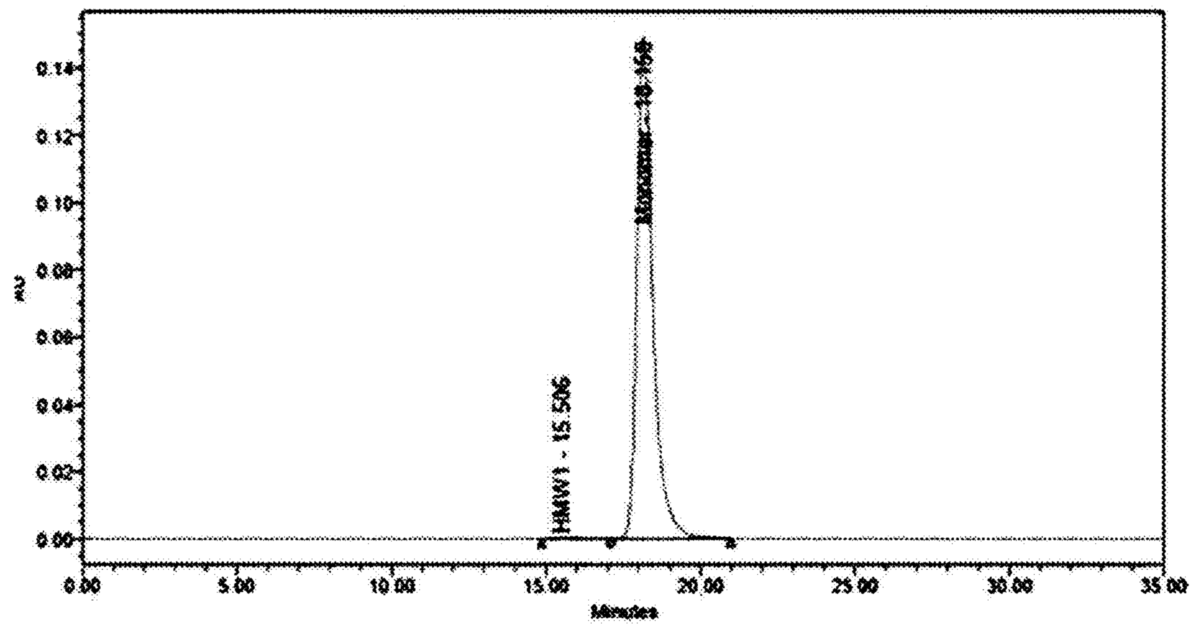
FIG. 3B shows size exclusion chromatography (SEC) analysis of the obtained Fc-IL2v2 fusion protein dimer.

The purification and collection of the fusion protein were performed in the same manner as in the Preparatory Example 1. The isolated and purified fusion protein was subjected to SDS-PAGE under the reducing (R) or non-reducing (NR) conditions, and stained with coomassie blue to confirm its purity (FIG. 3A). As a result, it was confirmed that the fusion protein forms a dimer. Also, the result analyzed using size exclusion chromatography is as shown in FIG. 3B.

Preparatory Example 3. Preparation of a Fc-IL-2 Dimer: Fc-IL-2 wt

In order to produce a fusion protein containing a Fc domain and a wild-type IL-2, a polynucleotide comprising a nucleotide sequence (SEQ ID NO: 43) encoding a fusion protein containing a signal peptide (SEQ ID NO: 1), an Ig hinge (SEQ ID NO: 38), a Fc domain (SEQ ID NO: 4), a linker (SEQ ID NO: 5), and a wild-type IL-2 (SEQ ID NO: 10) in this order from N-terminus was synthesized through Invitrogen GeneArt Gene Synthesis service of ThermoFisher Scientific Inc., and cloned into a pcDNA3_4 vector. In addition, the vector was introduced into CHO cells (EXPI-CHO™) to express a fusion protein of SEQ ID NO: 42. After introducing the vector, the culture solution was cultured in an environment of 37° C., 125 RPM, and 8% $CO_2$ for 7 days, and then collected to purify a fusion protein dimer. The purified fusion protein dimer was named as “Fc-IL2 wt.”

Figure 3C:
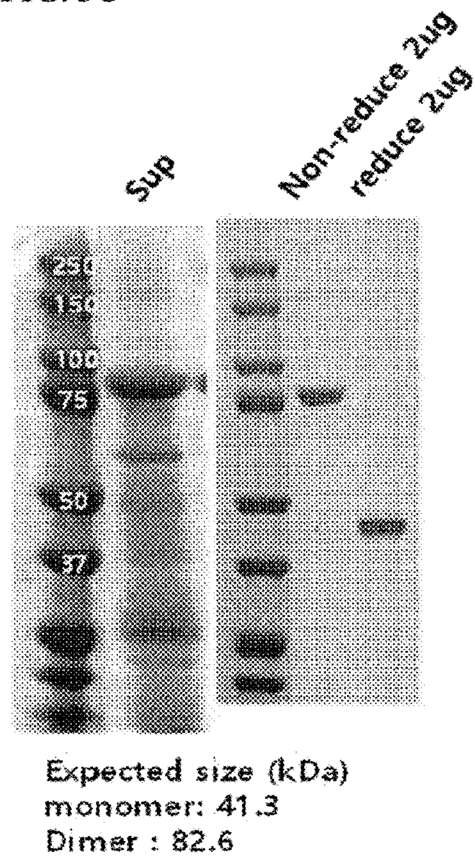
FIG. 3C shows an image of SDS-PAGE confirming the obtained Fc-IL2 wt fusion protein dimer.
Figure 3D:
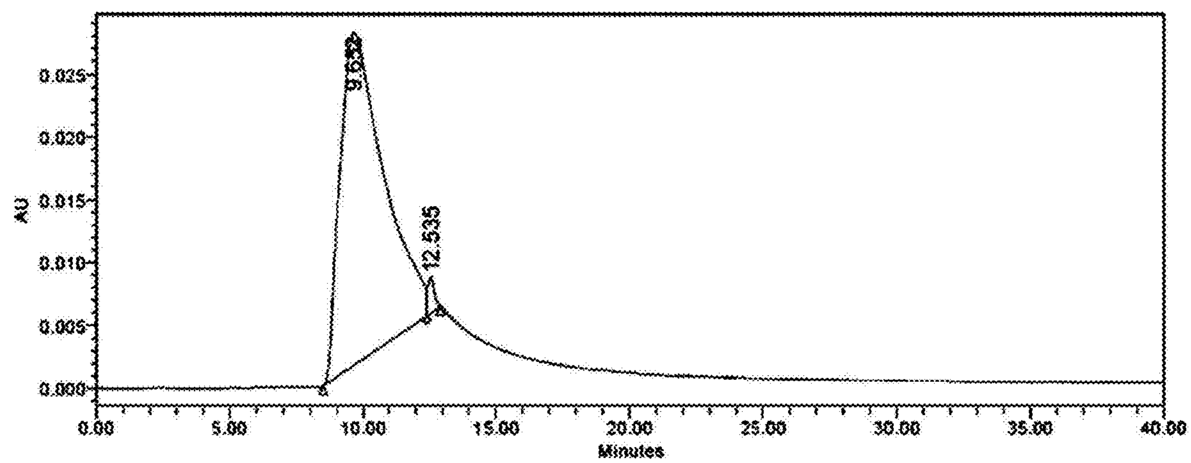
FIG. 3D shows size exclusion chromatography (SEC) analysis of the obtained Fc-IL2 wt fusion protein dimer.

The purification and collection of the fusion protein were performed in the same manner as in the Preparatory Example 1. The isolated and purified fusion protein was subjected to SDS-PAGE under the reducing (R) or non-reducing (NR) conditions, and stained with coomassie blue to confirm its purity (FIG. 3C). As a result, it was confirmed that the fusion protein forms a dimer. Also, the result analyzed using size exclusion chromatography is as shown in FIG. 3D.

Preparatory Example 4. Preparation of a hCD80-Fc-IL-2 Wild-Type Dimer: hCD80-Fc-IL-2 wt In order to produce a fusion protein containing a human CD80 fragment, a Fc domain, and an IL-2 wile-type protein, a polynucleotide comprising a nucleotide sequence (SEQ ID NO: 41) encoding a fusion protein containing a signal peptide (SEQ ID NO: 1), a CD80 fragment (SEQ ID NO: 2), a linker-bound Ig hinge (SEQ ID NO: 3), a Fc domain (SEQ ID NO: 4), a linker (SEQ ID NO: 5), and IL-2 wild-type (SEQ ID NO: 10) in this order from N-terminus was synthesized through Invitrogen GeneArt Gene Synthesis service of ThermoFisher Scientific Inc., and cloned into a pcDNA3_4 vector. In addition, the vector was introduced into CHO cells (EXPI-CHO™) to express a fusion protein of SEQ ID NO: 46. After introducing the vector, the culture solution was cultured in an environment of 37° C., 125 RPM, and 8% $CO_2$ for 7 days, and then collected to purify a fusion protein dimer. The purified fusion protein dimer was named as “hCD80-Fc-IL2 wt.”

Purification was performed using chromatography comprising MabSelect SuRe protein A resin. The fusion protein was bound under the condition of 25 mM Tris, 25 mM NaCl, and pH 7.4. Then, it was eluted with 100 mM NaCl and 100 mM acetic acid at pH 3. After putting 20% of 1M Tris-HCl at pH 9 into a collection tube, the fusion protein was collected. The collected fusion protein was dialyzed into PBS buffer for 16 hours to change.

Figure 4A:
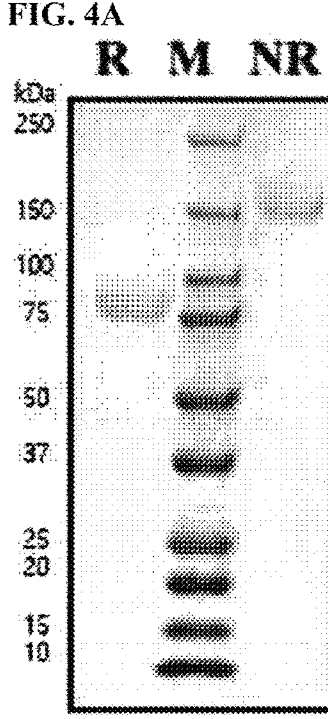
FIG. 4A shows an image of SDS-PAGE confirming the obtained hCD80-Fc-IL2 wt fusion protein dimer.
Figure 4B:
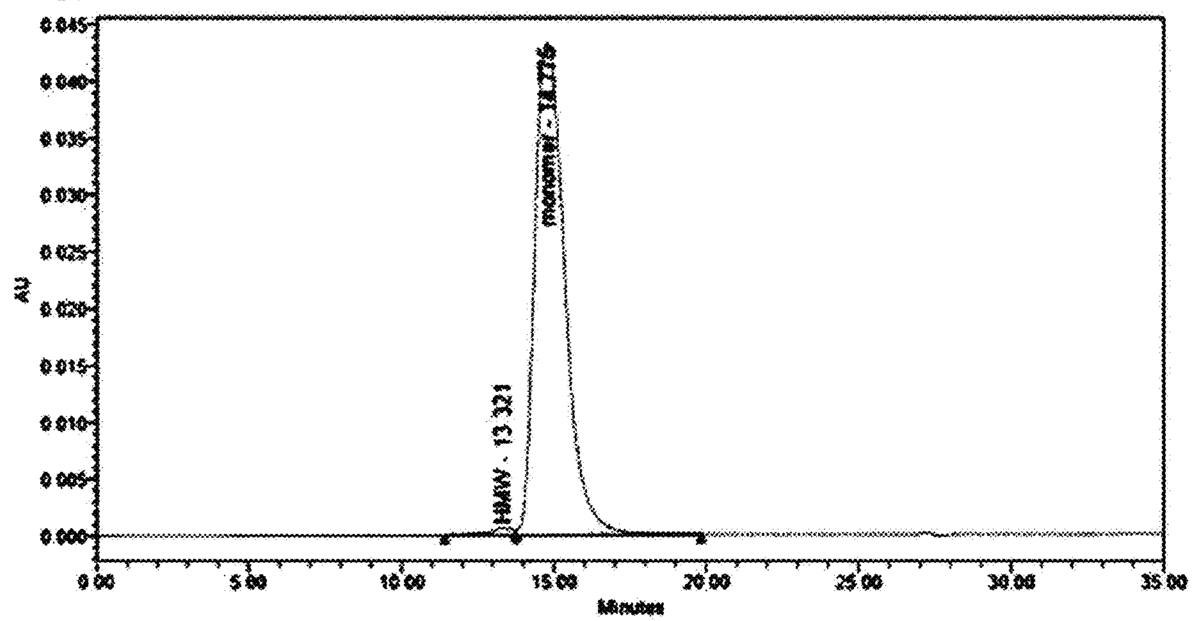
FIG. 4B shows size exclusion chromatography (SEC) analysis of the obtained hCD80-Fc-IL2 wt fusion protein dimer.
Figure 5:
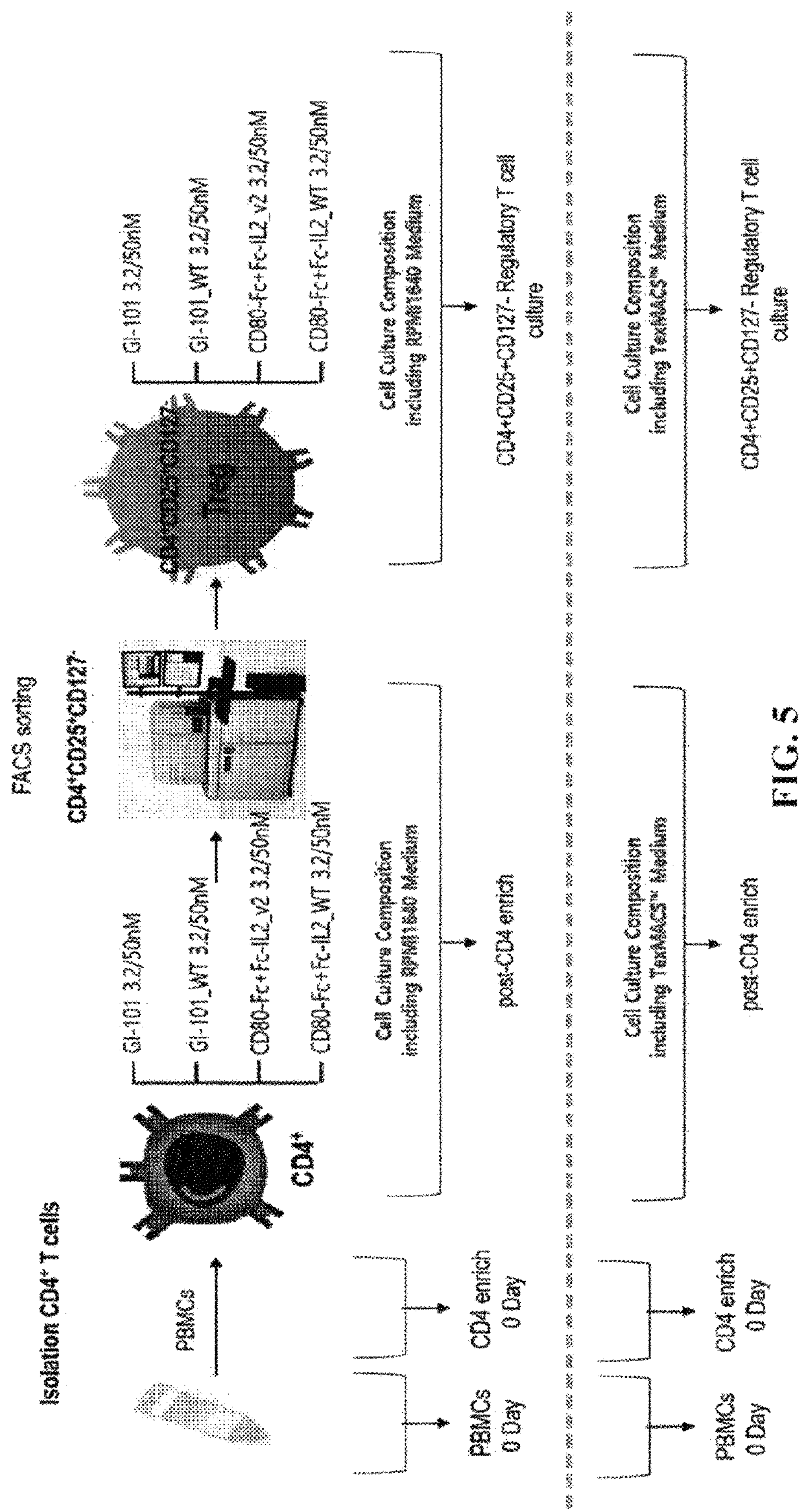
FIG. 5 shows a schematic diagram of a method for culturing Treg cells using a fusion protein dimer.

Then, absorbance at a wavelength of 280 nm over time was measured by using size exclusion chromatography with TSKgel G3000SWXL column (TOSOH Bioscience) to obtain a high concentration of fusion protein. At this time, the isolated and purified fusion protein was subjected to SDS-PAGE under the reducing (R) or non-reducing (NR) conditions, and stained with coomassie blue to confirm its purity (FIG. 4A). As a result, it was confirmed that the fusion protein forms a dimer. Also, the result analyzed using size exclusion chromatography is as shown in FIG. 4B.

Preparatory Example 5. Preparation of a hCD80-Fc Dimer: hCD80-Fc

In order to produce a fusion protein containing a human CD80 fragment and a Fc domain, a polynucleotide (SEQ ID NO: 39) comprising a nucleotide sequence encoding a fusion protein containing a signal peptide (SEQ ID NO: 1), a CD80 fragment (SEQ ID NO: 2), a linker-bound Ig hinge (SEQ ID NO: 3), and a Fc domain (SEQ ID NO: 4) in this order from N-terminus was synthesized through Invitrogen GeneArt Gene Synthesis service of ThermoFisher Scientific Inc., and cloned into a pcDNA3_4 vector. In addition, the vector was introduced into CHO cells (EXPI-CHO™) to express a fusion protein of SEQ ID NO: 40. After introducing the vector, the culture solution was cultured in an environment of 37° C., 125 RPM, and 8% $CO_2$ for 7 days, and then collected to purify a fusion protein dimer. The purified fusion protein dimer was named "hCD80-Fc."

Purification was performed using chromatography comprising MabSelect SuRe protein A resin. The fusion protein was bound under the condition of 25 mM Tris, 25 mM NaCl, and pH 7.4. Then, it was eluted with 100 mM NaCl and 100 mM acetic acid at pH 3. After putting 20% of 1 M Tris-HCl at pH 9 into a collection tube, the fusion protein was collected. The collected fusion protein was dialyzed into PBS buffer for 16 hours to change.

Figure 2A:
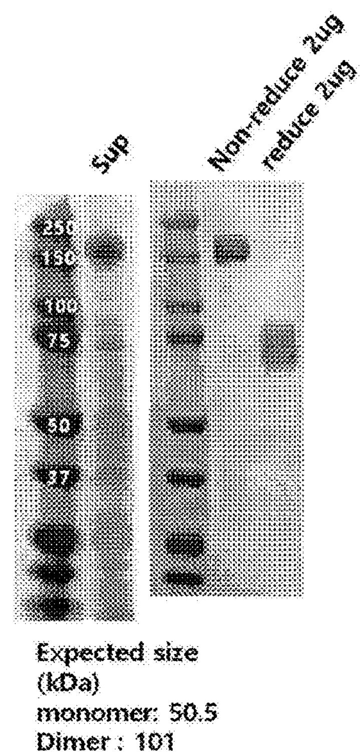
FIG. 2A shows an image of SDS-PAGE confirming the obtained hCD80-Fc fusion protein dimer.
Figure 2B:
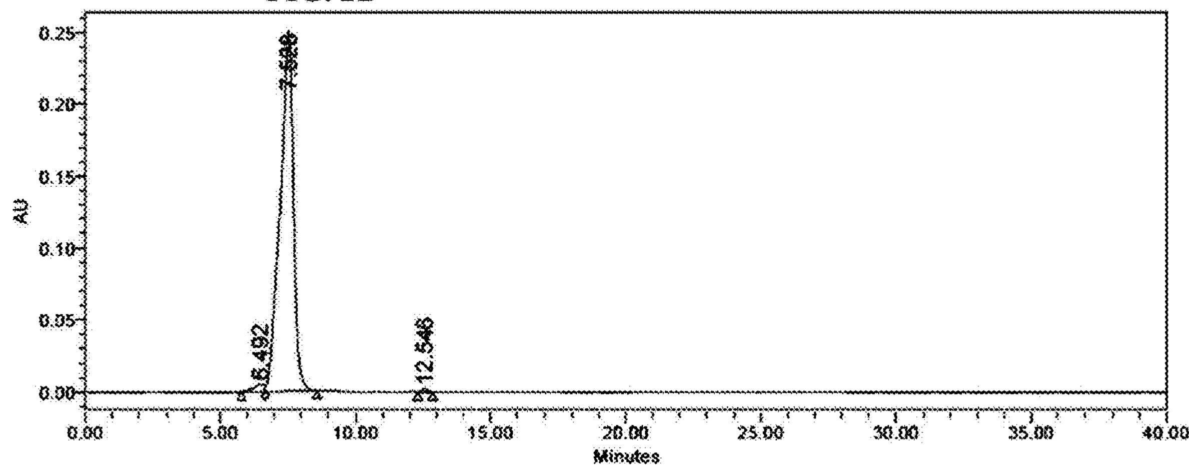
FIG. 2B shows size exclusion chromatography (SEC) analysis of the obtained hCD80-Fc fusion protein dimer.

Then, absorbance at a wavelength of 280 nm over time was measured by using size exclusion chromatography with TSKgel G3000SWXL column (TOSOH Bioscience) to obtain a high concentration of fusion protein. At this time, the isolated and purified fusion protein was subjected to SDS-PAGE under the reducing (R) or non-reducing (NR) conditions, and stained with coomassie blue to confirm its purity (FIG. 2A). As a result, it was confirmed that the fusion protein forms a dimer. Also, the result analyzed using size exclusion chromatography is as shown in FIG. 2B.

Preparation Example 1. Culture Composition for Culturing Regulatory T Cells

Preparation Example 1.1. CD4+ Cell Culture Composition

A CD4+ cell culture medium was prepared as the following composition. At this time, a medium of the basic components was prepared, and then additive components GI-101, GI-101WT, hCD80-Fc, Fc-IL-2v2, or Fc-IL-2 wt were added prior to use.

TABLE 1

| Components | | | | | Final |
|---|---|---|---|---|---|
| | Components | Manufacturer | Cat.# | Dose | concentration |
| Basic component | RPMI1640 medium | Welgene | LM 011-01 | to 500 mL | |
| | FBS | Hyclone | SH30084.03 | 50 mL | 10% |
| | HEPES | Welgene | BB 001-01 | 5 mL | 10 mM |
| | Penicillin & Streptomycin | Welgene | LS 202-02 | 5 mL | Penicillin: 100 U/ml Streptomycin: 100 μg/ml |
| | Sodium pyruvate | Welgene | LS 013-01 | 5 mL | 1 mM |
| | MEM Non-Essential Amino Acids Solution | GIBCO | 11140050 | 5 mL | 1 mM |
| | L-Glutamine | GIBCO | 25030149 | 5 mL | 2 mM |
| | 2-Mercaptoethanol | GIBCO | 21985-023 | 0.5 mL | 55 μM |
| Additive component | GI-101 | GI-Innovation | — | adding immediately before use | 3.2 nM, 50 nM |
| | GI-101_WT | GI-Cell | — | | 3.2 nM, 50 nM |
| | hCD80-Fc | GI-Cell | — | | 3.2 nM, 50 nM |
| | Fc-IL-2v2 | GI-Cell | — | | 3.2 nM, 50 nM |
| | Fc-IL-2wt | GI-Cell | — | | 3.2 nM, 50 nM |

TABLE 2

| Components | | | | | Final |
|---|---|---|---|---|---|
| | Components | Manufacturer | Cat.# | Dose | concentration |
| Basic component | TexMACS medium | Miltenyi Biotec | 170-076-307 | to 1000 mL | |
| | Human AB serum | Sigma | H4522 | 50 mL | 5% |
| | Penicillin& Streptomycin | Welgene | LS 202-02 | 10 mL | 100 U/ml (Penicillin) and 100 μg/ml (Streptomycin) |

TABLE 2-continued

| Components | | | | | Final |
|---|---|---|---|---|---|
| Components | | Manufacturer | Cat.# | Dose | concentration |
| Additive component | GI-101 | GI-Innovation | — | adding immediately before use | 3.2 nM, 50 nM |
| | GI-101_WT | GI-Cell | — | | 3.2 nM, 50 nM |
| | hCD80-Fc | GI-Cell | — | | 3.2 nM, 50 nM |
| | Fc-IL-2v2 | GI-Cell | — | | 3.2 nM, 50 nM |
| | Fc-IL-2wt | GI-Cell | — | | 3.2 nM, 50 nM |

Preparation Example 1.2. CD4+CD25+CD127− Cell Culture Composition

A CD4+CD25+CD127− cell culture medium was prepared as follows.

TABLE 3

| Components | | | | | Final |
|---|---|---|---|---|---|
| Components | | Manufacturer | Cat.# | Dose | concentration |
| Basic component | RPMI1640 medium | Welgene | LM 011-01 | to 500 mL | |
| | FBS | Hyclone | SH30084.03 | 50 ml | 10% |
| | HEPES | Welgene | BB 001-01 | 5 mL | 10 mM |
| | Penicillin & Streptomycin | Welgene | LS 202-02 | 5 mL | Penicillin: 100 U/ml Streptomycin: 100 μg/ml |
| | Sodium pyruvate | Welgene | LS 013-01 | 5 mL | 1 mM |
| | MEM Non-Essential Amino Acids Solution | GIBCO | 11140050 | 5 mL | 1 mM |
| | L-Glutamine | GIBCO | 25030149 | 5 mL | 2 mM |
| | 2-Mercaptoethanol | GIBCO | 21985-023 | 0.5 mL | 55 μM |
| Additive component | GI-101 | GI-Innovation | — | adding immediately before use | 3.2 nM, 50 nM |
| | GI-101_WT | GI-Cell | — | | 3.2 nM, 50 nM |
| | hCD80-Fc | GI-Cell | — | | 3.2 nM, 50 nM |
| | Fc-IL-2v2 | GI-Innovation | — | | 3.2 nM, 50 nM |
| | Fc-IL-2wt | GI-Cell | — | | 3.2 nM, 50 nM |

TABLE 4

| Components | | | | | Final |
|---|---|---|---|---|---|
| Components | | Manufacturer | Cat.# | Dose | concentration |
| Basic component | TexMACS medium | Miltenyi Biotec | 170-076-307 | to 1000 mL | |
| | Human AB serum | Sigma | H4522 | 50 mL | 5% |
| | Penicillin& Streptomycin | Welgene | LS 202-02 | 10 mL | 100 U/ml (Penicillin) and 100 μg/ml (Streptomycin) |
| Additive component | GI-101 | GI-Innovation | — | adding immediately before use | 3.2 nM, 50 nM |
| | GI-101_WT | GI-Cell | — | | 3.2 nM, 50 nM |
| | hCD80-Fc | GI-Cell | — | | 3.2 nM, 50 nM |
| | Fc-IL-2v2 | GI-Cell | — | | 3.2 nM, 50 nM |
| | Fc-IL-2wt | GI-Cell | — | | 3.2 nM, 50 nM |

Example 1. Determination of the Degree of Regulatory T Cell Proliferation by a Fusion Protein Dimer Containing an IL-2 Protein and a CD80 Protein Example 1.1. Preparation of Beads for Stimulating the Proliferation of Regulatory T Cells In order to stimulate the proliferation of regulatory T cells in isolated CD4+ cells, beads for stimulating the proliferation of regulatory T cells were prepared using MACS GMP ExpAct Treg Kit (Cat #:170-076-119) (Miltenyi Biotec, Bergisch Gladbach, Germany). Specifically, a reagent in the MACS GMP ExpAct Treg Kit which comprises beads for stimulating the proliferation of regulatory T cells was transferred to a new tube, and the tube was allowed to sit on a magnet for 1 minute, and then the supernatant was removed to separate the beads. At this time, 1 μl of the reagent in the MACS GMP ExpAct Treg Kit was used per $2\times10^5$ cells. After isolating the beads, 0.5 mL to 1 mL of the CD4+ cell culture composition in Table 1 or Table 2 that does not comprise any additive component (comprising only the basic components) was added to resuspend the beads.

Example 1.2. Isolation of CD4+ T Cells

The number of purchased PBMCs (Cat #: SER-PBMC-200-F) (Zen-Bio. Inc, NC 27709, USA) was measured. Then, it was centrifuged at 300×g for 10 minutes. Next, after removing the supernatant buffer solution, 80 μl of MACs buffer per $1\times10^7$ cells was added to resuspend the cell pellets. Then, 20 μl of CD4 MicroBeads (Cat #: 130-045-101) (Miltenyi Biotec, Bergisch Gladbach, Germany) per $1\times10^7$ cells was dispensed, tapped, and sufficiently mixed. Next, it was reacted at 4° C. to 8° C. for 15 minutes.

For washing, 10 mL of MACs buffer was added, and then centrifuged at 300×g for 10 minutes. Then, after removing the supernatant, 500 μl of MACs buffer per $1\times10^8$ cells was added to resuspend the cells pellets. Next, an LS column was prepared, and then 3 mL of MACs buffer was flowed. The cell suspension prepared above was passed through the LS column (Cat #: 130-042-401) (Miltenyi Biotec, Bergisch Gladbach, Germany). 3 mL of MACs buffer was flowed 3 times so that cells attached to the LS Column could be sufficiently washed. Then, after isolating the LS column from a magnet stand, 3 mL of MACs buffer was added, and pressure was applied with a piston to recover CD4+ cells. Next, it was centrifuged at 300×g for 5 minutes. Then, the supernatant was removed, and then the number of cells was measured.

In addition, a regulatory T cell culture solution comprising beads prepared in Example 1.1 was inoculated onto the CD4+ T cells isolated above.

Example 1.3. CD4+ T Cell Culture

In a 6-well plate, the CD4+ cells prepared in Example 1.2 were seeded at $1\times10^7$ cells/mL, and the CD4+ cells were cultured under the condition of a cell culture composition in Table 1 or Table 2 respectively comprising GI-101 (50 nM), GI-101 WT (50 nM), CD80-Fc dimer (50 nM)+Fc-IL-2v2 dimer (50 nM), or CD80-Fc dimer (50 nM)+Fc-IL-2 wt dimer (50 nM) as additives. When cells in the 6-well plate showed more than 80% confluency, they were subcultured into a 25T flask. When the cells in the 25T flask showed more than 80% confluency, they were subcultured into a 75T flask. Finally, when the cells in the 75T flask showed more than 80% confluency, they were obtained.

Example 1.4. CD4+CD25+CD127− Cell Isolation

The CD4+ cells recovered in Example 1.3 were centrifuged at 1,300 rpm and 4° C. for 5 minutes. In addition, the supernatant was removed. 1 mL of Fc block (biolegend, cat #422302) diluted in FACS buffer to 1:200 was added and left on ice for 10 minutes, and then 50 μl of CD4-Pacific Blue (BioLegend, cat #317429), 50 μl of CD25-PE/Cy7 (BioLegend, cat #356108), and 50 μl of CD127-PE (BD, cat #557938) were added, and left on ice for 20 minutes. Then, 4 mL of FACS buffer was further added and centrifuged at 1,300 rpm and 4° C. for 5 minutes. Then, after removing the supernatant, 3 mL of FACS buffer was added and centrifuged at 1,300 rpm and 4° C. for 5 minutes. Next, the supernatant was removed and 3 mL of FACS buffer was added to resuspend the cells. Finally, CD4+CD25+CD127− cells were isolated using BD FACS Aria.

Example 1.5. CD4+CD25+CD127− Cell Culture

The CD4+CD25+CD127− cells isolated in Example 1.4 were seeded at $3\times10^5$ cells/mL in a 48-well plate, and at the same time, beads were isolated from 1 μl of a MACS GMP ExpAct Treg Kit (Cat #:170-076-119) (Miltenyi Biotec, Bergisch Gladbach, Germany) per $2\times10^5$ cells to stimulate the proliferation of regulatory T cells, as Example 1.1. The isolated beads were resuspended into the cell culture composition (0.5 mL to 1 mL) in Table 3 or Table 4 (comprising only the basic components) that does not comprise any additive component, and then added to a well plate in which the CD4+CD25+CD127− cells obtained in Example 1.4 were seeded. Then, CD4+CD25+CD127− cells were cultured under the condition of a cell culture composition in Table 3 or Table 4 respectively comprising GI-101 (50 nM), GI-101 WT (50 nM), CD80-Fc (50 nM)+Fc-IL-2v2 (50 nM), or CD80-Fc (50 nM)+Fc-IL-2 wt (50 nM) as an additive.

In culture, when the cells showed more than 80% confluency in a 48-well plate, they were subcultured into a 24-well plate. When the cells showed more than 80% confluency in the 24-well plate, they were subcultured into a 12-well plate. When the cells showed more than 80% confluency in the 12-well plate, they were subcultured into a 6-well plate. When the cells showed more than 80% confluency in the 6-well plate, they were subcultured into a 25T plate. When the cells in the 25T flask showed more than 80% confluency, they were subcultured into a 75T flask. The cells were finally obtained when they showed more than 80% confluency after subculture in the 75T flask.

Figure 6:
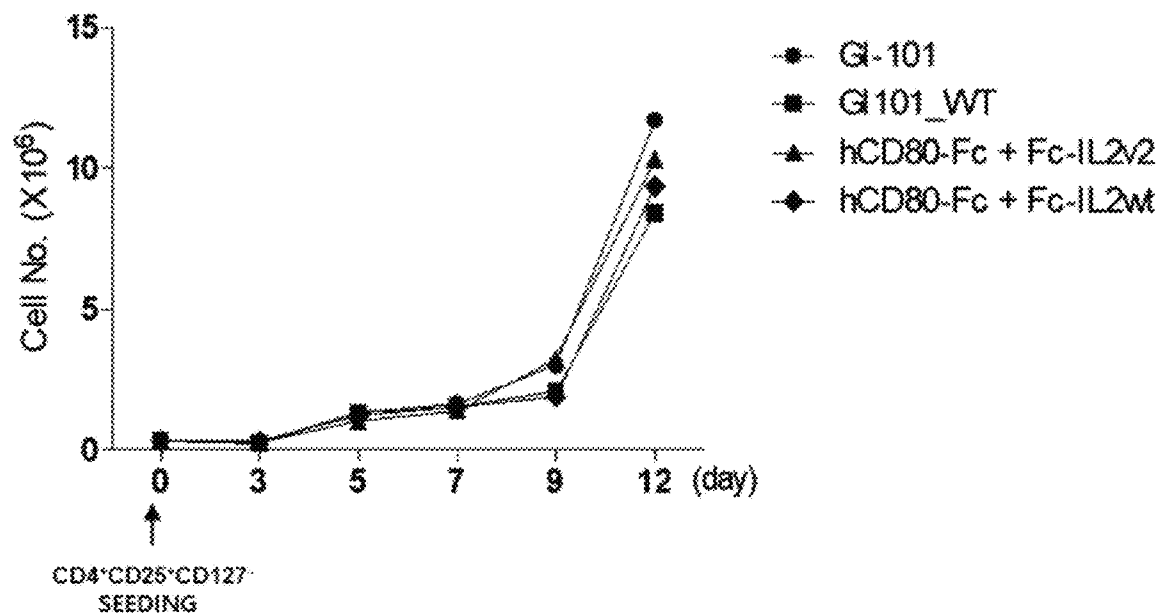
FIG. 6 shows the number of regulatory T cells cultured in a RPMI1640 medium-containing composition.
Figure 7:
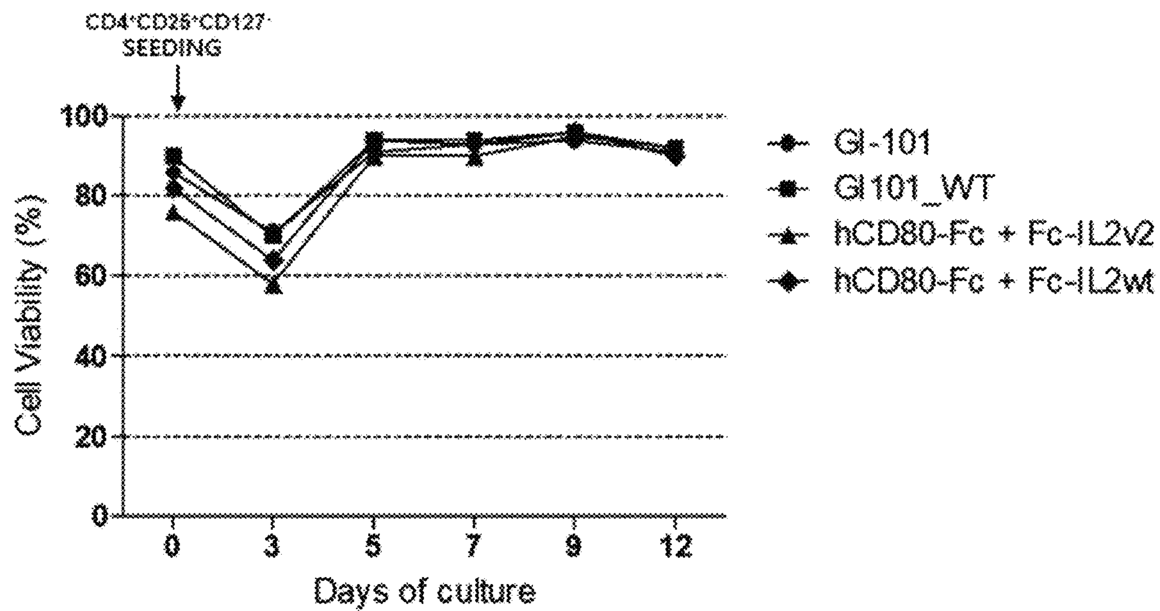
FIG. 7 shows the viability of regulatory T cells cultured in a RPMI1640 medium-containing composition.
Figure 8:
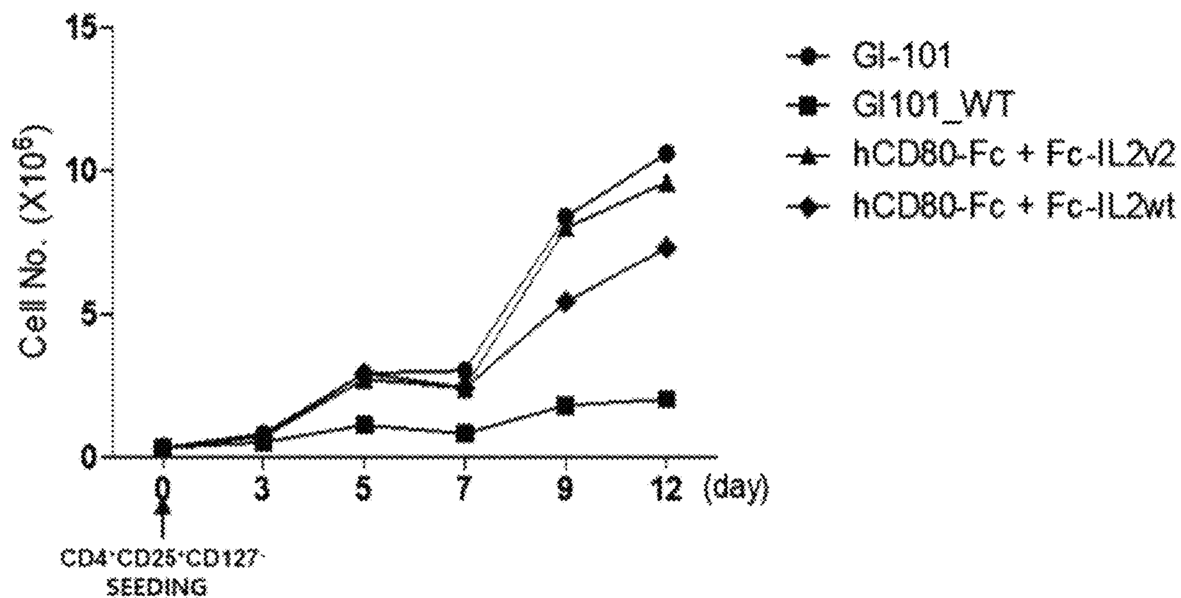
FIG. 8 shows the number of regulatory T cells cultured in a TexMACS medium-containing composition.
Figure 9:
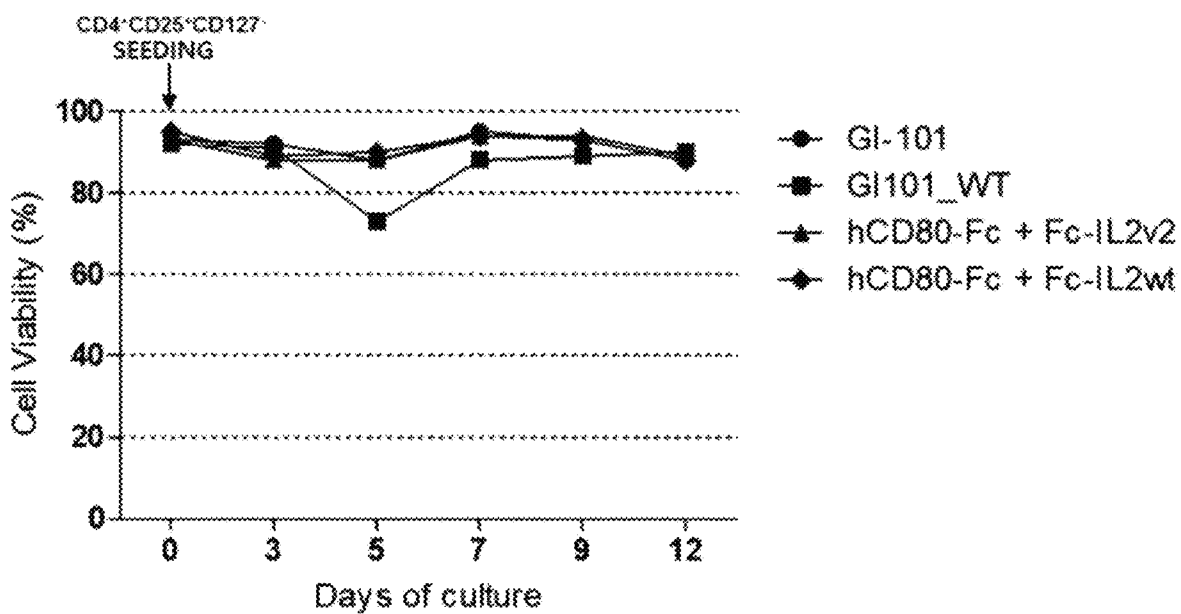
FIG. 9 shows the viability of regulatory T cells cultured in a TexMACS medium-containing composition.

As a result, the results of the proliferation of regulatory T cells in the regulatory T cell culture medium composition comprising the RPMI1640 medium are as shown in Table 5 and FIG. 6, and the cell viabilities are as shown in Table 6 and FIG. 7. In addition, the results of the proliferation of regulatory T cells in the TexMACS medium-containing culture composition are shown in Table 7 and FIG. 8, and the cell viabilities are shown in Table 8 and FIG. 9.

TABLE 5

| Number of total cells (×10⁶) | | | | | | | |
|---|---|---|---|---|---|---|---|
| | | Number of CD4+CD25+CD127− cells | | | | | |
| Additive for culture composition | | 0 Day (seeding) | 3 Days | 5 Days | 7 Days | 9 Days | 12 Days |
| 50 nM | GI-101 | 0.3 | 0.26 | 1.3 | 1.6 | 3 | 11.7 |
| 50 nM | GI-101 WT | 0.3 | 0.23 | 1.3 | 1.5 | 2.1 | 8.4 |
| 50 nM | hCD80-Fc+Fc-IL-2_v2 | 0.3 | 0.25 | 1 | 1.4 | 3.2 | 10.3 |
| 50 nM | hCD80-Fc+Fc-IL-2_wt | 0.3 | 0.3 | 1.2 | 1.5 | 1.9 | 9.36 |

TABLE 6

| Additive for culture composition | | Viability of CD4+CD25+CD127− FACS cells | | | | |
|---|---|---|---|---|---|---|
| | | 3 Days | 5 Days | 7 Days | 9 Days | 12 Days |
| 50 nM | GI-101 | 71 | 91 | 93 | 94 | 91 |
| 50 nM | GI-101 WT | 70 | 94 | 94 | 96 | 92 |
| 50 nM | hCD80-Fc+Fc-IL-2_v2 | 58 | 90 | 90 | 95 | 92 |
| 50 nM | hCD80-Fc+Fc-IL-2_wt | 64 | 94 | 93 | 96 | 90 |

TABLE 7

| Number of total cells (×10$^6$) | | | | | | | |
|---|---|---|---|---|---|---|---|
| Additive for culture composition | | 0 Day (seeding) | Number of CD4+CD25+CD127− cells | | | | |
| | | | 3 Days | 5 Days | 7 Days | 9 Days | 12 Days |
| 50 nM | GI-101 | 0.3 | 0.8 | 2.9 | 3 | 8.4 | 10.6 |
| 50 nM | GI-101 WT | 0.3 | 0.5 | 1.1 | 0.8 | 1.8 | 2 |
| 50 nM | hCD80-Fc+Fc-IL-2_v2 | 0.3 | 0.7 | 2.7 | 2.4 | 8 | 9.6 |
| 50 nM | hCD80-Fc+Fc-IL-2_wt | 0.3 | 0.7 | 2.9 | 2.4 | 5.4 | 7.3 |

TABLE 8

| Additive for culture composition | | Viability of CD4+CD25+CD127− FACS cells | | | | |
|---|---|---|---|---|---|---|
| | | 3 Days | 5 Days | 7 Days | 9 Days | 12 Days |
| 50 nM | GI-101 | 92 | 88 | 95 | 93 | 88 |
| 50 nM | GI-101 WT | 91 | 73 | 88 | 89 | 90 |
| 50 nM | hCD80-Fc+Fc-IL-2_v2 | 88 | 88 | 94 | 94 | 89 |
| 50 nM | hCD80-Fc+Fc-IL-2_wt | 89 | 90 | 94 | 93 | 88 |

Example 1.6. Determination of Secretory Capacities of Immunosuppressive Cytokines: Interleukin-10

In order to evaluate the IL-10 secretory capacities of the regulatory T cells obtained in Example 1.5, the cells were cultured so that the number of cells were adjusted to 1×10$^6$ cells/mL, and then the culture supernatant was obtained to be analyzed by ELISA (enzyme-linked immunosorbent assay).

First, 100 μl of incubation buffer of a human IL-10 ELISA Kit (Invitrogen, Cat #KAC1321) was dispensed into each microplate, and then 100 μl of calibration, control, or regulatory T cell culture supernatant sample was added to dispense, respectively. Then, the microplates were covered with an adhesive film and reacted with shaking at 700 rpm at room temperature (18° C. to 25° C.) for 2 hours on a shaker. Then, microwell strips were washed 3 times with about 150 μl of washing buffer per well.

After washing, 100 μl of a specimen diluent was added. Then, 50 μl of anti-IL-10-HRP was added, and then reacted with shaking at 700 rpm at room temperature for 2 hours, followed by washing 3 times with about 150 μl of washing buffer per well. After washing, 100 μl of TMB was added, and then reacted at room temperature for 15 minutes, followed by termination of the reaction by adding 100 μl of stop solution. Then, the fluorescence values of each microwell were measured at 450 nm.

Figure 10:
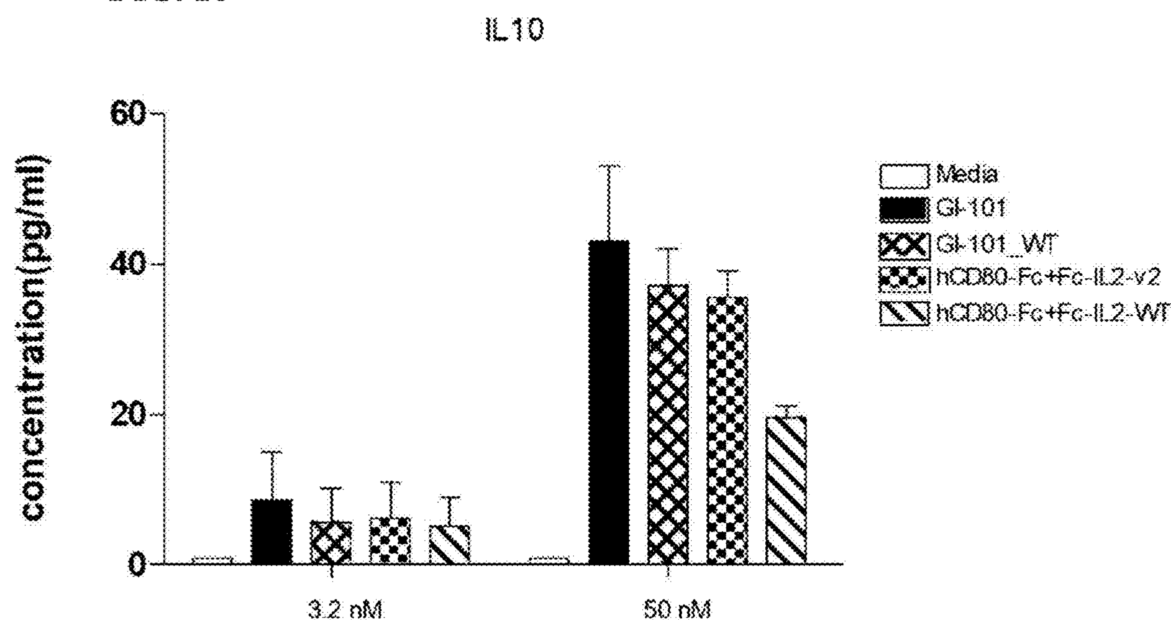
FIG. 10 shows the IL-10 secretory capacity of regulatory T cells cultured using a RPMI1640 medium-containing composition.
Figure 11:
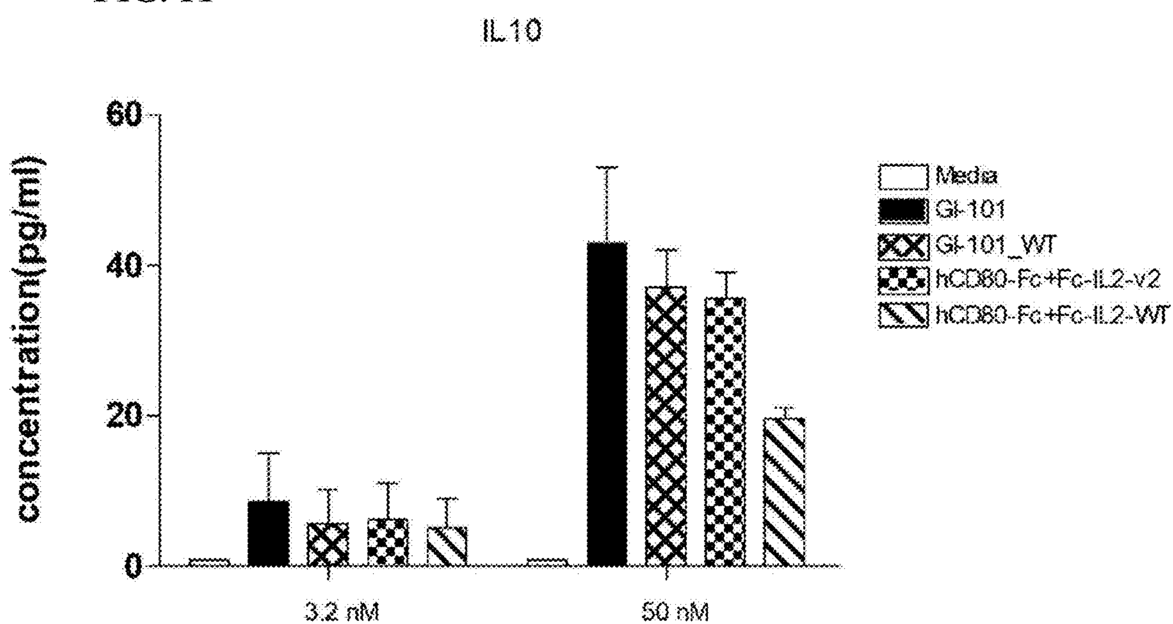
FIG. 11 shows the IL-10 secretory capacity of regulatory T cells cultured using a TexMACS medium-containing composition.

As a result, the interleukin-10 secretory capacities of the cells cultured in the RPMI1640 medium-containing composition are as shown in FIG. 10, and the interleukin-10 secretory capacities of the cells cultured in the TexMACS medium-containing composition are as shown in FIG. 11. It was confirmed by FIGS. 10 and 11 that interleukin-10 was highly expressed in regulatory T cells cultured in the culture composition comprising GI-101.

Example 2. Determination of the Regulatory T Cells Proliferation by GI-101 in Optimized Culture Process

Example 2.1. Isolation of CD4+ T Cells

The number of purchased PBMCs (Cat #: SER-PBMC-200-F) (Zen-Bio. Inc, NC 27709, USA) was measured. Then, it was centrifuged at 300×g for 10 minutes. Then, after removing the supernatant buffer solution, 80 μl of MACs buffer per 1×10$^7$ cells was added to resuspend the cell pellets. Then, 20 μl of CD4 microbeads (Cat #: 130-045-101) (Miltenyi Biotec, Bergisch Gladbach, Germany) per 1×10$^7$ cells was dispensed, tapped, and sufficiently mixed. Next, it was reacted at 4° C. to 8° C. for 15 minutes.

For washing, 10 mL of MACs buffer was added, and then centrifuged at 300×g for 10 minutes. Then, after removing the supernatant, 500 μl of MACs buffer per 1×10$^8$ cells was added to resuspend the cell pellets. Next, an LS column was prepared, and then 3 mL of MACs buffer was flowed. The cell suspension prepared above was passed through the LS column (Cat #: 130-042-401) (Miltenyi Biotec, Bergisch Gladbach, Germany). 3 mL of MACs buffer was flowed 3 times so that cells attached to the LS Column could be sufficiently washed. Then, after isolating the LS column from a magnet stand, 3 mL of MACs buffer was added, and pressure was applied with a piston to recover CD4+ cells. Then, it was centrifuged at 300×g for 5 minutes. After centrifugation, the supernatant was removed, and the number of cells was measured.

In order to stimulate the proliferation of regulatory T cells in the isolated CD4+ cells, 0.5 mL to 1 mL of the CD4+ cell culture compositions in Table 1 or Table 2 (comprising only the basic components) that does not comprise any additive component was added to resuspend beads which were isolated and prepared as Example 1.1, and this was inoculated into CD4+ cells isolated from the PBMCs.

Example 2.2. CD4+ T Cell Culture

In a 6-well plate, the CD4+ cells prepared in Example 2.1 were seeded at $1\times10^7$ cells/mL, and were cultured under the condition of the cell culture composition in Table 1 or Table 2 respectively comprising GI-101 (3.2 nM/50 nM), GI-101 WT (3.2 nM/50 nM), CD80-Fc dimer (3.2 nM/50 nM)+Fc-IL-2v2 dimer (3.2 nM/50 nM), or CD80-Fc dimer (3.2 nM/50 nM)+Fc-IL-2 wt dimer (3.2 nM/50 nM) as an additive. When the cells showed more than 80% confluency in the 6-well plate, they were subcultured into a 25T plate. When the cells in the 25T flask showed more than 80% confluency, they were subcultured into a 75T flask. Finally, when the cells in the 75T flask showed more than 80% confluency, they were obtained.

Example 2.3. CD4+CD25+CD127− T Cell Isolation

The CD4+ cells recovered in Example 2.2 were centrifuged at 1,300 rpm and 4° C. for 5 minutes. In addition, the supernatant was removed, and 1 mL of Fc block (biolegend, cat #422302) diluted in FACS buffer to 1:200 was added, followed by leaving on ice for 10 minutes. 50 μl of CD4-Pacific Blue (BioLegend, cat #317429), 50 μl of CD25-PE/Cy7 (BioLegend, cat #356108), and 50 μl of CD127-PE (BD, cat #557938) were added to Sample 2, and left on ice for 20 minutes.

Then, 4 mL of FACS buffer was further added and centrifuged at 1,300 rpm and 4° C. for 5 minutes. Next, the supernatant was removed, and 3 mL of FACS buffer was added, followed by centrifugation at 1,300 rpm and 4° C. for 5 minutes. Then, the supernatant was removed and 3 mL of FACS buffer was added to resuspend the cells. Finally, CD4+CD25+CD127− cells were isolated with BD FACS Aria.

Example 2.4. CD4+CD25+CD127− T Cell Culture

All CD4+CD25+CD127− cells isolated in Example 2.3 were seeded in a 24-well plate, and at the same time, to stimulate the proliferation of regulatory T cells, beads were isolated from 1 μl of a MACS GMP ExpAct Treg Kit (Cat #:170-076-119) (Miltenyi Biotec, Bergisch Gladbach, Germany) per $2\times10^5$ cells, as Example 2.1, and the beads were resuspended into a cell culture composition (0.5 mL to 1 mL) in Table 3 or Table 4 (comprising only the basic components) that does not comprise any additive component. Next, these were added to a well plate in which the CD4+CD25+CD127− cells were seeded.

Then, CD4+CD25+CD127− cells were cultured under the condition of a cell culture composition in Table 3 or Table 4 respectively comprising GI-101 (3.2 nM/50 nM), GI-101_WT (3.2 nM/50 nM), CD80-Fc dimer (3.2 nM/50 nM)+Fc-IL-2v2 dimer (3.2 nM/50 nM), or CD80-Fc dimer (3.2 nM/50 nM)+Fc-IL-2 wt (3.2 nM/50 nM) as an additive. When the cells showed more than 80% confluency in the 24-well plate, they were subcultured into a 12-well plate. When the cells showed more than 80% confluency in the 12-well plate, they were subcultured into a 6-well plate. When the cells showed more than 80% confluency in the 6-well plate, they were subcultured into a 25T plate. When the cells in the 25T flask showed more than 80% confluency, they were subcultured into a 75T flask.

For a group treated with 3.2 nM of additives in Table 3 or Table 4, the cells were finally obtained when they showed more than 80% confluency in the 75T flask. For the group treated with 50 nM of the additives in Table 3 or Table 4, the cells were finally obtained when they showed more than 80% confluency after subculture to a 175T flask.

Figure 12A:
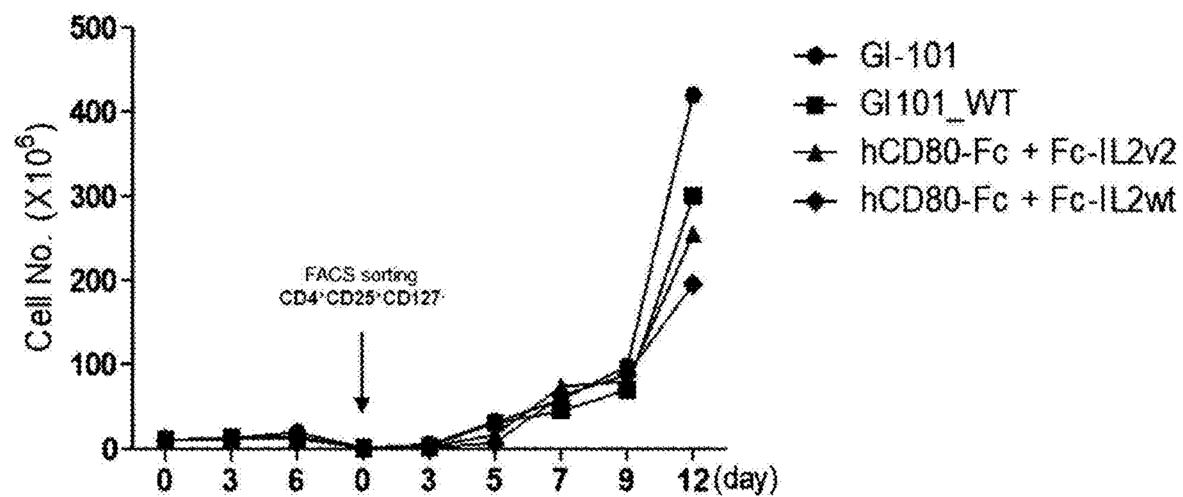
FIGS. 12A and 12B show the number of regulatory T cells proliferated when cultured in a composition containing a RPMI1640 medium in the optimized process.
Figure 12B:
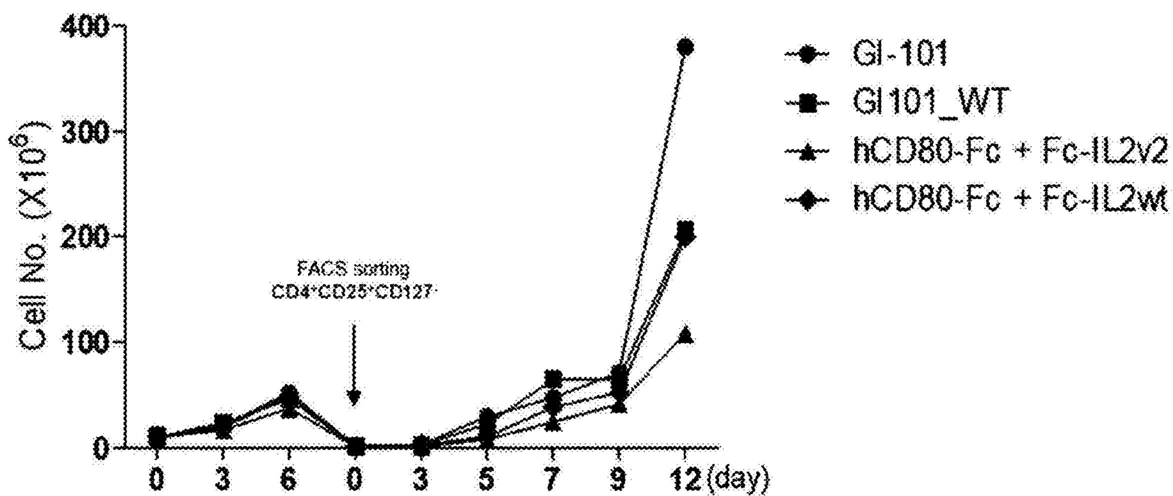
Figure 13A:
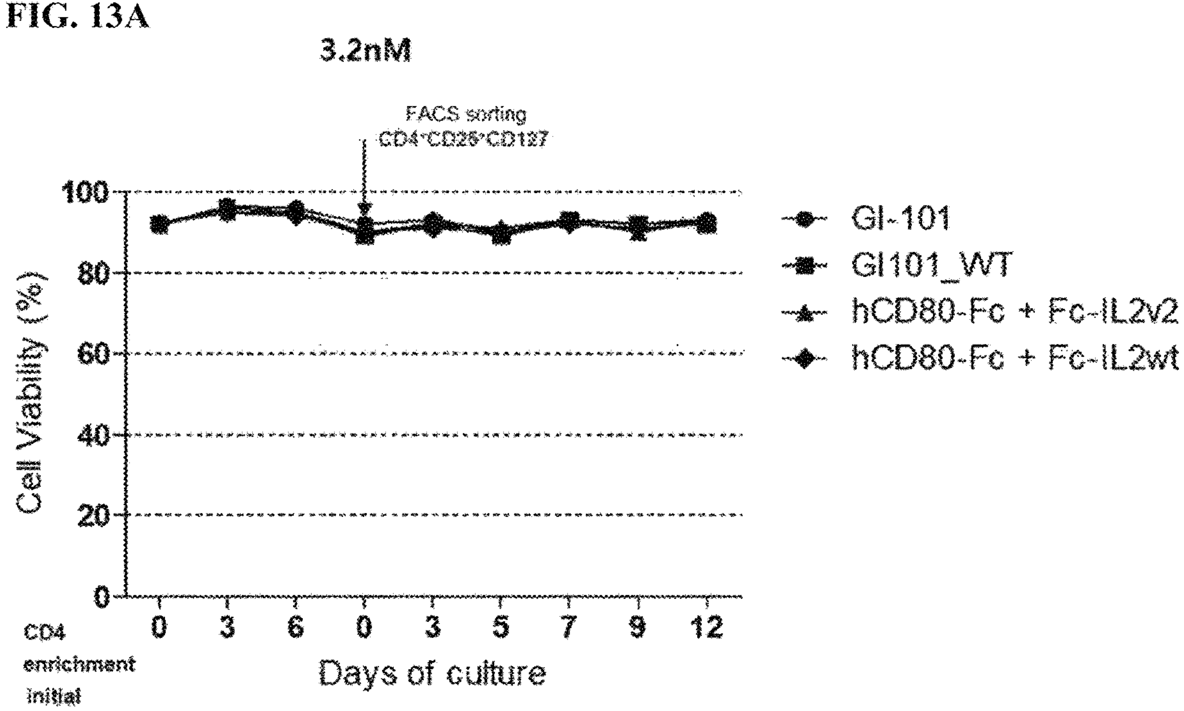
FIGS. 13A and 13B show the viability of regulatory T cells when cultured in a composition containing a RPMI1640 medium in the optimized process.
Figure 13B:
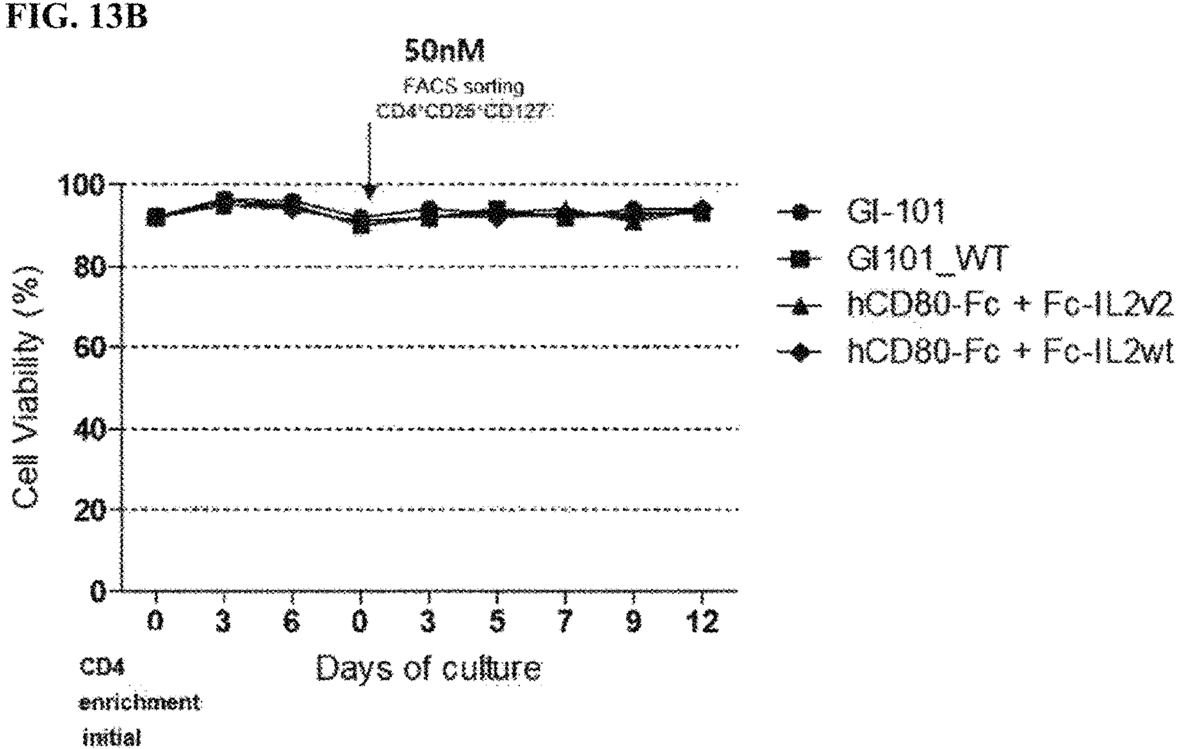
Figure 14A:
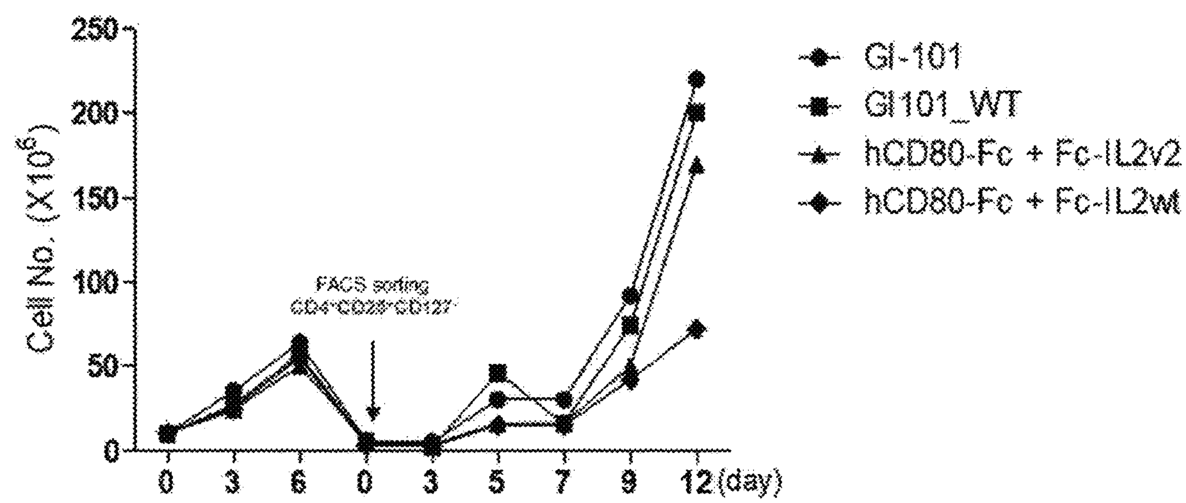
FIGS. 14A and 14B show the number of regulatory T cells when cultured in a composition containing a TexMACS medium in the optimized process.
Figure 14B:
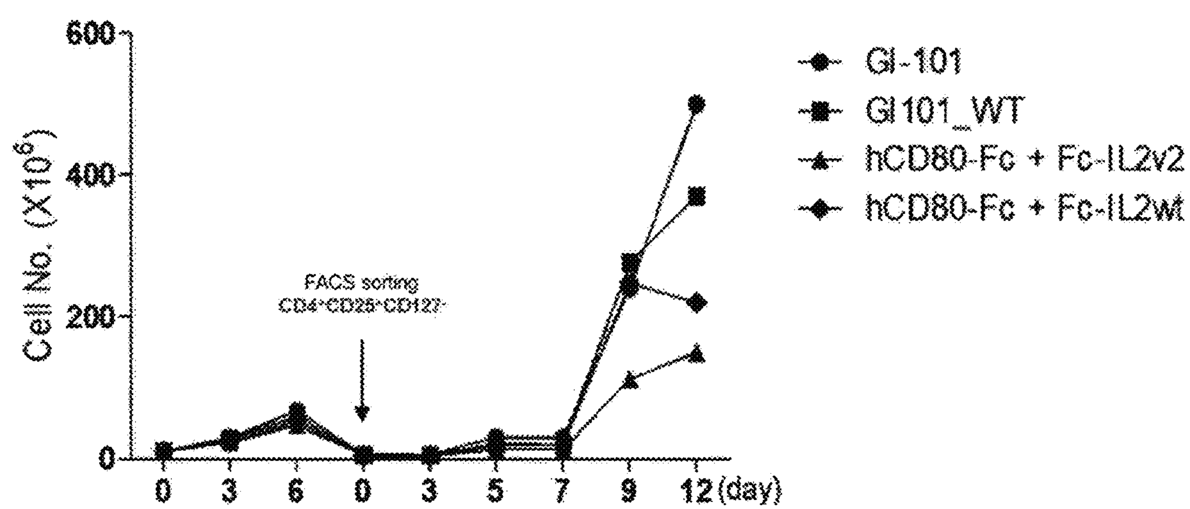
Figure 15A:
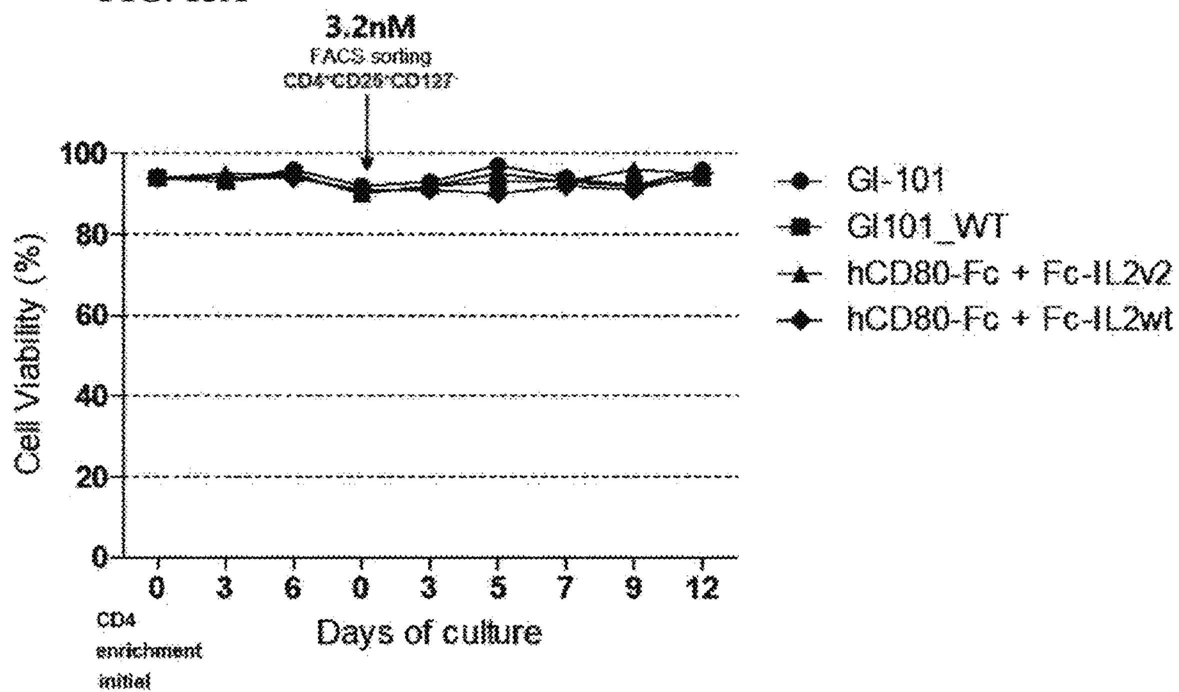
FIGS. 15A and 15B show the viability of regulatory T cells when cultured in a composition containing a TexMACS medium in the optimized process.
Figure 15B:
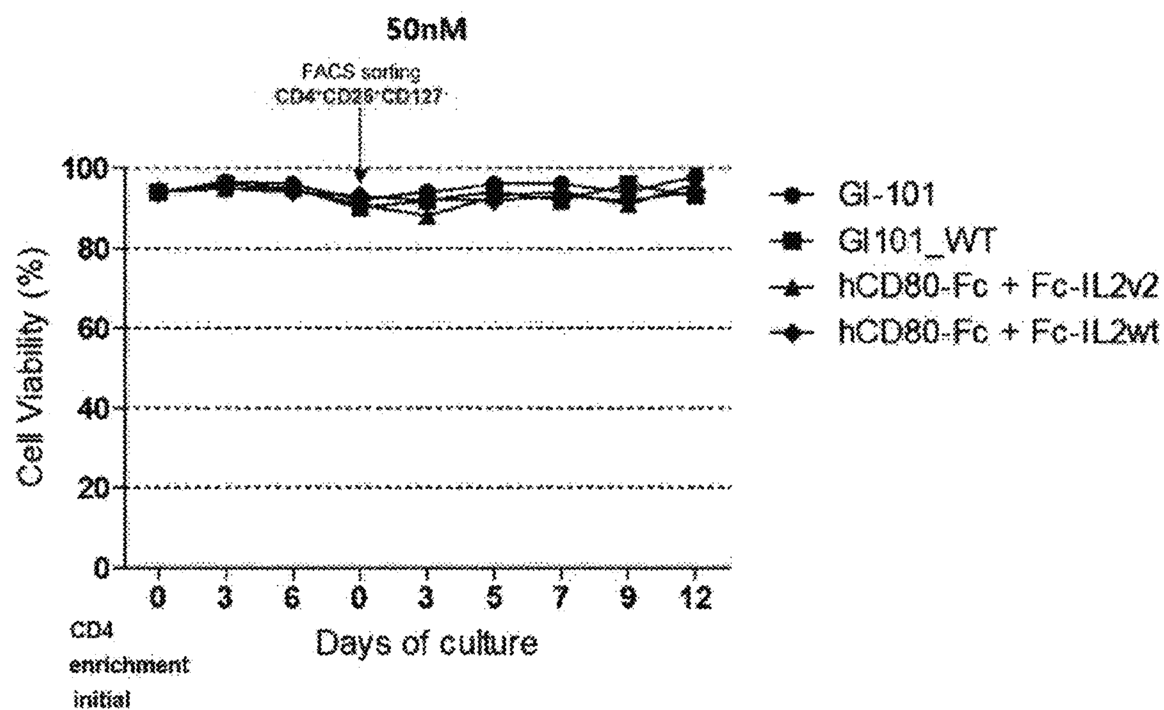

As a result, in a culture composition comprising a RPMI1640 medium, the cell proliferation results are as shown in Table 9, FIG. 12A and FIG. 12B, and the cell viabilities are as shown in Table 10, FIG. 13A and FIG. 13B. In addition, in a culture composition comprising a TexMACS medium, the cell proliferation results are shown in Table 11, FIG. 14A and FIG. 14B, and the cell viabilities are shown in Table 12, FIG. 15A and FIG. 15B.

TABLE 9

| Number of Total cells ($\times10^6$) | | | | | | | | | | |
|---|---|---|---|---|---|---|---|---|---|---|
| | | CD4+ cells | | | Cell number after CD4+CD25+CD127− FACS isolation | | | | | |
| Additive for culture composition | | 0 Day | 3 Days | 6 Days | 0 Day | 3 Days | 5 Days | 7 Days | 9 Days | 12 Days |
| 3.2 nM | GI-101 | 10 | 12.1 | 18.8 | 0.5 | 4.9 | 32 | 58 | 98 | 420 |
| | GI-101 WT | 10 | 13.1 | 12 | 0.6 | 2.77 | 30 | 45 | 70 | 300 |
| | hCD80-Fc+ Fc-IL-2_v2 | 10 | 12.1 | 14.1 | 0.4 | 1.69 | 16 | 74 | 80 | 255 |
| | hCD80-Fc+ Fc-IL-2_wt | 10 | 11.1 | 13.5 | 0.3 | 1.07 | 6.4 | 63 | 88 | 196 |
| 50 nM | GI-101 | 10 | 21 | 51.9 | 1.8 | 2.7 | 29 | 47 | 71 | 380 |
| | GI-101 WT | 10 | 23 | 45.8 | 0.8 | 2.6 | 22 | 64 | 65 | 206 |
| | hCD80-Fc+ Fc-IL-2_v2 | 10 | 16.5 | 37.3 | 0.89 | 0.9 | 7.7 | 24 | 41 | 108 |
| | hCD80-Fc+ Fc-IL-2_wt | 10 | 18.9 | 49.3 | 1.1 | 2.4 | 10 | 38 | 52 | 200 |

TABLE 10

| Cell viability (%) | | | | | | | | | | |
|---|---|---|---|---|---|---|---|---|---|---|
| | | CD4+ cells | | | Cell viability after CD4+CD25+CD127− FACS isolation | | | | | |
| Additive for culture composition | | 0 Day | 3 Days | 6 Days | 0 Day | 3 Days | 5 Days | 7 Days | 9 Days | 12 Days |
| 3.2 nM | GI-101 | 92 | 96.5 | 96 | 92 | 93 | 90 | 93 | 92 | 93 |
| | GI-101 WT | 92 | 96 | 95 | 89 | 92 | 89 | 93 | 92 | 92 |
| | hCD80-Fc+ Fc-IL-2_v2 | 92 | 95 | 95 | 90 | 92 | 91 | 93 | 90 | 93 |
| | hCD80-Fc+ Fc-IL-2_wt | 92 | 95 | 94 | 90 | 91 | 90 | 92 | 91 | 92 |
| 50 nM | GI-101 | 92 | 96.5 | 96 | 92 | 94 | 93 | 92 | 94 | 94 |
| | GI-101 WT | 92 | 96 | 95 | 90 | 92 | 94 | 92 | 93 | 93 |
| | hCD80-Fc+ Fc-IL-2_v2 | 92 | 95 | 95 | 90 | 92 | 93 | 94 | 91 | 94 |
| | hCD80-Fc+ Fc-IL-2_wt | 92 | 95 | 94 | 91 | 92 | 92 | 93 | 92 | 94 |

TABLE 11

| Number of Total cells ($\times 10^6$) | | | | | | | | | | |
|---|---|---|---|---|---|---|---|---|---|---|
| | | CD4+ cells | | | Cell number after CD4+CD25+CD127− FACS isolation | | | | | |
| Additive for culture composition | | 0 Day | 3 Days | 6 Days | 0 Day | 3 Days | 5 Days | 7 Days | 9 Days | 12 Days |
| 3.2 nM | GI-101 | 10 | 35 | 64 | 5.8 | 5.2 | 30 | 30 | 92 | 220 |
| | GI-101 WT | 10 | 27 | 57 | 5 | 2.14 | 46 | 16 | 74 | 200 |
| | hCD80-Fc+ Fc-IL-2_v2 | 10 | 24 | 50 | 5.48 | 3.45 | 16 | 16 | 50 | 170 |
| | hCD80-Fc+ Fc-IL-2_wt | 10 | 25 | 55 | 3.5 | 2.7 | 15 | 15 | 42 | 72 |
| 50 nM | GI-101 | 10 | 30 | 68 | 6.2 | 5.7 | 30.6 | 30 | 240 | 500 |
| | GI-101 WT | 10 | 28 | 60 | 5.4 | 5 | 21 | 20 | 276 | 370 |
| | hCD80-Fc+ Fc-IL-2_v2 | 10 | 23.5 | 48 | 5 | 4.2 | 13.3 | 13.3 | 113 | 150 |
| | hCD80-Fc+ Fc-IL-2_wt | 10 | 24 | 54 | 3.73 | 3.8 | 19 | 19.6 | 248 | 220 |

TABLE 12

| Cell viability (%) | | | | | | | | | | |
|---|---|---|---|---|---|---|---|---|---|---|
| | | CD4+ cells | | | Cell viability after CD4+CD25+CD127− FACS isolation | | | | | |
| Additive for culture composition | | 0 Day | 3 Days | 6 Days | 0 Day | 3 Days | 5 Days | 7 Days | 9 Days | 12 Days |
| 3.2 nM | GI-101 | 94 | 93 | 96 | 92 | 93 | 97 | 94 | 92 | 96 |
| | GI-101 WT | 94 | 93 | 95 | 90 | 92 | 93 | 93 | 92 | 94 |
| | hCD80-Fc+ Fc-IL-2_v2 | 94 | 95 | 95 | 90 | 92 | 95 | 93 | 96 | 95 |
| | hCD80-Fc+ Fc-IL-2_wt | 94 | 94 | 94 | 91 | 91 | 90 | 92 | 91 | 95 |
| 50 nM | GI-101 | 94 | 96.5 | 96 | 92 | 94 | 96 | 96 | 94 | 98 |
| | GI-101 WT | 94 | 96 | 95 | 90 | 92 | 94 | 92 | 96 | 93 |
| | hCD80-Fc+ Fc-IL-2_v2 | 94 | 95 | 95 | 91 | 88 | 93 | 94 | 91 | 96 |
| | hCD80-Fc+ Fc-IL-2_wt | 94 | 95 | 94 | 93 | 92 | 92 | 93 | 92 | 94 |

Example 2.5. Characterization of Cells

The CD4+CD25+CD127− cells recovered in Example 2.4 were centrifuged at 1,300 rpm and 4° C. for 5 minutes. In addition, the supernatant was removed. Then, 100 µl of Fc block (biolegend, cat #422302) diluted in FACS buffer to 1:200 was added and left on ice for 10 minutes, and additionally 2.5 µl of CD4-PerCP-Cy5.5 (eBioscience, cat #45-0048-42), 2.5 µl of CD25-APC/Cy7 (BD, cat #557753), and 2.5 µl of CD127-Brilliant Violet 785 (Biolegend, cat #351330) were added, and left on ice for 20 minutes.

Then, 1 mL of FACS buffer was further added, and centrifuged at 1,300 rpm and 4° C. for 5 minutes. A solution of 1:3 mixture of Fixation/Permeabilization concentrate and Fixation/Permeabilization Diluent was prepared, and 100 µl was added after removing the supernatant from the cells obtained by centrifugation and left on ice for 30 minutes. Then, 1 mL of FACS buffer was further added, and centrifugation was repeated twice at 1,300 rpm and 4° C. for 5 minutes. Next, the supernatant was removed, and 100 µl of FACS buffer and 2.5 µl of Foxp3-Pacific Blue (Biolegend, cat #320116) were added and left on ice for 20 minutes. Then, 1 mL of FACS buffer was further added and centrifuged at 1,300 rpm and 4° C. for 5 minutes. Next, the supernatant was removed and 200 µl of FACS buffer was added to resuspend the cells. Finally, cells were characterized with a Cytek Aurora equipment.

Figure 16A:
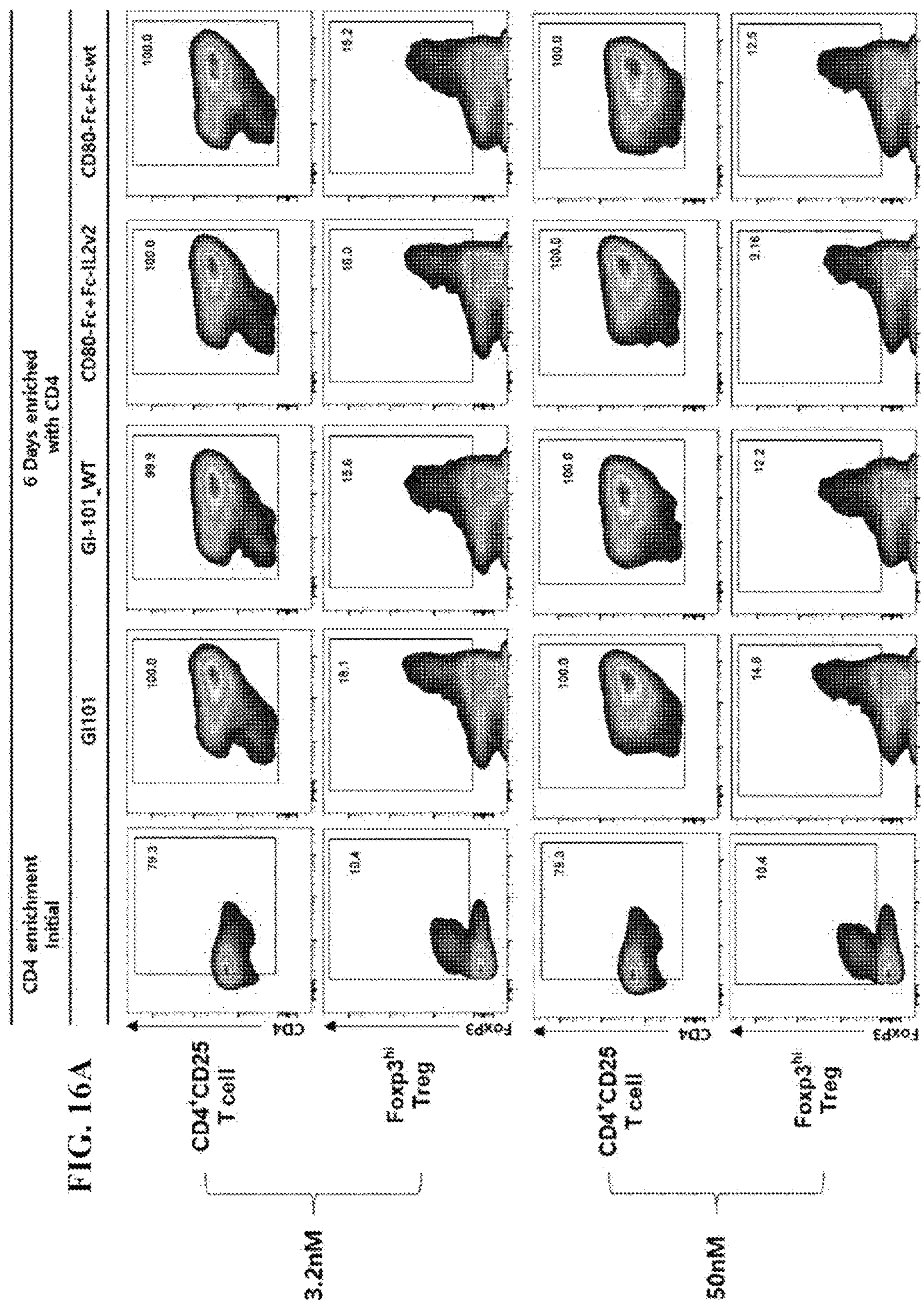
FIGS. 16A to 16C show the results of FACS analysis of the properties of cells cultured in a composition containing a RPMI1640 medium in the optimized process.
Figure 16B:
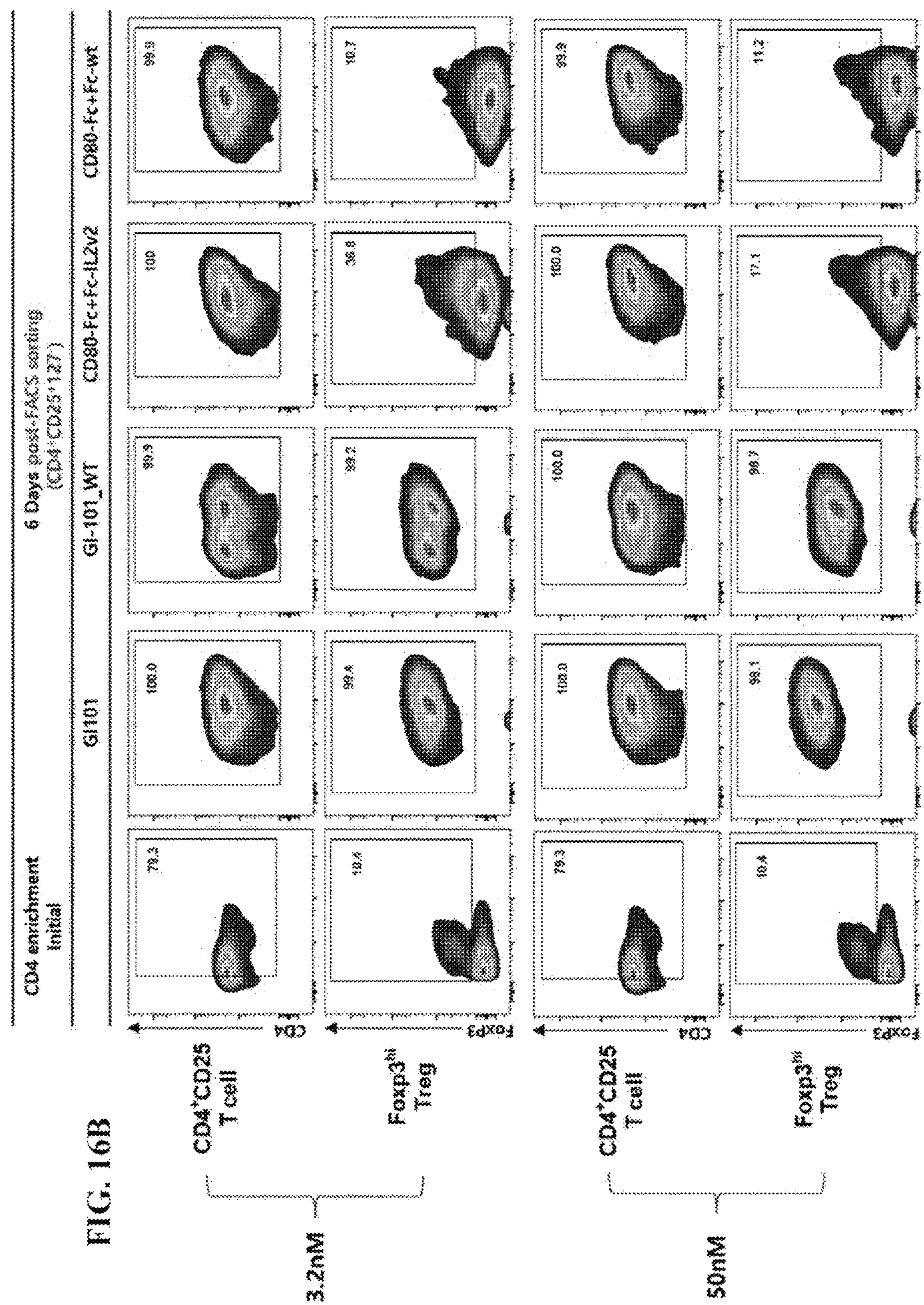
Figure 16C:
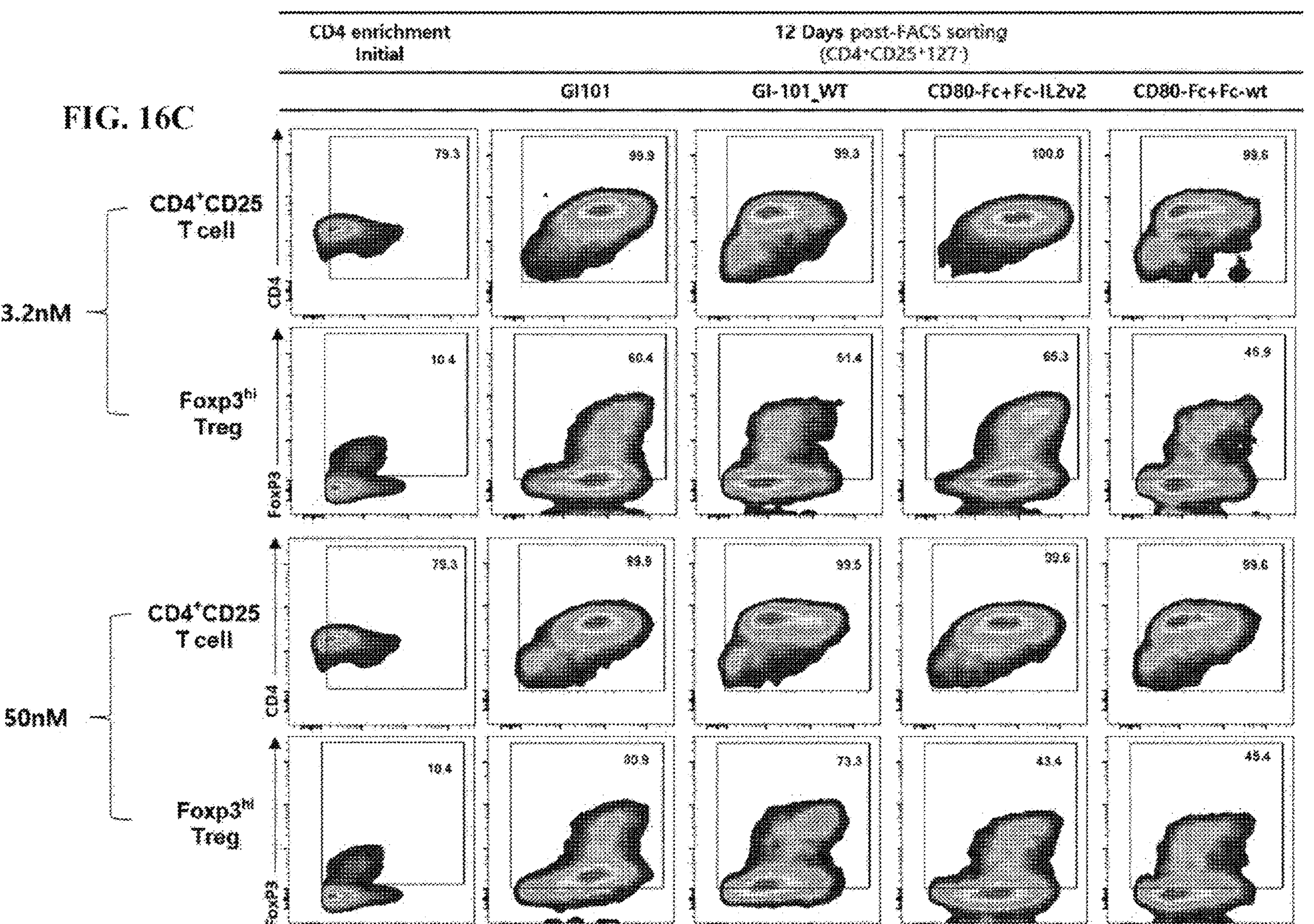
Figure 17A:
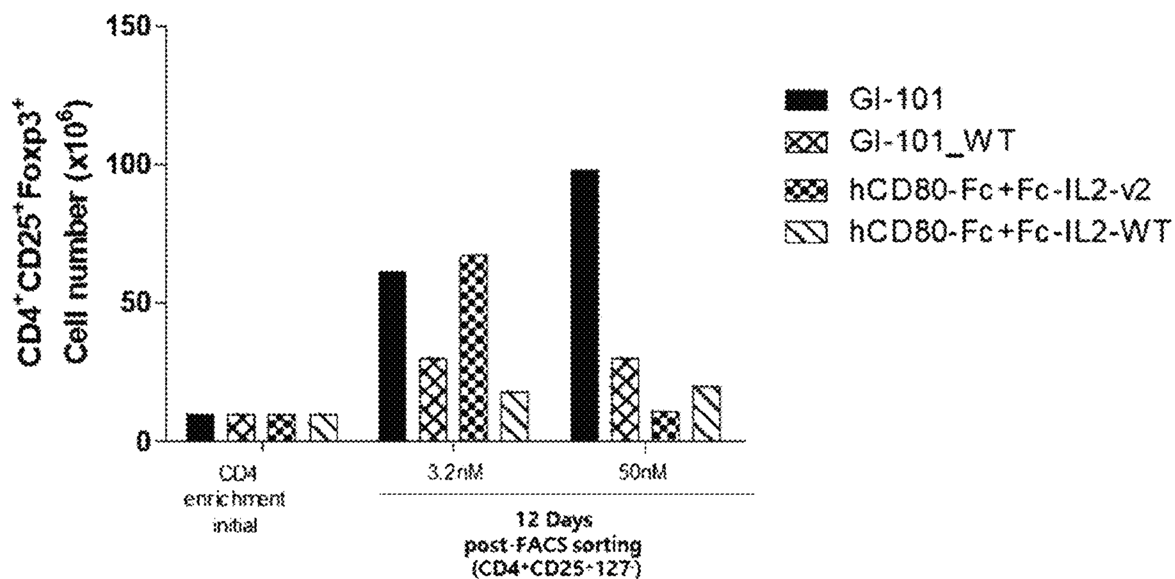
FIGS. 17A to 17C show the number of regulatory T cells expressing Foxp3 when cultured in a composition containing a RPMI1640 medium in the optimized process.
Figure 17B:
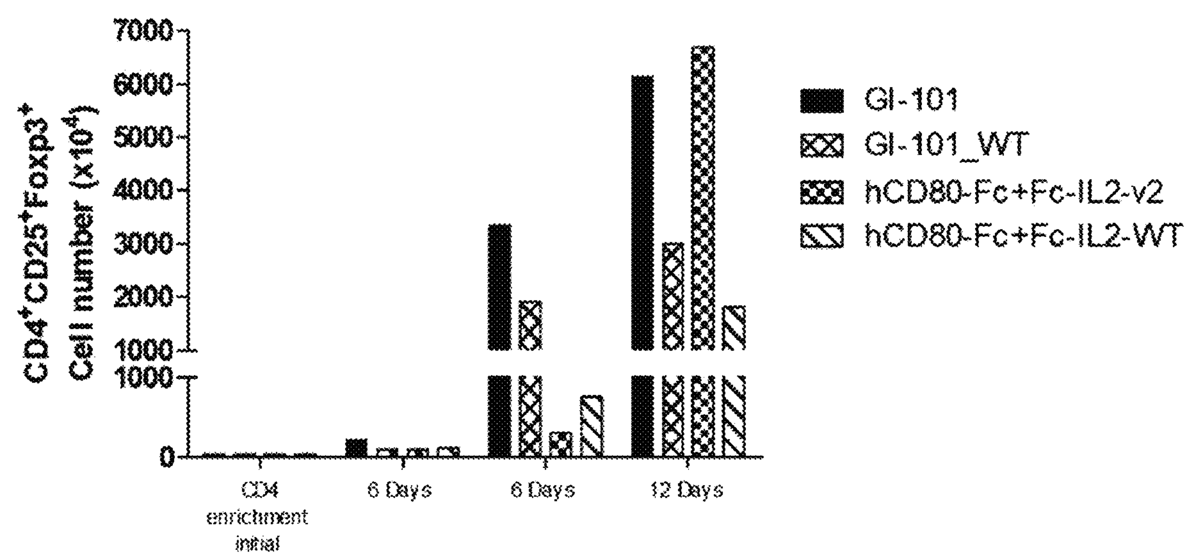
Figure 17C:
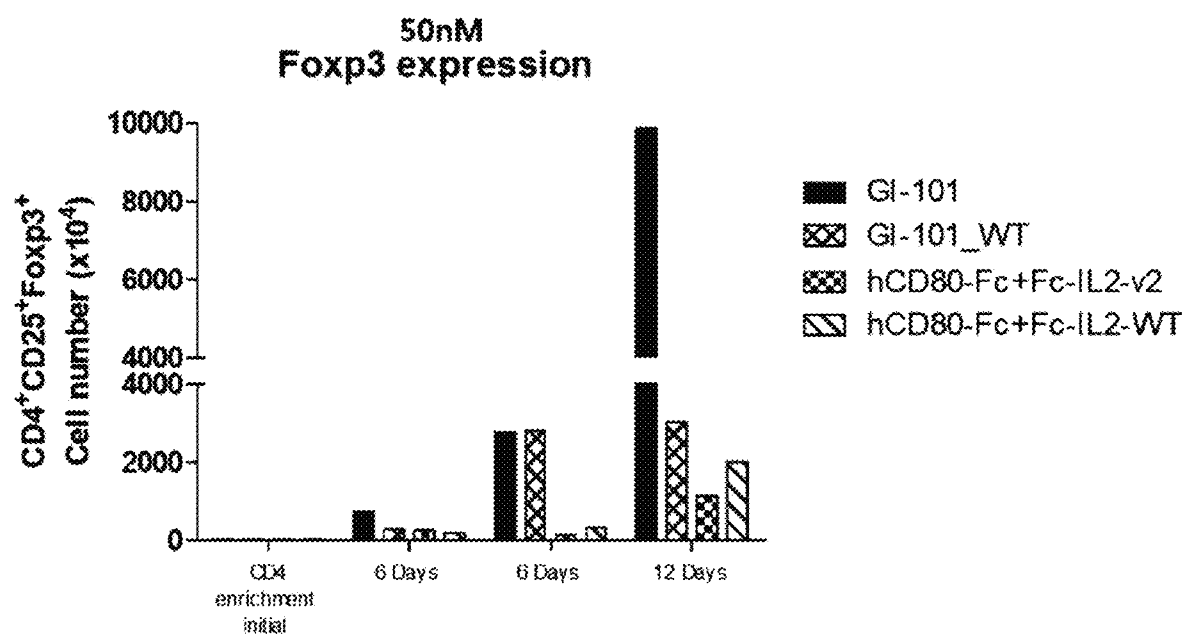
Figure 18A:
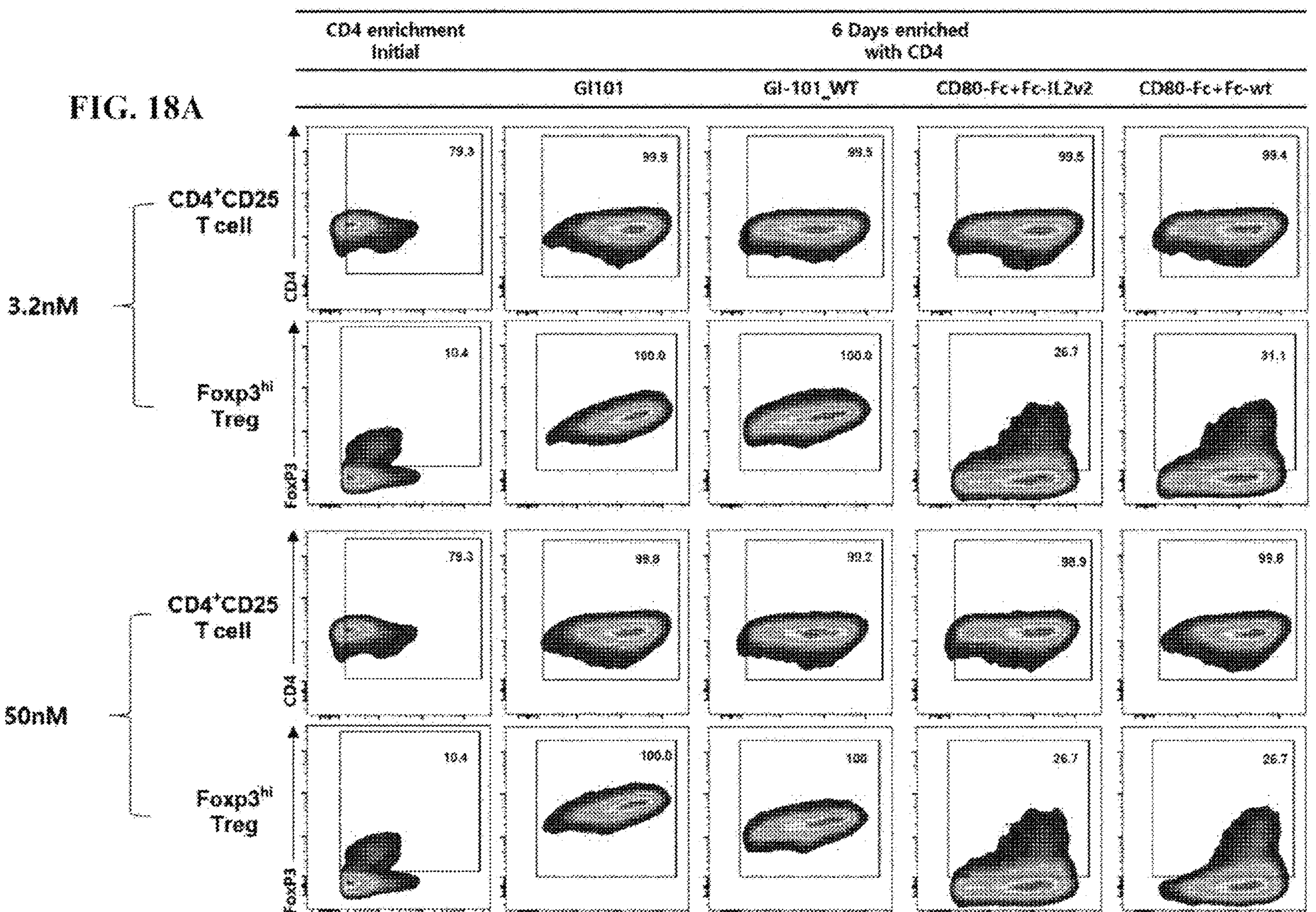
FIGS. 18A to 18C show the results of FACS analysis of the properties of cells cultured in a composition containing a TexMACS medium in the optimized process.
Figure 18B:
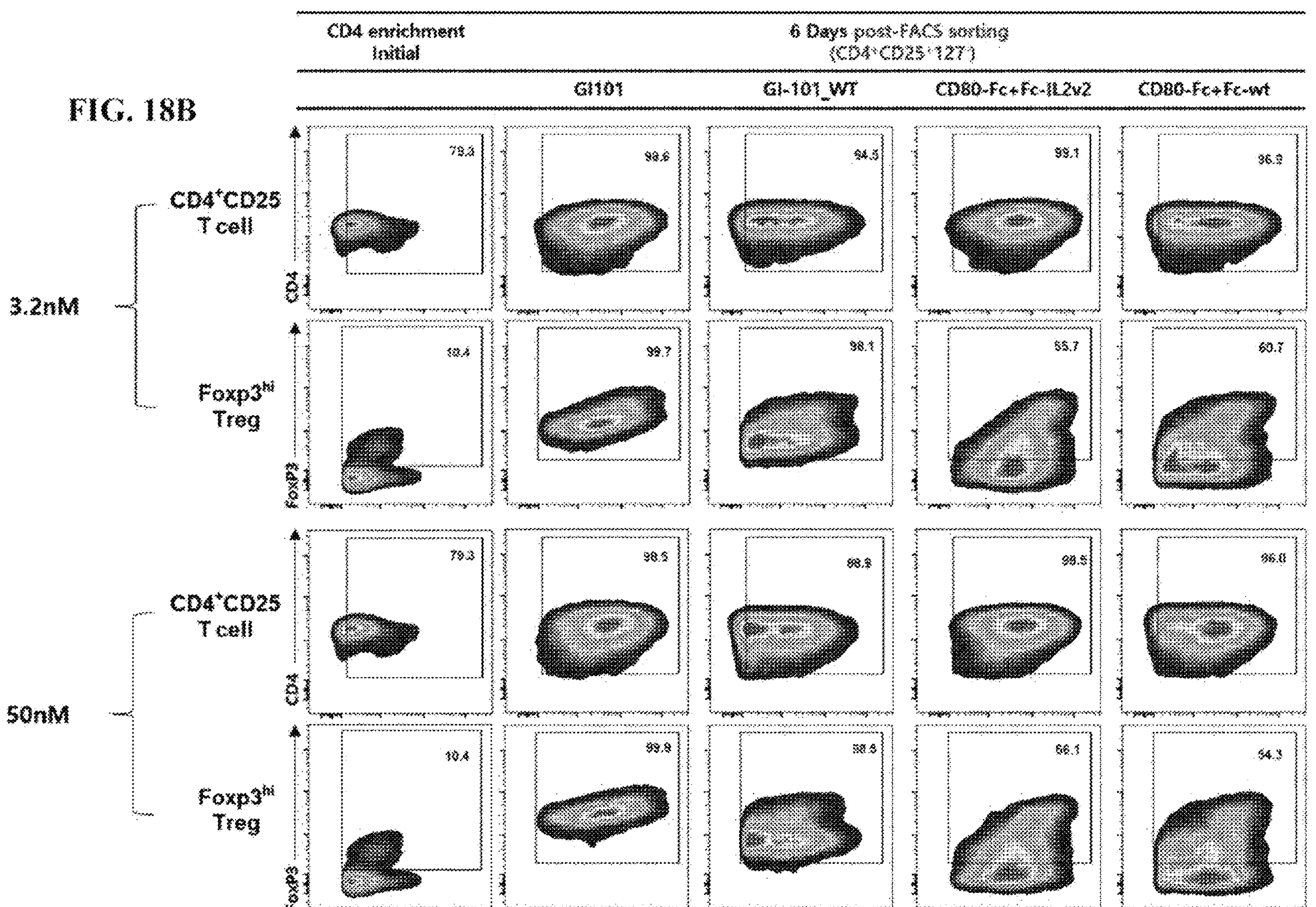
Figure 18C:
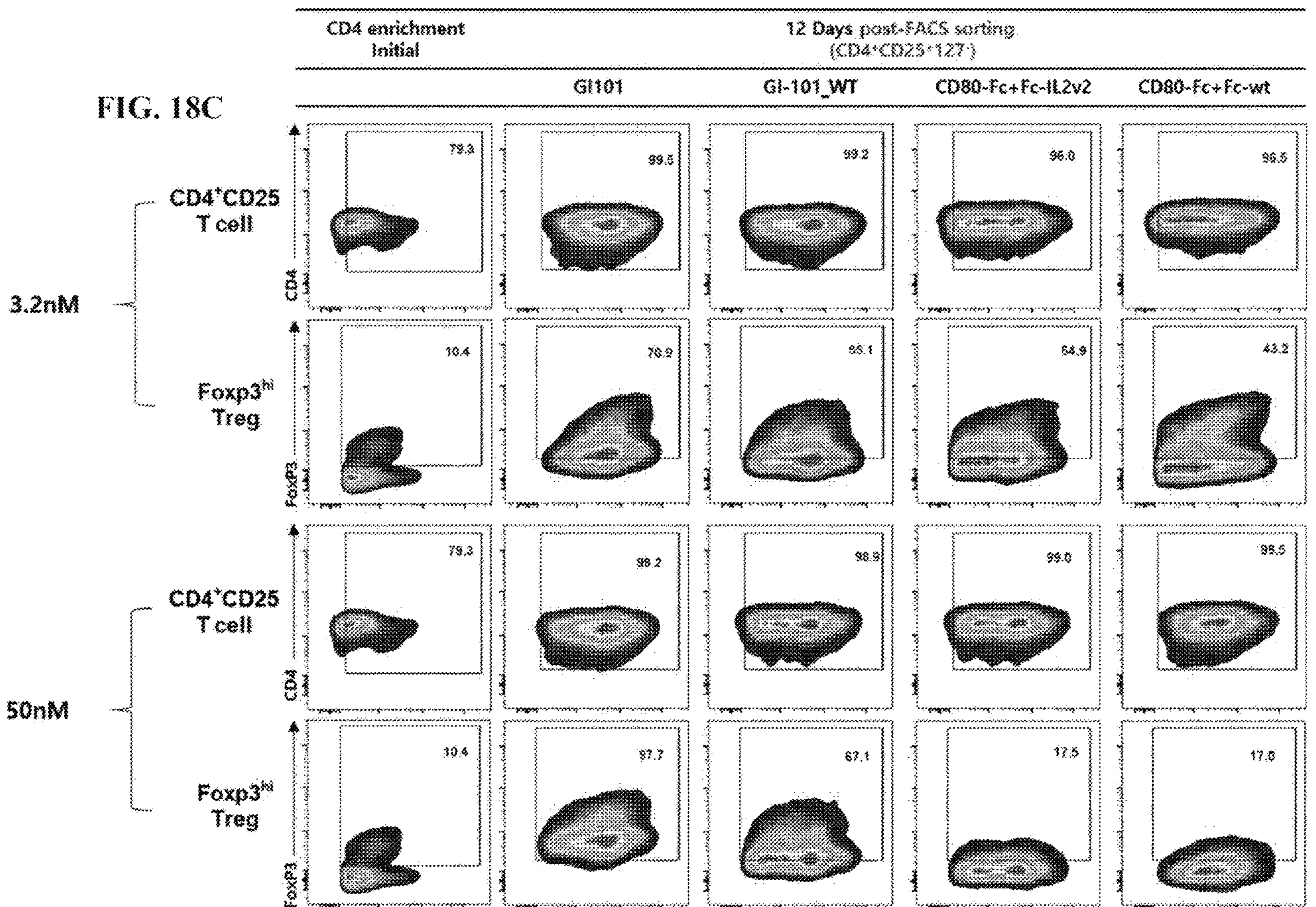
Figure 19A:
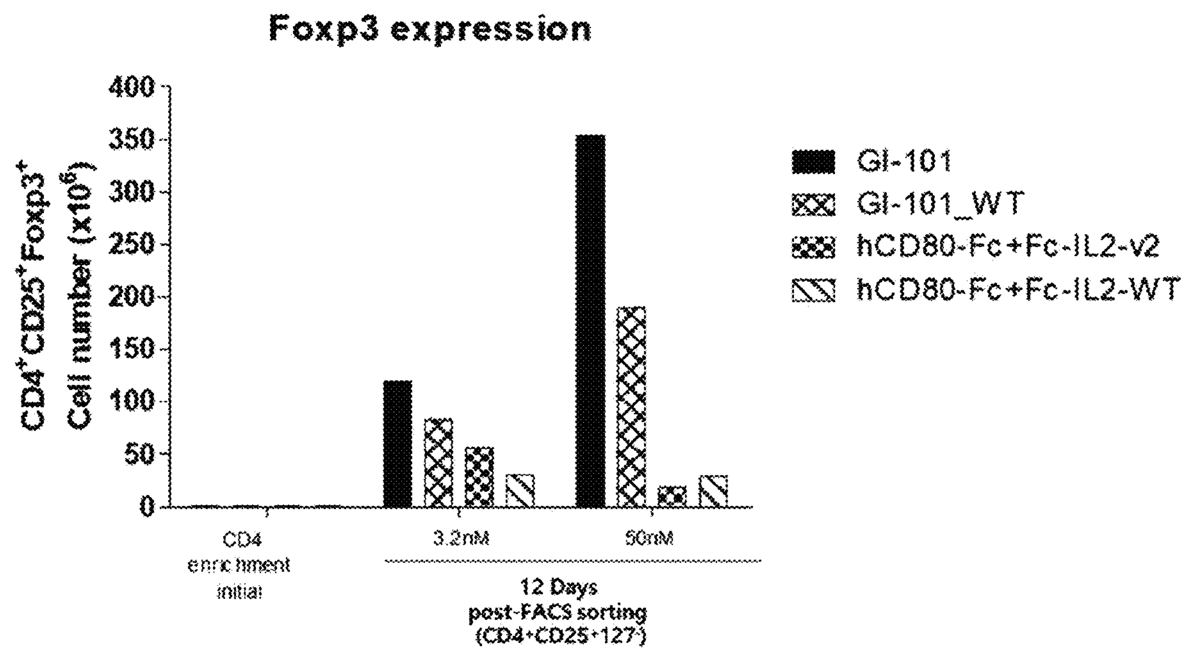
FIGS. 19A to 19C show the number of regulatory T cells expressing Foxp3 when cultured in a composition containing a TexMACS medium in the optimized process.
Figure 19B:
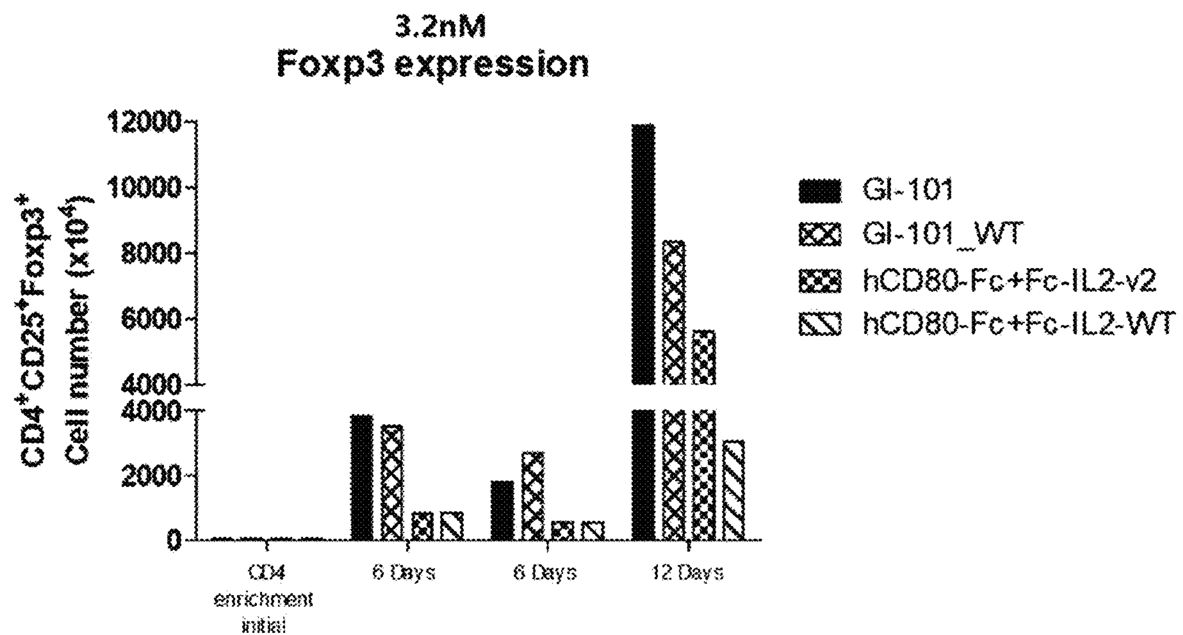
Figure 19C:
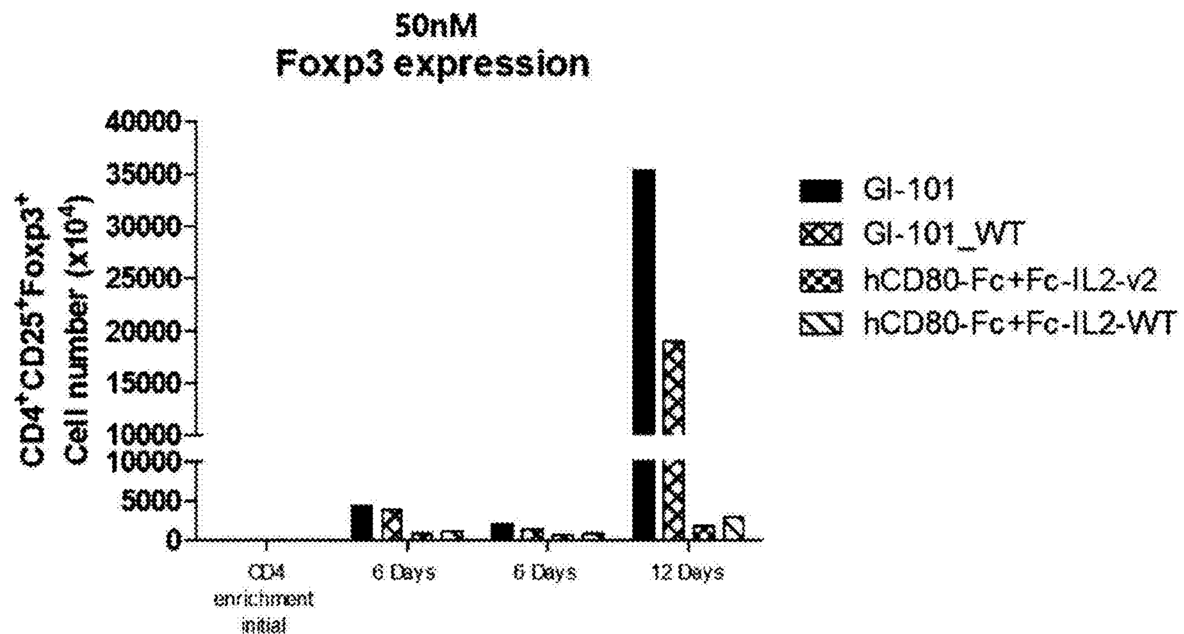

As a result, the results of FACS analysis of the properties of cells cultured in a composition comprising a RPMI1640 medium are as shown in FIGS. 16A to 16C, and the number of T cells expressing CD4+CD25+Foxp3+ confirmed in the above culture conditions is as shown in Table 13 and FIGS. 17A to 17C. In addition, the results of FACS analysis of the properties of cells cultured in a composition comprising a TexMACS medium are as shown in FIGS. 18A to 18C, and the number of T cells expressing CD4+CD25+Foxp3+ confirmed in the above culture conditions is as shown in Table 14 and FIGS. 19A to 19C.

TABLE 13

| Additive for culture composition | | Number of Total cells ($\times10^6$) CD4+ cells 0 Day | CD4+ cells 6 Days | Cell number after CD4+ CD25+ CD127− FACS isolation 6 Days | Cell number after CD4+ CD25+ CD127− FACS isolation 12 Days |
|---|---|---|---|---|---|
| 3.2 nM | GI-101 | 0.25 | 2.1 | 33.3 | 61.3 |
| | GI-101 WT | 0.25 | 0.97 | 18.9 | 30 |
| | hCD80-Fc + Fc-IL-2_v2 | 0.25 | 0.99 | 2.96 | 67 |
| | hCD80-Fc + Fc-IL-2_wt | 0.25 | 1.08 | 7.56 | 18 |
| 50 nM | GI-101 | 0.25 | 7.27 | 27.7 | 98.8 |
| | GI-101 WT | 0.25 | 2.75 | 28.1 | 30.3 |
| | hCD80-Fc + Fc-IL-2_v2 | 0.25 | 2.35 | 1.2 | 11.2 |
| | hCD80-Fc + Fc-IL-2_wt | 0.25 | 1.97 | 3.3 | 20 |

TABLE 14

| Additive for culture composition | | Number of Total cells ($\times10^6$) CD4+ cells 0 Day | CD4+ cells 6 Days | Cell number after CD4+ CD25+ CD127− FACS isolation 6 Days | Cell number after CD4+ CD25+ CD127− FACS isolation 12 Days |
|---|---|---|---|---|---|
| 3.2 nM | GI-101 | 0.3 | 38.4 | 18 | 118.8 |
| | GI-101 WT | 0.3 | 35.3 | 26.7 | 83.4 |
| | hCD80-Fc + Fc-IL-2_v2 | 0.3 | 8.2 | 5.4 | 56.1 |
| | hCD80-Fc + Fc-IL-2_wt | 0.3 | 8.7 | 5.25 | 30.2 |
| 50 nM | GI-101 | 0.3 | 43.1 | 20.8 | 353.5 |
| | GI-101 WT | 0.3 | 38.2 | 13.6 | 189.8 |
| | hCD80-Fc + Fc-IL-2_v2 | 0.3 | 7.7 | 5.3 | 18 |
| | hCD80-Fc + Fc-IL-2_wt | 0.3 | 10.5 | 7.2 | 28.6 |

Example 2.6. Determination of Secretory Capacities of Immunosuppressive Cytokines: Interleukin-10

In order to evaluate the IL-10 secretory capacities of the regulatory T cells obtained in Example 2.4, the cells were cultured so that the number of cells were adjusted to $1\times10^6$ cells/mL, and then the culture supernatant was obtained to be analyzed by ELISA (enzyme-linked immunosorbent assay).

First, 100 µl of incubation buffer of a human IL-10 ELISA Kit (Invitrogen, Cat #KAC1321) was dispensed into each microplate, and then 100 µl of calibration, control, or regulatory T cell culture supernatant sample was added to dispense, respectively. Then, the microplates were covered with an adhesive film and reacted with shaking at 700 rpm at room temperature (18° C. to 25° C.) for 2 hours on a shaker. Next, microwell strips were washed 3 times with about 150 µl of washing buffer per well.

After washing, 100 µl of a specimen diluent was added each. Then, 50 µl of anti-IL-10-HRP was added, and then reacted with shaking at 700 rpm at room temperature for 2 hours, followed by washing 3 times with about 150 µl of washing buffer per well. After washing, 100 µl of TMB was added each, and then reacted at room temperature for 15 minutes, followed by termination of the reaction by adding 100 µl of stop solution. Then, the fluorescence values of each microwell were measured at 450 nm.

Figure 20:
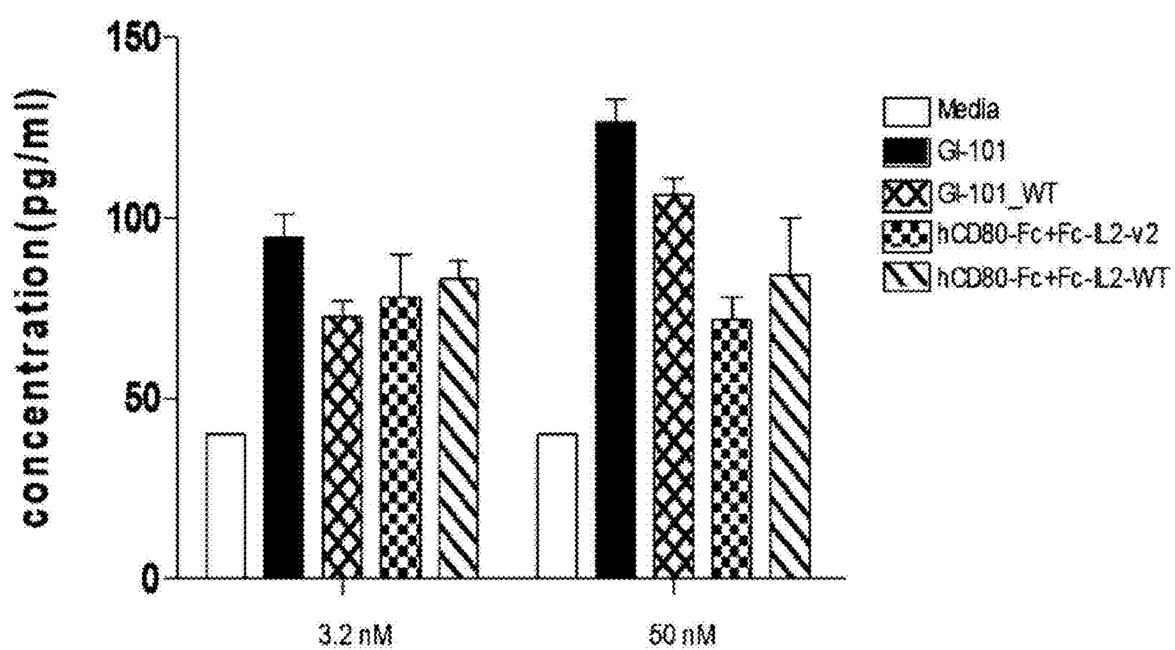
FIG. 20 shows the IL-10 secretory capacity of regulatory T cells when cultured in a composition containing a RPMI1640 medium in the optimized process.
Figure 21:
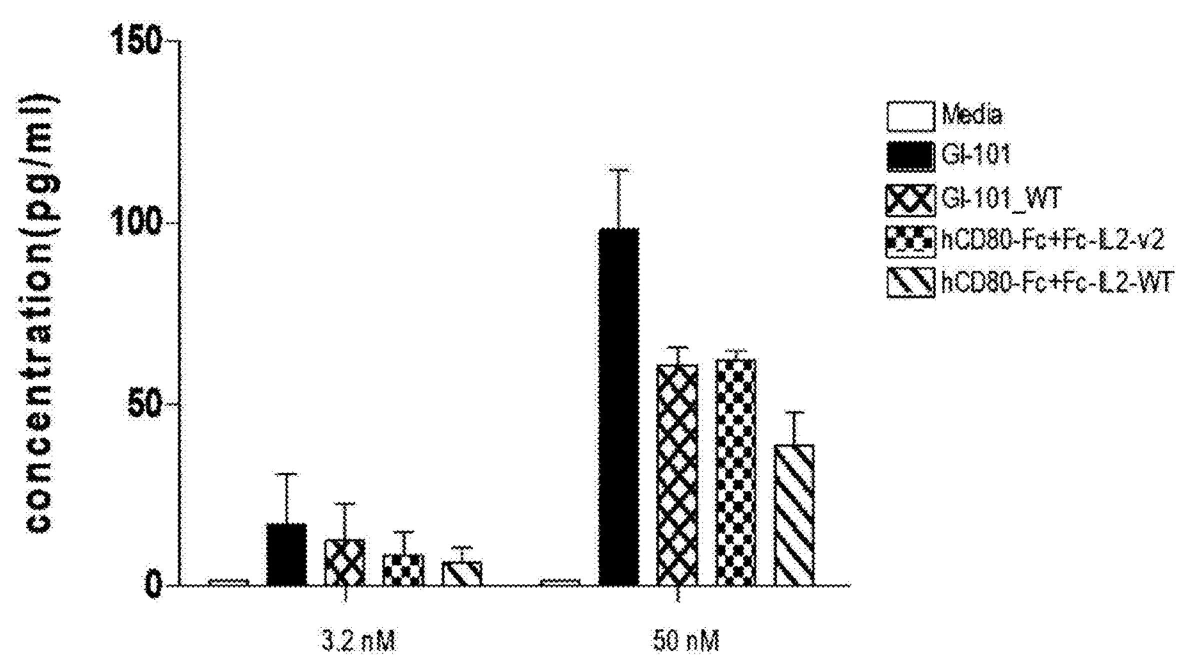
FIG. 21 shows the IL-10 secretory capacity of regulatory T cells when cultured in a composition containing a TexMACS medium.

As a result, the interleukin-10 secretory capacities of the cells cultured in the RPMI1640 medium-containing composition are as shown in FIG. 20, and the interleukin-10 secretory capacities of the cells cultured in the TexMACS medium-comprising composition are as shown in FIG. 21. It was confirmed by FIGS. 20 and 21 that interleukin-10 was highly expressed in regulatory T cells cultured in the culture composition comprising GI-101.

What is claimed is:

1. A method for culturing regulatory T cells comprising:

culturing an isolated regulatory T cells in a medium comprising a fusion protein dimer containing an IL-2 protein or a variant thereof and a CD80 protein or a fragment thereof, wherein the fusion protein comprises the following structural formula (I) or (II):

N'-X-[linker (1)]n-Fc domain-[linker (2)]m-Y-C' -formula (I)

N'-Y-[linker (1)]n-Fc domain-[linker (2)]m-X-C' - formula (II), wherein, N' is the N-terminus of the fusion protein, C' is the C-terminus of the fusion protein, X is a CD80 protein or a fragment thereof, Y is an IL-2 protein or a variant thereof, the linkers (1) and (2) are peptide linkers, and n and m are each independently 0 or 1, wherein the IL-2 protein variant comprises a substitution of the 38th and 42th amino acids in the amino acid sequence of SEQ ID NO: 10, wherein the CD80 protein fragment comprises an extracellular domain of CD80.

2. The method for culturing regulatory T cells according to claim 1, wherein the regulatory T cells are CD4+CD25+CD127−T cells.

3. The method for culturing regulatory T cells according to claim 2, wherein the CD4+CD25+CD127−T cells are obtained by culturing CD4+T cells; or culturing CD25+T cells.

4. The method for culturing regulatory T cells according to claim 1, wherein the IL-2 protein has the amino acid sequence of SEQ ID NO: 10.

5. The method for culturing regulatory T cells according to claim 1, wherein the CD80 has the amino acid sequence of SEQ ID NO: 11.

6. The method for culturing regulatory T cells according to claim 1, wherein the fusion protein has the amino acid sequence of SEQ ID NO: 9.

* * * * *

UNITED STATES PATENT AND TRADEMARK OFFICE

CERTIFICATE OF CORRECTION

PATENT NO. : 11,702,633 B2
APPLICATION NO. : 17/743181
DATED : July 18, 2023
INVENTOR(S) : Myoung Ho Jang et al.

It is certified that error appears in the above-identified patent and that said Letters Patent is hereby corrected as shown below:

In the Specification

Column 3, Line 28, "Fc-IL2 wt" should be -- Fc-IL2wt --.
Column 3, Line 30, "Fc-IL2 wt" should be -- Fc-IL2wt --.
Column 3, Line 32, "hCD80-Fc-IL2 wt" should be -- hCD80-Fc-IL2wt --.
Column 3, Line 34, "hCD80-Fc-IL2 wt" should be -- hCD80-Fc-IL2wt --.
Column 5, Line 23, "($NaH_2PO_4$—$H_2O$)" should be -- ($NaH_2PO_4$-$H_2O$) --.
Column 5, Line 25, "($Fe(NO_3)_3.9H_2O$)" should be -- ($Fe(NO_3)_3 \cdot 9H_2O$) --.
Column 5, Line 30, "($CaCl_2$))(anhydrous))" should be -- ($CaCl_2$)(anhydrous) --.
Column 10, Line 50, "(IL-2Ra)" should be -- (IL-2Rα) --.
Column 10, Line 52, "IL-2Ra" should be -- IL-2Rα --.
Column 10, Line 56, "(IL-2Ra)" should be -- (IL-2Rα) --.
Column 12, Line 51, "(G45)." should be -- $(G4S)_n$ --.
Column 12, Line 52, "$(G45)_n$" should be -- $(G4S)_n$ --.
Column 16, Line 18, "Fc-IL2 wt" should be -- Fc-IL2wt --.
Column 16, Line 36, ""Fc-IL2 wt"" should be -- "Fc-IL2wt" --.
Column 16, Line 67, ""hCD80-Fc-IL2 wt"" should be -- "hCD80-Fc-IL2wt" --.
Column 18, Line 33, "Fc-IL2 wt" should be -- Fc-IL2wt --.
Column 21, Line 33, "(50 nM)+Fc-IL-2 wt" should be -- (50 nM)+Fc-IL-2wt --.
Column 22, Line 28, "(50 nM)+Fc-IL-2 wt" should be -- (50 nM)+Fc-IL-2wt --.
Column 25, Lines 16-17, "(3.2 nM/50 nM)+Fc-IL-2 wt" should be -- (3.2 nM/50 nM)+Fc-IL-2wt --.
Column 26, Line 20, "(3.2nM/50 nM)+Fc-IL-2 wt" should be -- (3.2nM/50 nM)+Fc-IL-2wt --.

Signed and Sealed this
Twenty-ninth Day of August, 2023

Katherine Kelly Vidal

Katherine Kelly Vidal
*Director of the United States Patent and Trademark Office*